US011925332B2

(12) United States Patent
Ma et al.

(10) Patent No.: US 11,925,332 B2
(45) Date of Patent: Mar. 12, 2024

(54) PERCUTANEOUS SHEATH FOR ROBOTIC MEDICAL SYSTEMS AND METHODS

(71) Applicant: Auris Health, Inc., Redwood City, CA (US)

(72) Inventors: Polly Charlene Ma, Fremont, CA (US); Binh T. Nguyen, Newark, CA (US); Ka Chun Wong, South San Francisco, CA (US); Ryan Jeffrey Connolly, San Carlos, CA (US); Javier O. Fajardo Vargas, Daly City, CA (US); Umberto Scarfogliero, Redwood City, CA (US); Zachary Stahl Morrison, Dallas, TX (US)

(73) Assignee: Auris Health, Inc., Redwood City, CA (US)

( * ) Notice: Subject to any disclaimer, the term of this patent is extended or adjusted under 35 U.S.C. 154(b) by 0 days.

(21) Appl. No.: 16/728,948

(22) Filed: Dec. 27, 2019

(65) Prior Publication Data

US 2020/0206472 A1 Jul. 2, 2020

Related U.S. Application Data

(60) Provisional application No. 62/786,152, filed on Dec. 28, 2018.

(51) Int. Cl.
*A61M 25/06* (2006.01)
*A61B 1/00* (2006.01)
(Continued)

(52) U.S. Cl.
CPC .......... *A61B 10/04* (2013.01); *A61B 1/00149* (2013.01); *A61B 1/307* (2013.01);
(Continued)

(58) Field of Classification Search
CPC ...... A61M 25/0662; A61M 2025/0681; A61M 2205/3344; A61M 3/0279; A61B 1/307; A61B 5/201; A61B 10/04
See application file for complete search history.

(56) References Cited

U.S. PATENT DOCUMENTS 5,383,860 A * 1/1995 Lau .................... A61B 17/3421
604/167.03
5,669,876 A 9/1997 Schechter et al.
(Continued)

FOREIGN PATENT DOCUMENTS

CN 108324234 A 7/2018
EP 2 615 992 7/2016
(Continued)

OTHER PUBLICATIONS

International search report and written opinion dated May 11, 2020 in application No. PCT/US2019/68802.
(Continued)

*Primary Examiner* — Jason E Flick
*Assistant Examiner* — Justin L Zamory
(74) *Attorney, Agent, or Firm* — Chang & Hale LLP

(57) ABSTRACT

Certain aspects relate to percutaneous sheaths for medical procedures as well as to related systems and methods. For example, a system for performing a percutaneous assisted medical procedure can include a percutaneous sheath. The percutaneous sheath can include a first conduit for providing aspiration into the kidney and a second conduit for passing a catheter into the kidney. The system can also include an aspiration catheter configured to be inserted into the kidney through the second conduit of the percutaneous sheath. A fluidics system can include an irrigation source comprising a pump and an aspiration source comprising a vacuum. The irrigation source can be connected to a fluid inlet of the percutaneous sheath that is connected to the first conduit.
(Continued)

The aspiration source can be connected to the aspiration catheter.

21 Claims, 28 Drawing Sheets

(51) Int. Cl.
| | |
|---|---|
| *A61B 1/307* | (2006.01) |
| *A61B 5/20* | (2006.01) |
| *A61B 10/04* | (2006.01) |
| *A61B 17/22* | (2006.01) |
| *A61B 34/20* | (2016.01) |
| *A61B 34/37* | (2016.01) |
| *A61B 50/13* | (2016.01) |
| *A61G 13/04* | (2006.01) |
| *A61M 1/00* | (2006.01) |
| *A61M 3/02* | (2006.01) |
| *A61M 29/02* | (2006.01) |
| *A61B 34/30* | (2016.01) |

(52) U.S. Cl.
CPC .......... *A61B 5/201* (2013.01); *A61B 17/2202* (2013.01); *A61B 34/20* (2016.02); *A61B 34/37* (2016.02); *A61B 50/13* (2016.02); *A61G 13/04* (2013.01); *A61M 1/85* (2021.05); *A61M 3/0258* (2013.01); *A61M 3/0279* (2013.01); *A61M 3/0283* (2013.01); *A61M 25/0662* (2013.01); *A61M 29/02* (2013.01); *A61B 2010/045* (2013.01); *A61B 2034/2051* (2016.02); *A61B 2034/2061* (2016.02); *A61B 2034/301* (2016.02); *A61M 2025/0681* (2013.01); *A61M 2205/3334* (2013.01); *A61M 2205/3344* (2013.01); *A61M 2205/50* (2013.01); *A61M 2210/1082* (2013.01)

(56) References Cited

U.S. PATENT DOCUMENTS

| | | | |
|---|---|---|---|
| 6,149,642 A * | 11/2000 | Gerhart | A61B 17/00234 128/897 |
| 6,428,498 B2 * | 8/2002 | Uflacker | A61M 1/85 604/22 |
| 9,173,713 B2 | 11/2015 | Hart et al. | |
| 9,259,274 B2 | 2/2016 | Prisco | |
| 9,302,702 B1 | 4/2016 | Schepmann | |
| 9,375,522 B2 * | 6/2016 | Qureshi | A61M 1/85 |
| 9,504,604 B2 | 11/2016 | Alvarez | |
| 9,561,083 B2 | 2/2017 | Yu et al. | |
| 9,622,827 B2 | 4/2017 | Yu et al. | |
| 9,636,184 B2 | 5/2017 | Lee et al. | |
| 9,713,509 B2 | 7/2017 | Schuh et al. | |
| 9,717,563 B2 | 8/2017 | Tognaccini | |
| 9,727,963 B2 | 8/2017 | Mintz et al. | |
| 9,737,371 B2 | 8/2017 | Romo et al. | |
| 9,737,373 B2 | 8/2017 | Schuh | |
| 9,744,335 B2 | 8/2017 | Jiang | |
| 9,763,741 B2 | 9/2017 | Alvarez et al. | |
| 9,788,910 B2 | 10/2017 | Schuh | |
| 9,839,481 B2 | 12/2017 | Blumenkranz et al. | |
| 9,844,412 B2 | 12/2017 | Bogusky et al. | |
| 9,867,635 B2 | 1/2018 | Alvarez et al. | |
| 9,918,681 B2 | 3/2018 | Wallace et al. | |
| 9,931,025 B1 | 4/2018 | Graetzel et al. | |
| 9,949,749 B2 | 4/2018 | Noonan et al. | |
| 9,955,986 B2 | 5/2018 | Shah | |
| 9,962,228 B2 | 5/2018 | Schuh et al. | |
| 9,980,785 B2 | 5/2018 | Schuh | |
| 9,993,313 B2 | 6/2018 | Schuh et al. | |
| 10,016,900 B1 | 7/2018 | Meyer et al. | |
| 10,022,192 B1 | 7/2018 | Ummalaneni | |
| 10,080,576 B2 | 9/2018 | Romo et al. | |
| 10,136,959 B2 | 11/2018 | Mintz et al. | |
| 10,145,747 B1 | 12/2018 | Lin et al. | |
| 10,149,720 B2 | 12/2018 | Romo | |
| 10,159,532 B1 | 12/2018 | Ummalaneni et al. | |
| 10,159,533 B2 | 12/2018 | Moll et al. | |
| 10,169,875 B2 | 1/2019 | Mintz et al. | |
| 10,213,264 B2 | 2/2019 | Tanner et al. | |
| 10,219,874 B2 | 3/2019 | Yu et al. | |
| 10,231,793 B2 | 3/2019 | Romo | |
| 10,231,867 B2 | 3/2019 | Alvarez et al. | |
| 10,244,926 B2 | 4/2019 | Noonan et al. | |
| 10,285,574 B2 | 5/2019 | Landey et al. | |
| 10,299,870 B2 | 5/2019 | Connolly et al. | |
| 10,314,463 B2 | 6/2019 | Agrawal et al. | |
| 10,383,765 B2 | 8/2019 | Alvarez et al. | |
| 10,398,518 B2 | 9/2019 | Yu et al. | |
| 10,405,939 B2 | 9/2019 | Romo et al. | |
| 10,405,940 B2 | 9/2019 | Romo | |
| 10,426,559 B2 | 10/2019 | Graetzel et al. | |
| 10,426,661 B2 | 10/2019 | Kintz | |
| 10,434,660 B2 | 10/2019 | Meyer | |
| 10,464,209 B2 | 11/2019 | Ho et al. | |
| 10,470,830 B2 | 11/2019 | Hill | |
| 10,482,599 B2 | 11/2019 | Mintz et al. | |
| 10,493,241 B2 | 12/2019 | Jiang | |
| 10,500,001 B2 | 12/2019 | Yu et al. | |
| 10,517,692 B2 | 12/2019 | Eyre et al. | |
| 10,524,866 B2 | 1/2020 | Srinivasan | |
| 10,539,478 B2 | 1/2020 | Lin | |
| 10,543,048 B2 | 1/2020 | Noonan et al. | |
| 10,639,114 B2 | 5/2020 | Schuh | |
| 2002/0128535 A1 * | 9/2002 | Kikuchi | A61B 1/0011 600/101 |
| 2003/0158539 A1 * | 8/2003 | Bouphavichith | A61M 39/0247 604/533 |
| 2003/0181809 A1 | 9/2003 | Hall et al. | |
| 2006/0025749 A1 * | 2/2006 | Moenning | A61M 39/02 604/506 |
| 2006/0149189 A1 * | 7/2006 | Diamond | A61M 5/007 604/246 |
| 2007/0232856 A1 | 10/2007 | Ueno | |
| 2008/0046122 A1 | 2/2008 | Manzo et al. | |
| 2008/0140087 A1 | 6/2008 | Barbagli | |
| 2009/0062611 A1 * | 3/2009 | Toyama | A61B 1/015 600/118 |
| 2009/0259099 A1 | 10/2009 | Zhou et al. | |
| 2010/0082041 A1 | 4/2010 | Prisco | |
| 2010/0198170 A1 | 8/2010 | Umeda et al. | |
| 2010/0204713 A1 | 8/2010 | Ruiz | |
| 2010/0228266 A1 | 9/2010 | Hourtash | |
| 2010/0312338 A1 * | 12/2010 | Gonzales | A61B 17/24 623/10 |
| 2010/0331766 A1 * | 12/2010 | Hayakawa | A61M 13/003 604/24 |
| 2011/0015484 A1 | 1/2011 | Alvarez et al. | |
| 2012/0071894 A1 | 3/2012 | Tanner et al. | |
| 2012/0221007 A1 | 8/2012 | Batten et al. | |
| 2012/0239060 A1 | 9/2012 | Orban, III | |
| 2012/0302869 A1 | 11/2012 | Koyrakh | |
| 2013/0123580 A1 | 5/2013 | Peters | |
| 2013/0165944 A1 | 6/2013 | Gal et al. | |
| 2013/0209208 A1 | 8/2013 | Bailey | |
| 2013/0218005 A1 | 8/2013 | Desai | |
| 2013/0253565 A1 * | 9/2013 | Myers | A61M 39/0613 606/194 |
| 2013/0274783 A1 | 10/2013 | Wynberg | |
| 2014/0001235 A1 | 1/2014 | Shelton, IV | |
| 2014/0142591 A1 | 5/2014 | Alvarez et al. | |
| 2014/0257333 A1 | 9/2014 | Blumenkranz | |
| 2014/0276933 A1 | 9/2014 | Hart | |
| 2014/0309625 A1 | 10/2014 | Okamoto et al. | |
| 2014/0357984 A1 | 12/2014 | Wallace et al. | |
| 2014/0364870 A1 | 12/2014 | Alvarez et al. | |
| 2015/0119645 A1 | 4/2015 | Baldwin | |
| 2015/0150636 A1 | 6/2015 | Hagn et al. | |
| 2015/0305650 A1 | 10/2015 | Hunter | |
| 2015/0311838 A1 | 10/2015 | Maule | |

(56) References Cited

U.S. PATENT DOCUMENTS

| | | |
|---|---|---|
| 2016/0001038 A1 | 1/2016 | Romo et al. |
| 2016/0166320 A1 | 6/2016 | Ciulla |
| 2016/0270865 A1 | 9/2016 | Landey et al. |
| 2016/0287279 A1 | 10/2016 | Bovay et al. |
| 2017/0007337 A1 | 1/2017 | Dan |
| 2017/0106904 A1 | 4/2017 | Hanson |
| 2017/0119481 A1 | 5/2017 | Romo et al. |
| 2017/0135718 A1 | 5/2017 | Lyons |
| 2017/0165011 A1 | 6/2017 | Bovay et al. |
| 2017/0209162 A1 | 6/2017 | Sperry |
| 2017/0189118 A1 | 7/2017 | Chopra |
| 2017/0196576 A1 | 7/2017 | Long et al. |
| 2017/0202627 A1 | 7/2017 | Sramek et al. |
| 2017/0209073 A1 | 7/2017 | Sramek et al. |
| 2017/0231647 A1 | 8/2017 | Saunders |
| 2017/0245854 A1 | 8/2017 | Zemlok |
| 2017/0290631 A1 | 10/2017 | Lee et al. |
| 2017/0326337 A1 | 11/2017 | Romascanu |
| 2017/0340396 A1 | 11/2017 | Romo et al. |
| 2017/0367782 A1 | 12/2017 | Schuh et al. |
| 2018/0025666 A1 | 1/2018 | Ho et al. |
| 2018/0169671 A1 | 6/2018 | Winter |
| 2018/0177556 A1 | 6/2018 | Noonan et al. |
| 2018/0214011 A1 | 8/2018 | Graetzel et al. |
| 2018/0221038 A1 | 8/2018 | Noonan et al. |
| 2018/0221039 A1 | 8/2018 | Shah |
| 2018/0250083 A1 | 9/2018 | Schuh et al. |
| 2018/0271616 A1 | 9/2018 | Schuh et al. |
| 2018/0279852 A1 | 10/2018 | Rafii-Tari et al. |
| 2018/0280660 A1 | 10/2018 | Landey et al. |
| 2018/0289394 A1* | 10/2018 | Shah ............... A61B 1/00142 |
| 2018/0289431 A1 | 10/2018 | Draper et al. |
| 2018/0325499 A1 | 11/2018 | Landey et al. |
| 2018/0333044 A1 | 11/2018 | Jenkins |
| 2018/0360435 A1 | 12/2018 | Romo |
| 2019/0000559 A1 | 1/2019 | Berman et al. |
| 2019/0000560 A1 | 1/2019 | Berman et al. |
| 2019/0000576 A1 | 1/2019 | Mintz et al. |
| 2019/0083183 A1 | 3/2019 | Moll et al. |
| 2019/0110839 A1 | 4/2019 | Rafii-Tari et al. |
| 2019/0110843 A1 | 4/2019 | Ummalaneni et al. |
| 2019/0151148 A1 | 4/2019 | Alvarez et al. |
| 2019/0167366 A1 | 6/2019 | Ummalaneni |
| 2019/0175009 A1 | 6/2019 | Mintz |
| 2019/0175062 A1 | 6/2019 | Rafii-Tari et al. |
| 2019/0175799 A1 | 6/2019 | Hsu |
| 2019/0183585 A1 | 6/2019 | Rafii-Tari et al. |
| 2019/0183587 A1 | 6/2019 | Rafii-Tari et al. |
| 2019/0216548 A1 | 7/2019 | Ummalaneni |
| 2019/0216576 A1 | 7/2019 | Eyre |
| 2019/0223974 A1 | 7/2019 | Romo |
| 2019/0228525 A1 | 7/2019 | Mintz et al. |
| 2019/0246882 A1 | 8/2019 | Graetzel et al. |
| 2019/0262086 A1 | 8/2019 | Connolly et al. |
| 2019/0269468 A1 | 9/2019 | Hsu et al. |
| 2019/0274764 A1 | 9/2019 | Romo |
| 2019/0290109 A1 | 9/2019 | Agrawal et al. |
| 2019/0298160 A1 | 10/2019 | Ummalaneni et al. |
| 2019/0298460 A1 | 10/2019 | Al-Jadda |
| 2019/0298465 A1 | 10/2019 | Chin |
| 2019/0328213 A1 | 10/2019 | Landey et al. |
| 2019/0336238 A1 | 11/2019 | Yu |
| 2019/0365209 A1 | 12/2019 | Ye et al. |
| 2019/0365479 A1 | 12/2019 | Rafii-Tari |
| 2019/0365486 A1 | 12/2019 | Srinivasan et al. |
| 2019/0374297 A1 | 12/2019 | Wallace et al. |
| 2019/0375383 A1 | 12/2019 | Alvarez |
| 2019/0380787 A1 | 12/2019 | Ye |
| 2019/0380797 A1 | 12/2019 | Yu |
| 2020/0000530 A1 | 1/2020 | DeFonzo |
| 2020/0000533 A1 | 1/2020 | Schuh |
| 2020/0022767 A1 | 1/2020 | Hill |
| 2020/0039086 A1 | 2/2020 | Meyer |
| 2020/0046434 A1 | 2/2020 | Graetzel |
| 2020/0054408 A1 | 2/2020 | Schuh et al. |
| 2020/0060516 A1 | 2/2020 | Baez |
| 2020/0093549 A1 | 3/2020 | Chin |
| 2020/0093554 A1 | 3/2020 | Schuh |
| 2020/0100811 A1 | 4/2020 | Holsten |
| 2020/0100845 A1 | 4/2020 | Julian |
| 2020/0100853 A1 | 4/2020 | Ho |
| 2020/0100855 A1 | 4/2020 | Leparmentier |
| 2020/0101264 A1 | 4/2020 | Jiang |
| 2020/0107894 A1 | 4/2020 | Wallace |
| 2020/0121502 A1 | 4/2020 | Kintz |
| 2020/0146769 A1 | 5/2020 | Eyre |
| 2020/0188043 A1 | 6/2020 | Yu |
| 2020/0197112 A1 | 6/2020 | Chin |
| 2020/0217733 A1 | 7/2020 | Lin |
| 2020/0222134 A1 | 7/2020 | Schuh |
| 2020/0237458 A1 | 7/2020 | DeFonzo |
| 2020/0261172 A1 | 8/2020 | Romo |
| 2020/0268459 A1 | 8/2020 | Noonan et al. |
| 2020/0268460 A1 | 8/2020 | Tse |

FOREIGN PATENT DOCUMENTS

| | | |
|---|---|---|
| GB | 2268883 A | 1/1994 |
| JP | H1135342 A | 2/1999 |
| WO | WO 10/127162 | 11/2010 |
| WO | WO 11/002215 | 1/2011 |
| WO | 2011079958 A1 | 7/2011 |
| WO | WO 12/082719 | 6/2012 |
| WO | WO 17/048194 | 3/2017 |
| WO | WO 17/053698 | 3/2017 |
| WO | 2017075574 A1 | 5/2017 |
| WO | WO 18/098477 | 5/2018 |

OTHER PUBLICATIONS

EP Search Report for Appl. No. 19902394.6, dated Jun. 21, 2022, 13 pages.

JP Office Action for Appl. No. 2021-537797, dated Sep. 8, 2023, 10 pages.

\* cited by examiner

PERCUTANEOUS SHEATH FOR ROBOTIC MEDICAL SYSTEMS AND METHODS

INCORPORATION BY REFERENCE TO ANY PRIORITY APPLICATIONS

This application claims priority to U.S. Provisional Application No. 62/786,152, filed Dec. 28, 2018, which is incorporated by reference in its entirety. Any and all applications for which a foreign or domestic priority claim is identified in the Application Data Sheet as filed with the present application are hereby incorporated by reference under 37 CFR 1.57.

TECHNICAL FIELD

This application relates generally to percutaneous assisted medical procedures, and in particular to percutaneous sheaths for robotic medical systems and related methods.

BACKGROUND

Physicians regularly perform procedures to remove urinary stones from patients' urinary tracts. Urinary stones may form as a result of concentrated minerals and may cause significant abdominal pain once they reach a size sufficient to impede urine flow through the ureter or urethra. Such stones may be formed from calcium, magnesium, ammonia, uric acid, cysteine, or other compounds.

To remove urinary stones from the bladder and ureter, physicians generally use a ureteroscope inserted into the urinary tract through the urethra. Typically, a ureteroscope includes a scope at its distal end to enable visualization of the urinary tract. The procedure may also utilize a lithotomy mechanism to capture or break apart the urinary stones. During the ureteroscopy procedure, one physician may control the position of the ureteroscope and the other physician may control the lithotomy mechanism. To remove large kidney stones from the kidneys, physicians generally use a percutaneous nephrolithotomy (PCNL) technique that includes inserting a nephroscope through the skin (e.g., percutaneously) to break up and remove the kidney stones.

SUMMARY

This disclosure relates to percutaneous sheaths, as well as to related systems and methods. The percutaneous sheaths can be configured for use in percutaneous assisted medical procedures, such as percutaneous assisted ureteroscopy (PAU) and percutaneous nephrolithotomy (PCNL) and others. The percutaneous sheaths can be configured to perform several functions, including establishing and maintaining a path from outside the patient's body into the treatment site, and providing conduits for irrigation and/or aspiration.

In a first aspect, a method for percutaneous assisted ureteroscopy can include percutaneously inserting a renal sheath into a kidney, inserting a catheter into the kidney through a first conduit of the renal sheath device, and providing irrigation into the kidney through a second conduit of the renal sheath device.

The method can include one or more of the following features in any combination: (a) providing aspiration from the kidney through the catheter; (b) providing passive outflow from the kidney through the first conduit of the renal sheath; (c) wherein the passive outflow flows through a channel formed between the second conduit of the renal sheath and the catheter; (d) connecting a fluid inlet of the renal sheath to an irrigation source of a fluidics system, the fluid inlet connected to the second conduit of the renal sheath device; (e) wherein the fluid inlet comprises a side port positioned on the renal sheath; (f) connecting the catheter to an aspiration source of a fluidics system; (g) wherein the renal sheath comprises a valve, and inserting the catheter into the kidney through the first conduit of the renal sheath device comprises inserting the catheter through the; (h) inserting an endoscope into the kidney through a natural patient orifice, performing lithotomy with the endoscope to break a kidney stone into fragments, and aspirating the fragments through the catheter; (i) wherein the endoscope is robotically controlled; (j) wherein the catheter is robotically controlled; and/or (k) wherein percutaneously inserting the renal sheath into the kidney comprises percutaneously inserting a dilator into the kidney, inserting the renal sheath over the dilator, and removing the dilator.

In another aspect a percutaneous sheath can include an outer conduit extending between a proximal end and a distal end, the outer conduit sufficiently rigid to be percutaneously inserted into a kidney, an inner conduit arranged within the outer conduit, a fluid inlet configured to connect to an irrigation source, a first channel defined between the outer conduit and the inner conduit, the first channel connected to the fluid inlet to provide irrigation of a fluid into the kidney, and a second channel formed by the inner conduit. The second channel is configured to allow a catheter to be inserted through the second channel and into the kidney, and provide for passive outflow of the fluid from the kidney in a space between the catheter and the inner conduit.

The sheath can include one or more of the following features in any combination: (a) wherein the fluid inlet comprises a side port positioned on a first hub attached to a proximal end of the first conduit; (b) a second hub attached to a proximal end of the second conduit, wherein the second hub engages the first hub to seal a proximal end of the first channel; (c) wherein the hub comprises a valve, the second fluid conduit extends through the valve, and the valve seals a proximal end of the first conduit; (d) wherein the first conduit and the second conduit are concentrically arranged; (e) wherein the second conduit provides an open passage through the sheath; (f) wherein the first conduit comprises a stainless steel hypotube; (g) wherein the second conduit comprises a stainless steel hypotube; (h) wherein an outer diameter of the outer conduit is about 23 Fr., and an inner diameter of the outer conduit is about 21.4 F; (i) wherein an outer diameter of the inner conduit is about 19.1 Fr., and an inner diameter of the inner conduit is about 18.1 Fr.; (j) a pressure sensor for measuring a pressure within the kidney; (k) a flow sensor for measuring a flow rate into the kidney; and/or (l) a flow sensor for measuring a flow rate out of the kidney.

In another aspect, a percutaneous sheath for performing percutaneous assisted ureteroscopy can include a conduit extending between a proximal end and a distal end, the conduit sufficiently rigid to be percutaneously inserted into a kidney and a hub connected to the proximal end of the conduit. The hub can include a fluid inlet configured to connect to an irrigation source, and a pressure relief valve configured to receive a catheter there through, wherein the pressure relief valve seals the proximal end of the conduit around the catheter until a fluid pressure within the kidney exceeds a threshold.

The sheath can include one or more of the following features in any combination: (a) wherein the fluid inlet comprises a side port; (b) wherein the conduit comprises a stainless steel hypotube; and/or (c) wherein an outer diameter of the first conduit is about 23 Fr., and an inner diameter of the first conduit is about 21.4 Fr.

In another aspect, a system for performing percutaneous assisted ureteroscopy can include a percutaneous sheath comprising a first conduit for providing aspiration into the kidney and a second conduit for passing a catheter into the kidney, and an aspiration catheter configured to be inserted into the kidney through the second conduit of the percutaneous renal sheath.

The system can include one or more of the following features in any combination: (a) wherein the second conduit of the percutaneous renal sheath is configured to allow passive outflow from the kidney when the aspiration catheter is inserted through the second conduit; (b) a fluidics system for providing aspiration and irrigation of the kidney, the fluidics system comprising an irrigation source comprising a pump, and an aspiration source comprising a vacuum; (c) wherein the irrigation source is connected to a fluid inlet of the percutaneous renal sheath, the fluid inlet connected to the first conduit, and the aspiration source is connected to the catheter; (d) wherein the fluidics system further comprises a processor configured to control irrigation and aspiration; (e) one or more pressure or flow sensors, and wherein the processor is configured to control irrigation and aspiration based on the output of the one or more pressure or flow sensors; (f) wherein the catheter is robotically controlled; and/or (g) a robotically controllable endoscope.

These and other aspects of this disclosure will be described in more detail below. The above summary is provided by way of introduction and is not intended to be limiting.

BRIEF DESCRIPTION OF THE DRAWINGS

The disclosed aspects will hereinafter be described in conjunction with the appended drawings, provided to illustrate and not to limit the disclosed aspects, wherein like designations denote like elements.

DETAILED DESCRIPTION

1. Overview.

Aspects of the present disclosure may be integrated into a robotically-enabled medical system capable of performing a variety of medical procedures, including both minimally invasive, such as laparoscopy, and non-invasive, such as endoscopy, procedures. Among endoscopic procedures, the system may be capable of performing bronchoscopy, ureteroscopy, gastroscopy, etc.

In addition to performing the breadth of procedures, the system may provide additional benefits, such as enhanced imaging and guidance to assist the physician. Additionally, the system may provide the physician with the ability to perform the procedure from an ergonomic position without the need for awkward arm motions and positions. Still further, the system may provide the physician with the ability to perform the procedure with improved ease of use such that one or more of the instruments of the system can be controlled by a single user.

Various embodiments will be described below in conjunction with the drawings for purposes of illustration. It should be appreciated that many other implementations of the disclosed concepts are possible, and various advantages can be achieved with the disclosed implementations. Headings are included herein for reference and to aid in locating various sections. These headings are not intended to limit the scope of the concepts described with respect thereto. Such concepts may have applicability throughout the entire specification.

A. Robotic System—Cart.

Figure 1:
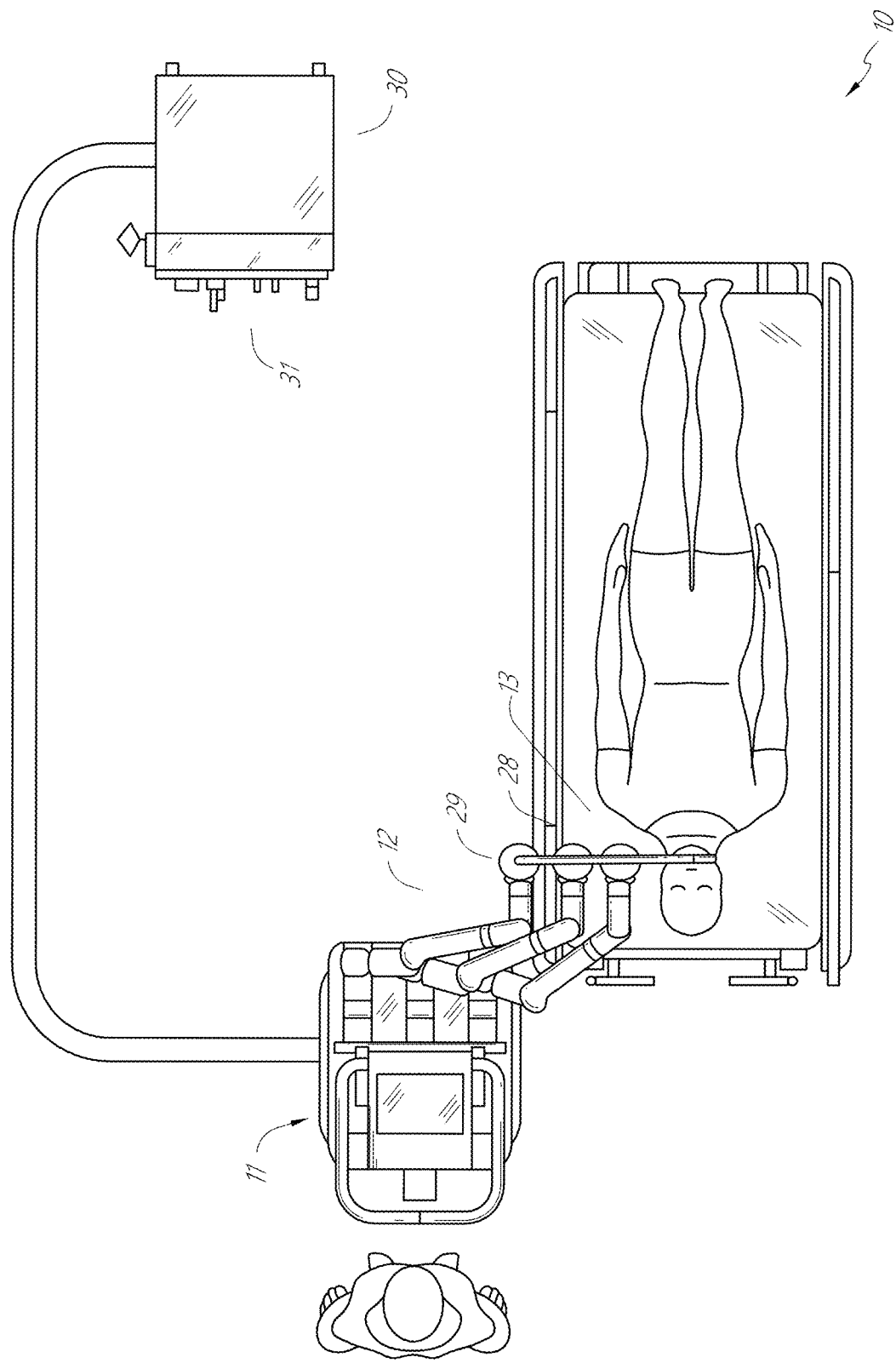
FIG. 1 illustrates an embodiment of a cart-based robotic system arranged for diagnostic and/or therapeutic bronchoscopy.
Figure 2:
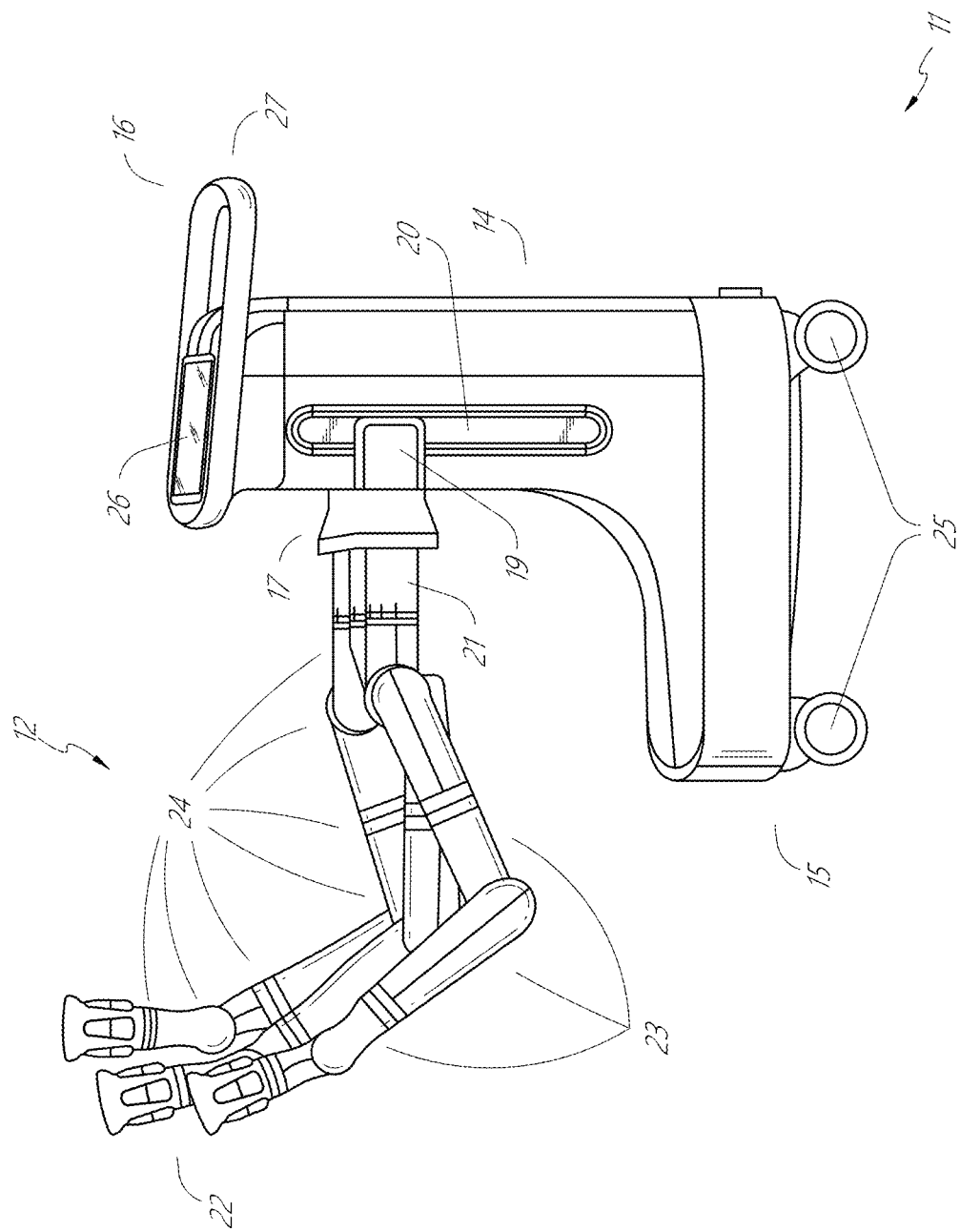
FIG. 2 depicts further aspects of the robotic system of FIG. 1.

The robotically-enabled medical system may be configured in a variety of ways depending on the particular procedure. FIG. 1 illustrates an embodiment of a cart-based robotically-enabled system 10 arranged for a diagnostic and/or therapeutic bronchoscopy. During a bronchoscopy, the system 10 may comprise a cart 11 having one or more robotic arms 12 to deliver a medical instrument, such as a steerable endoscope 13, which may be a procedure-specific bronchoscope for bronchoscopy, to a natural orifice access point (i.e., the mouth of the patient positioned on a table in the present example) to deliver diagnostic and/or therapeutic tools. As shown, the cart 11 may be positioned proximate to the patient's upper torso in order to provide access to the access point. Similarly, the robotic arms 12 may be actuated to position the bronchoscope relative to the access point. The arrangement in FIG. 1 may also be utilized when performing a gastro-intestinal (GI) procedure with a gastroscope, a specialized endoscope for GI procedures. FIG. 2 depicts an example embodiment of the cart in greater detail.

With continued reference to FIG. 1, once the cart 11 is properly positioned, the robotic arms 12 may insert the steerable endoscope 13 into the patient robotically, manually, or a combination thereof. As shown, the steerable endoscope 13 may comprise at least two telescoping parts, such as an inner leader portion and an outer sheath portion, each portion coupled to a separate instrument driver from the set of instrument drivers 28, each instrument driver coupled to the distal end of an individual robotic arm. This linear arrangement of the instrument drivers 28, which facilitates coaxially aligning the leader portion with the sheath portion, creates a "virtual rail" 29 that may be repositioned in space by manipulating the one or more robotic arms 12 into different angles and/or positions. The virtual rails described herein are depicted in the Figures using dashed lines, and accordingly the dashed lines do not depict any physical structure of the system. Translation of the instrument drivers 28 along the virtual rail 29 telescopes the inner leader portion relative to the outer sheath portion or advances or retracts the endoscope 13 from the patient. The angle of the virtual rail 29 may be adjusted, translated, and pivoted based on clinical application or physician preference. For example, in bronchoscopy, the angle and position of the virtual rail 29 as shown represents a compromise between providing physician access to the endoscope 13 while minimizing friction that results from bending the endoscope 13 into the patient's mouth.

The endoscope 13 may be directed down the patient's trachea and lungs after insertion using precise commands from the robotic system until reaching the target destination or operative site. In order to enhance navigation through the patient's lung network and/or reach the desired target, the endoscope 13 may be manipulated to telescopically extend the inner leader portion from the outer sheath portion to obtain enhanced articulation and greater bend radius. The use of separate instrument drivers 28 also allows the leader portion and sheath portion to be driven independently of each other.

For example, the endoscope 13 may be directed to deliver a biopsy needle to a target, such as, for example, a lesion or nodule within the lungs of a patient. The needle may be deployed down a working channel that runs the length of the endoscope to obtain a tissue sample to be analyzed by a pathologist. Depending on the pathology results, additional tools may be deployed down the working channel of the endoscope for additional biopsies. After identifying a nodule to be malignant, the endoscope 13 may endoscopically deliver tools to resect the potentially cancerous tissue. In some instances, diagnostic and therapeutic treatments can be delivered in separate procedures. In those circumstances, the endoscope 13 may also be used to deliver a fiducial to "mark" the location of the target nodule as well. In other instances, diagnostic and therapeutic treatments may be delivered during the same procedure.

The system 10 may also include a movable tower 30, which may be connected via support cables to the cart 11 to provide support for controls, electronics, fluidics, optics, sensors, and/or power to the cart 11. Placing such functionality in the tower 30 allows for a smaller form factor cart 11 that may be more easily adjusted and/or re-positioned by an operating physician and his/her staff. Additionally, the division of functionality between the cart/table and the support tower 30 reduces operating room clutter and facilitates improving clinical workflow. While the cart 11 may be positioned close to the patient, the tower 30 may be stowed in a remote location to stay out of the way during a procedure.

In support of the robotic systems described above, the tower 30 may include component(s) of a computer-based control system that stores computer program instructions, for example, within a non-transitory computer-readable storage medium such as a persistent magnetic storage drive, solid state drive, etc. The execution of those instructions, whether the execution occurs in the tower 30 or the cart 11, may control the entire system or sub-system(s) thereof. For example, when executed by a processor of the computer system, the instructions may cause the components of the robotics system to actuate the relevant carriages and arm mounts, actuate the robotics arms, and control the medical instruments. For example, in response to receiving the control signal, the motors in the joints of the robotics arms may position the arms into a certain posture.

The tower 30 may also include a pump, flow meter, valve control, and/or fluid access in order to provide controlled irrigation and aspiration capabilities to the system that may be deployed through the endoscope 13. These components may also be controlled using the computer system of the tower 30. In some embodiments, irrigation and aspiration capabilities may be delivered directly to the endoscope 13 through separate cable(s).

The tower 30 may include a voltage and surge protector designed to provide filtered and protected electrical power to the cart 11, thereby avoiding placement of a power transformer and other auxiliary power components in the cart 11, resulting in a smaller, more moveable cart 11.

The tower 30 may also include support equipment for the sensors deployed throughout the robotic system 10. For example, the tower 30 may include optoelectronics equipment for detecting, receiving, and processing data received from the optical sensors or cameras throughout the robotic system 10. In combination with the control system, such optoelectronics equipment may be used to generate real-time images for display in any number of consoles deployed throughout the system, including in the tower 30. Similarly, the tower 30 may also include an electronic subsystem for receiving and processing signals received from deployed electromagnetic (EM) sensors. The tower 30 may also be used to house and position an EM field generator for detection by EM sensors in or on the medical instrument.

The tower 30 may also include a console 31 in addition to other consoles available in the rest of the system, e.g., console mounted on top of the cart. The console 31 may include a user interface and a display screen, such as a touchscreen, for the physician operator. Consoles in the system 10 are generally designed to provide both robotic controls as well as preoperative and real-time information of the procedure, such as navigational and localization information of the endoscope 13. When the console 31 is not the only console available to the physician, it may be used by a second operator, such as a nurse, to monitor the health or vitals of the patient and the operation of the system 10, as well as to provide procedure-specific data, such as navigational and localization information. In other embodiments, the console 30 is housed in a body that is separate from the tower 30.

The tower 30 may be coupled to the cart 11 and endoscope 13 through one or more cables or connections (not shown). In some embodiments, the support functionality from the tower 30 may be provided through a single cable to the cart 11, simplifying and de-cluttering the operating room. In other embodiments, specific functionality may be coupled in separate cabling and connections. For example, while power may be provided through a single power cable to the cart 11, the support for controls, optics, fluidics, and/or navigation may be provided through a separate cable.

FIG. 2 provides a detailed illustration of an embodiment of the cart 11 from the cart-based robotically-enabled system shown in FIG. 1. The cart 11 generally includes an elongated support structure 14 (often referred to as a "column"), a cart base 15, and a console 16 at the top of the column 14. The column 14 may include one or more carriages, such as a carriage 17 (alternatively "arm support") for supporting the deployment of one or more robotic arms 12 (three shown in FIG. 2). The carriage 17 may include individually configurable arm mounts that rotate along a perpendicular axis to adjust the base of the robotic arms 12 for better positioning relative to the patient. The carriage 17 also includes a carriage interface 19 that allows the carriage 17 to vertically translate along the column 14.

The carriage interface 19 is connected to the column 14 through slots, such as slot 20, that are positioned on opposite sides of the column 14 to guide the vertical translation of the carriage 17. The slot 20 contains a vertical translation interface to position and hold the carriage 17 at various vertical heights relative to the cart base 15. Vertical translation of the carriage 17 allows the cart 11 to adjust the reach of the robotic arms 12 to meet a variety of table heights, patient sizes, and physician preferences. Similarly, the individually configurable arm mounts on the carriage 17 allow the robotic arm base 21 of the robotic arms 12 to be angled in a variety of configurations.

In some embodiments, the slot 20 may be supplemented with slot covers that are flush and parallel to the slot surface to prevent dirt and fluid ingress into the internal chambers of the column 14 and the vertical translation interface as the carriage 17 vertically translates. The slot covers may be deployed through pairs of spring spools positioned near the vertical top and bottom of the slot 20. The covers are coiled within the spools until deployed to extend and retract from their coiled state as the carriage 17 vertically translates up and down. The spring-loading of the spools provides force to retract the cover into a spool when the carriage 17 translates towards the spool, while also maintaining a tight seal when the carriage 17 translates away from the spool. The covers may be connected to the carriage 17 using, for example, brackets in the carriage interface 19 to ensure proper extension and retraction of the cover as the carriage 17 translates.

The column 14 may internally comprise mechanisms, such as gears and motors, that are designed to use a vertically aligned lead screw to translate the carriage 17 in a mechanized fashion in response to control signals generated in response to user inputs, e.g., inputs from the console 16.

The robotic arms 12 may generally comprise robotic arm bases 21 and end effectors 22, separated by a series of linkages 23 that are connected by a series of joints 24, each joint comprising an independent actuator, each actuator comprising an independently controllable motor. Each independently controllable joint represents an independent degree of freedom available to the robotic arm 12. Each of the robotic arms 12 may have seven joints, and thus provide seven degrees of freedom. A multitude of joints result in a multitude of degrees of freedom, allowing for "redundant" degrees of freedom. Having redundant degrees of freedom allows the robotic arms 12 to position their respective end effectors 22 at a specific position, orientation, and trajectory in space using different linkage positions and joint angles. This allows for the system to position and direct a medical instrument from a desired point in space while allowing the physician to move the arm joints into a clinically advantageous position away from the patient to create greater access, while avoiding arm collisions.

The cart base 15 balances the weight of the column 14, carriage 17, and robotic arms 12 over the floor. Accordingly, the cart base 15 houses heavier components, such as electronics, motors, power supply, as well as components that either enable movement and/or immobilize the cart 11. For example, the cart base 15 includes rollable wheel-shaped casters 25 that allow for the cart 11 to easily move around the room prior to a procedure. After reaching the appropriate position, the casters 25 may be immobilized using wheel locks to hold the cart 11 in place during the procedure.

Positioned at the vertical end of the column 14, the console 16 allows for both a user interface for receiving user input and a display screen (or a dual-purpose device such as, for example, a touchscreen 26) to provide the physician user with both preoperative and intraoperative data. Potential preoperative data on the touchscreen 26 may include preoperative plans, navigation and mapping data derived from preoperative computerized tomography (CT) scans, and/or notes from preoperative patient interviews. Intraoperative data on display may include optical information provided from the tool, sensor and coordinate information from sensors, as well as vital patient statistics, such as respiration, heart rate, and/or pulse. The console 16 may be positioned and tilted to allow a physician to access the console 16 from the side of the column 14 opposite the carriage 17. From this position, the physician may view the console 16, robotic arms 12, and patient while operating the console 16 from behind the cart 11. As shown, the console 16 also includes a handle 27 to assist with maneuvering and stabilizing the cart 11.

Figure 3:
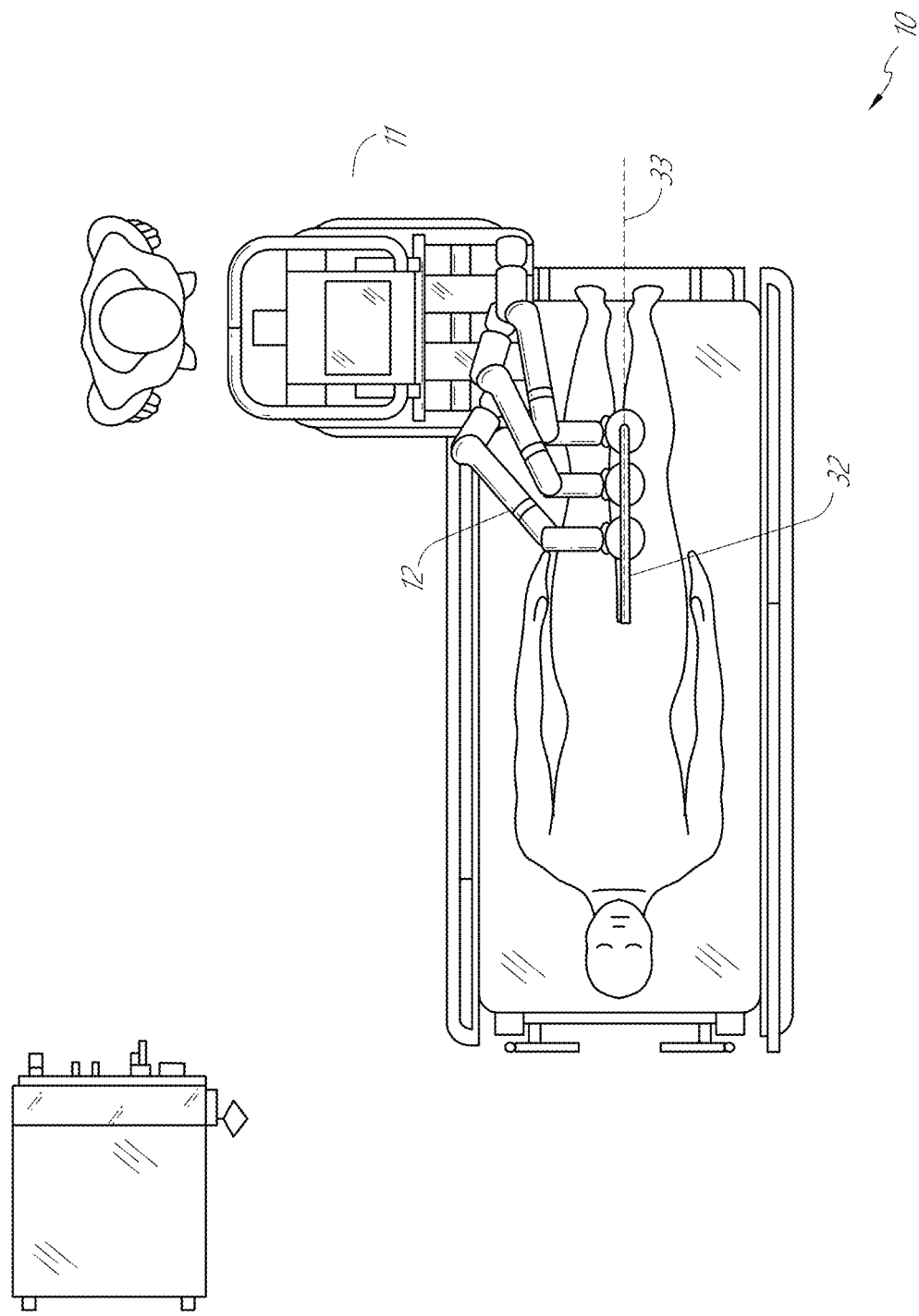
FIG. 3 illustrates an embodiment of the robotic system of FIG. 1 arranged for ureteroscopy.

FIG. 3 illustrates an embodiment of a robotically-enabled system 10 arranged for ureteroscopy. In a ureteroscopic procedure, the cart 11 may be positioned to deliver a ureteroscope 32, a procedure-specific endoscope designed to traverse a patient's urethra and ureter, to the lower abdominal area of the patient. In a ureteroscopy, it may be desirable for the ureteroscope 32 to be directly aligned with the patient's urethra to reduce friction and forces on the sensitive anatomy in the area. As shown, the cart 11 may be aligned at the foot of the table to allow the robotic arms 12 to position the ureteroscope 32 for direct linear access to the patient's urethra. From the foot of the table, the robotic arms 12 may insert the ureteroscope 32 along the virtual rail 33 directly into the patient's lower abdomen through the urethra.

After insertion into the urethra, using similar control techniques as in bronchoscopy, the ureteroscope 32 may be navigated into the bladder, ureters, and/or kidneys for diagnostic and/or therapeutic applications. For example, the ureteroscope 32 may be directed into the ureter and kidneys to break up kidney stone build up using a laser or ultrasonic lithotripsy device deployed down the working channel of the ureteroscope 32. After lithotripsy is complete, the resulting stone fragments may be removed using baskets deployed down the ureteroscope 32.

Figure 4:
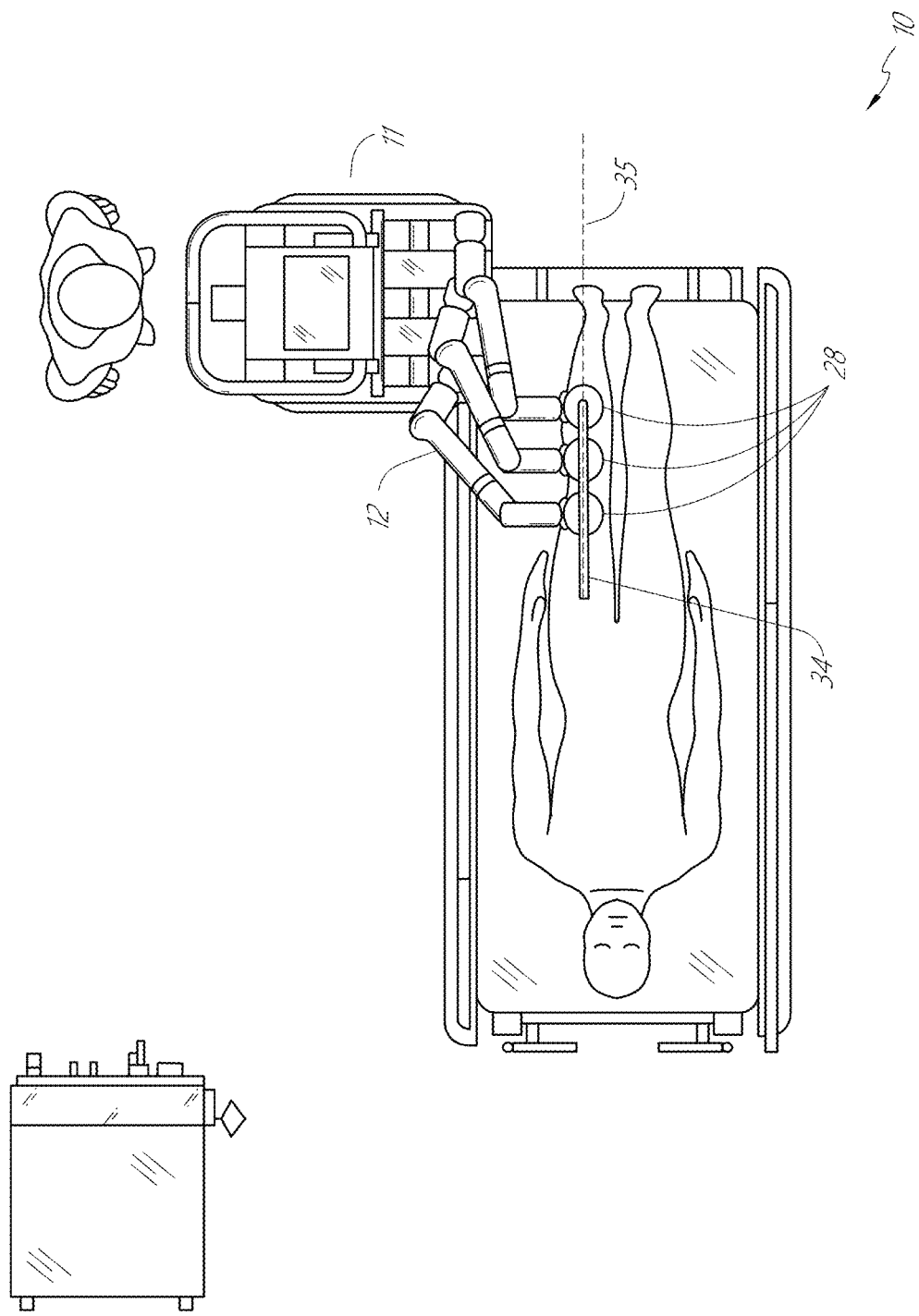
FIG. 4 illustrates an embodiment of the robotic system of FIG. 1 arranged for a vascular procedure.

FIG. 4 illustrates an embodiment of a robotically-enabled system 10 similarly arranged for a vascular procedure. In a vascular procedure, the system 10 may be configured such that the cart 11 may deliver a medical instrument 34, such as a steerable catheter, to an access point in the femoral artery in the patient's leg. The femoral artery presents both a larger diameter for navigation as well as a relatively less circuitous and tortuous path to the patient's heart, which simplifies navigation. As in a ureteroscopic procedure, the cart 11 may be positioned towards the patient's legs and lower abdomen to allow the robotic arms 12 to provide a virtual rail 35 with direct linear access to the femoral artery access point in the patient's thigh/hip region. After insertion into the artery, the medical instrument 34 may be directed and inserted by translating the instrument drivers 28. Alternatively, the cart may be positioned around the patient's upper abdomen in order to reach alternative vascular access points, such as, for example, the carotid and brachial arteries near the shoulder and wrist.

B. Robotic System—Table.

Figure 5:
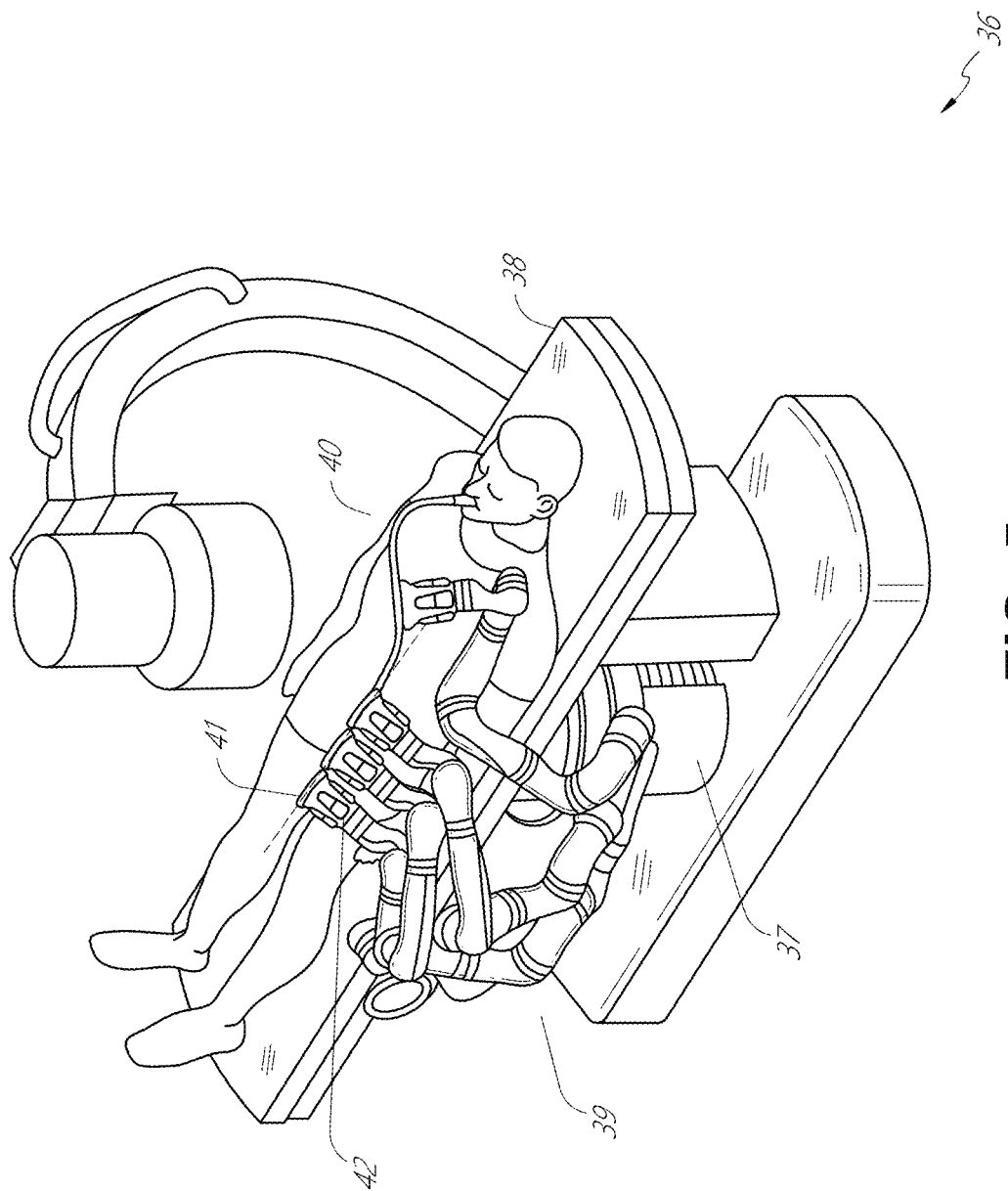
FIG. 5 illustrates an embodiment of a table-based robotic system arranged for a bronchoscopic procedure.

Embodiments of the robotically-enabled medical system may also incorporate the patient's table. Incorporation of the table reduces the amount of capital equipment within the operating room by removing the cart, which allows greater access to the patient. FIG. 5 illustrates an embodiment of such a robotically-enabled system arranged for a bronchoscopic procedure. System 36 includes a support structure or column 37 for supporting platform 38 (shown as a "table" or "bed") over the floor. Much like in the cart-based systems, the end effectors of the robotic arms 39 of the system 36 comprise instrument drivers 42 that are designed to manipulate an elongated medical instrument, such as a bronchoscope 40 in FIG. 5, through or along a virtual rail 41 formed from the linear alignment of the instrument drivers 42. In practice, a C-arm for providing fluoroscopic imaging may be positioned over the patient's upper abdominal area by placing the emitter and detector around the table 38.

Figure 6:
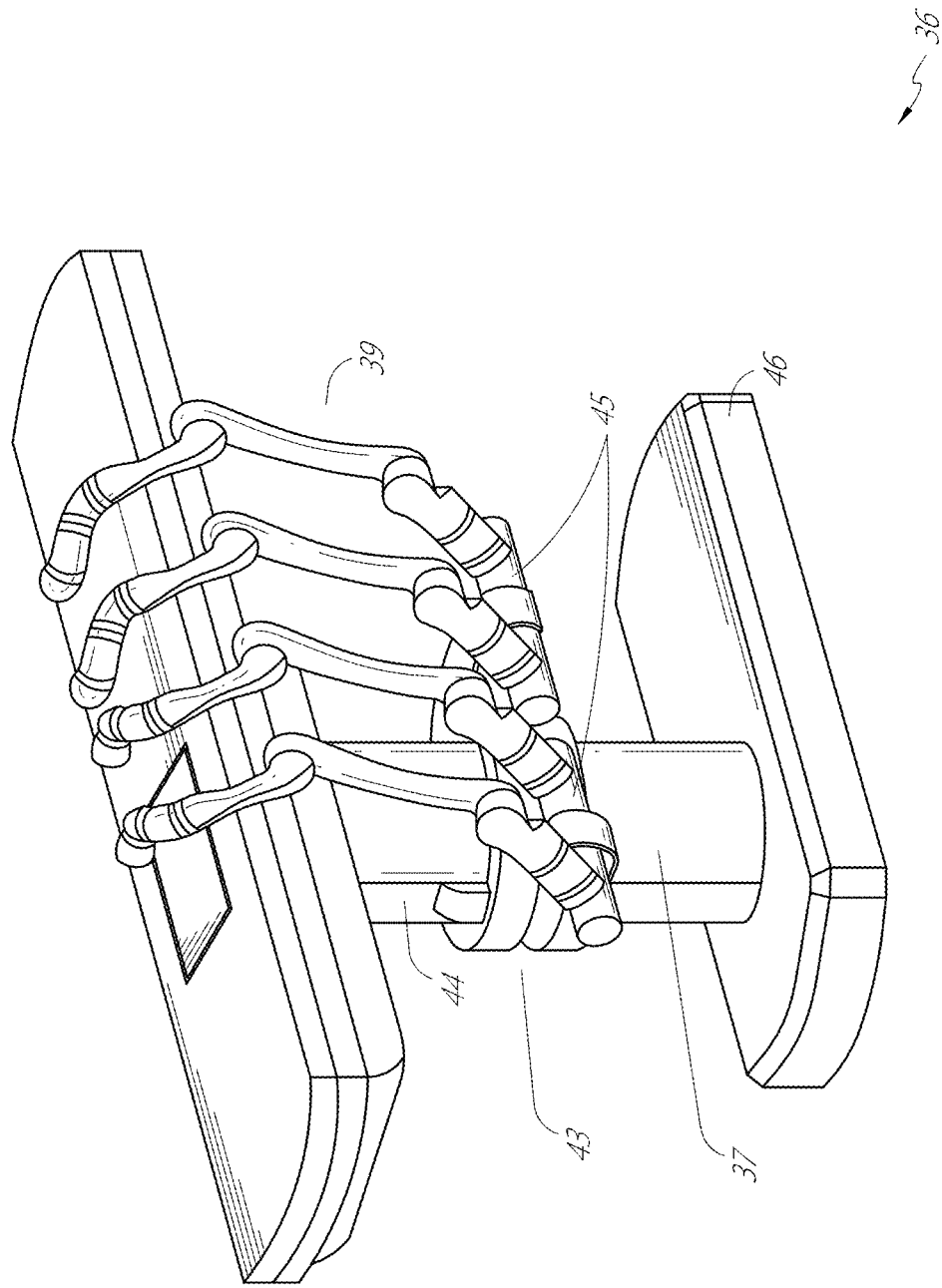
FIG. 6 provides an alternative view of the robotic system of FIG. 5.

FIG. 6 provides an alternative view of the system 36 without the patient and medical instrument for discussion purposes. As shown, the column 37 may include one or more carriages 43 shown as ring-shaped in the system 36, from which the one or more robotic arms 39 may be based. The carriages 43 may translate along a vertical column interface 44 that runs the length of the column 37 to provide different vantage points from which the robotic arms 39 may be positioned to reach the patient. The carriage(s) 43 may rotate around the column 37 using a mechanical motor positioned within the column 37 to allow the robotic arms 39 to have access to multiples sides of the table 38, such as, for example, both sides of the patient. In embodiments with multiple carriages, the carriages may be individually positioned on the column and may translate and/or rotate independently of the other carriages. While the carriages 43 need not surround the column 37 or even be circular, the ring-shape as shown facilitates rotation of the carriages 43 around the column 37 while maintaining structural balance. Rotation and translation of the carriages 43 allows the system 36 to align the medical instruments, such as endoscopes and laparoscopes, into different access points on the patient. In other embodiments (not shown), the system 36 can include a patient table or bed with adjustable arm supports in the form of bars or rails extending alongside it. One or more robotic arms 39 (e.g., via a shoulder with an elbow joint) can be attached to the adjustable arm supports, which can be vertically adjusted. By providing vertical adjustment, the robotic arms 39 are advantageously capable of being stowed compactly beneath the patient table or bed, and subsequently raised during a procedure.

Figure 9:
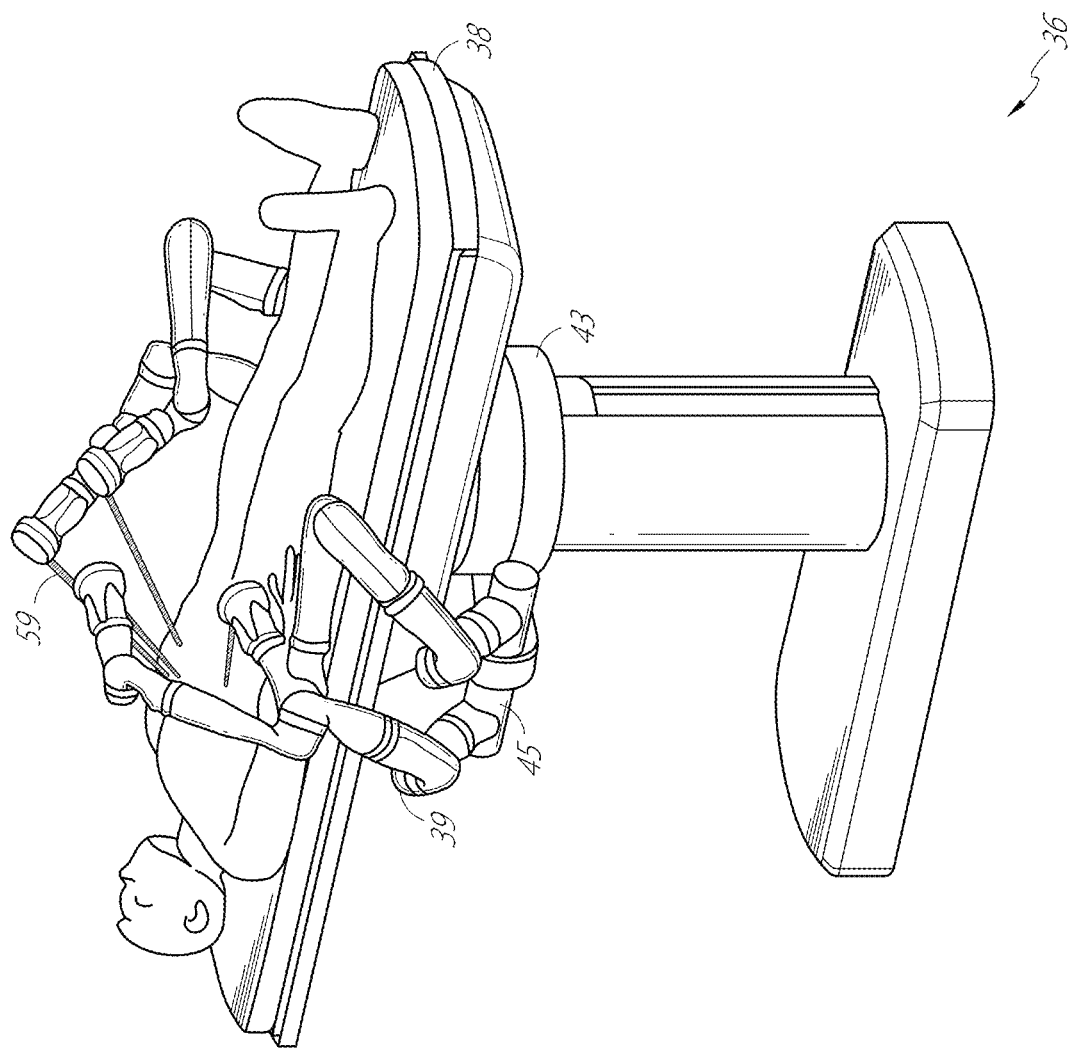
FIG. 9 illustrates an embodiment of a table-based robotic system configured for a laparoscopic procedure.

The robotic arms 39 may be mounted on the carriages 43 through a set of arm mounts 45 comprising a series of joints that may individually rotate and/or telescopically extend to provide additional configurability to the robotic arms 39. Additionally, the arm mounts 45 may be positioned on the carriages 43 such that, when the carriages 43 are appropriately rotated, the arm mounts 45 may be positioned on either the same side of the table 38 (as shown in FIG. 6), on opposite sides of the table 38 (as shown in FIG. 9), or on adjacent sides of the table 38 (not shown).

The column 37 structurally provides support for the table 38, and a path for vertical translation of the carriages 43. Internally, the column 37 may be equipped with lead screws for guiding vertical translation of the carriages, and motors to mechanize the translation of the carriages 43 based the lead screws. The column 37 may also convey power and control signals to the carriages 43 and the robotic arms 39 mounted thereon.

The table base 46 serves a similar function as the cart base 15 in the cart 11 shown in FIG. 2, housing heavier components to balance the table/bed 38, the column 37, the carriages 43, and the robotic arms 39. The table base 46 may also incorporate rigid casters to provide stability during procedures. Deployed from the bottom of the table base 46, the casters may extend in opposite directions on both sides of the base 46 and retract when the system 36 needs to be moved.

With continued reference to FIG. 6, the system 36 may also include a tower (not shown) that divides the functionality of the system 36 between the table and the tower to reduce the form factor and bulk of the table. As in earlier disclosed embodiments, the tower may provide a variety of support functionalities to the table, such as processing, computing, and control capabilities, power, fluidics, and/or optical and sensor processing. The tower may also be movable to be positioned away from the patient to improve physician access and de-clutter the operating room. Additionally, placing components in the tower allows for more storage space in the table base 46 for potential stowage of the robotic arms 39. The tower may also include a master controller or console that provides both a user interface for user input, such as keyboard and/or pendant, as well as a display screen (or touchscreen) for preoperative and intraoperative information, such as real-time imaging, navigation, and tracking information. In some embodiments, the tower may also contain holders for gas tanks to be used for insufflation.

Figure 7:
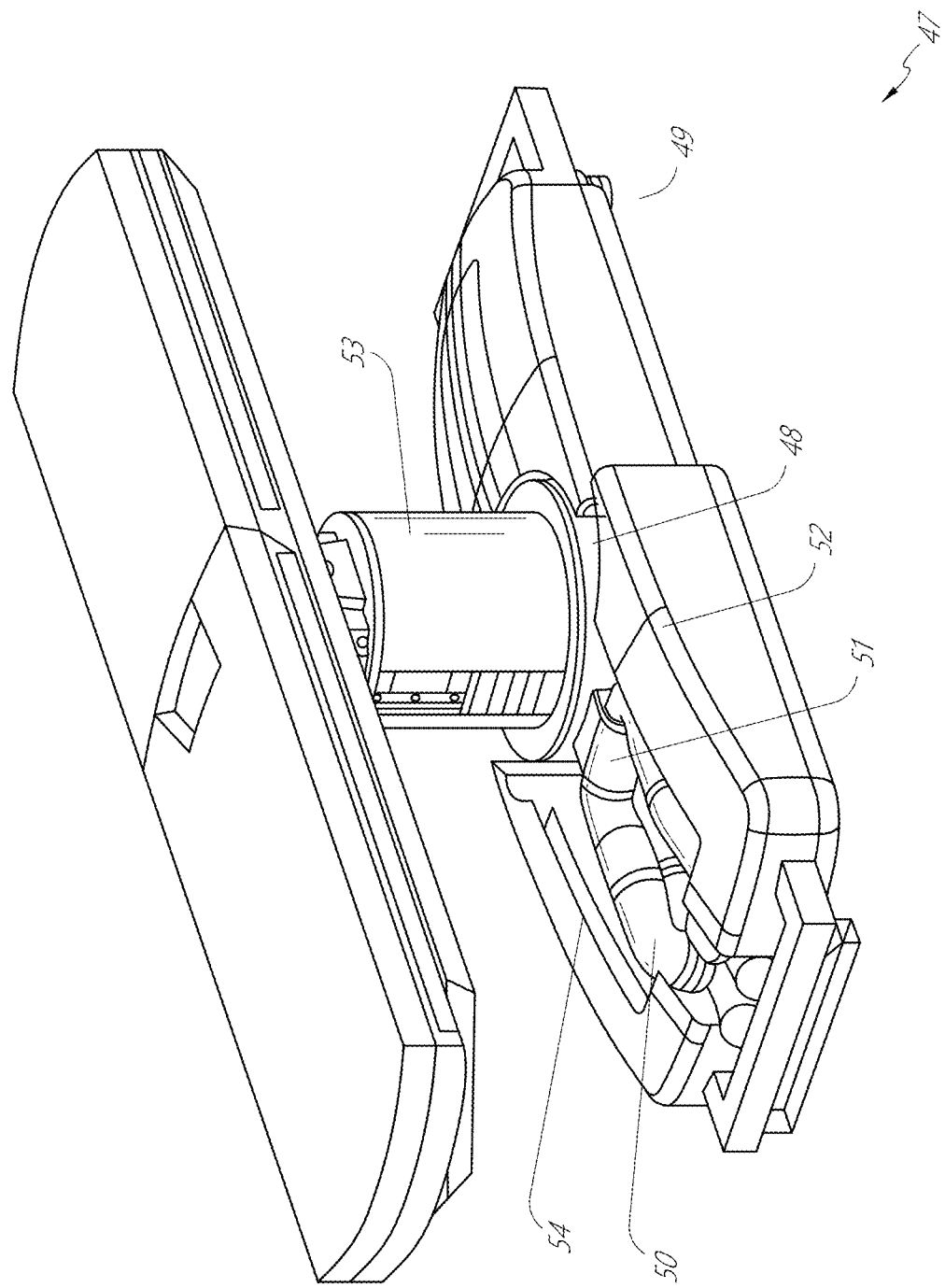
FIG. 7 illustrates an example system configured to stow robotic arm(s).

In some embodiments, a table base may stow and store the robotic arms when not in use. FIG. 7 illustrates a system 47 that stows robotic arms in an embodiment of the table-based system. In the system 47, carriages 48 may be vertically translated into base 49 to stow robotic arms 50, arm mounts 51, and the carriages 48 within the base 49. Base covers 52 may be translated and retracted open to deploy the carriages 48, arm mounts 51, and robotic arms 50 around column 53, and closed to stow to protect them when not in use. The base covers 52 may be sealed with a membrane 54 along the edges of its opening to prevent dirt and fluid ingress when closed.

Figure 8:
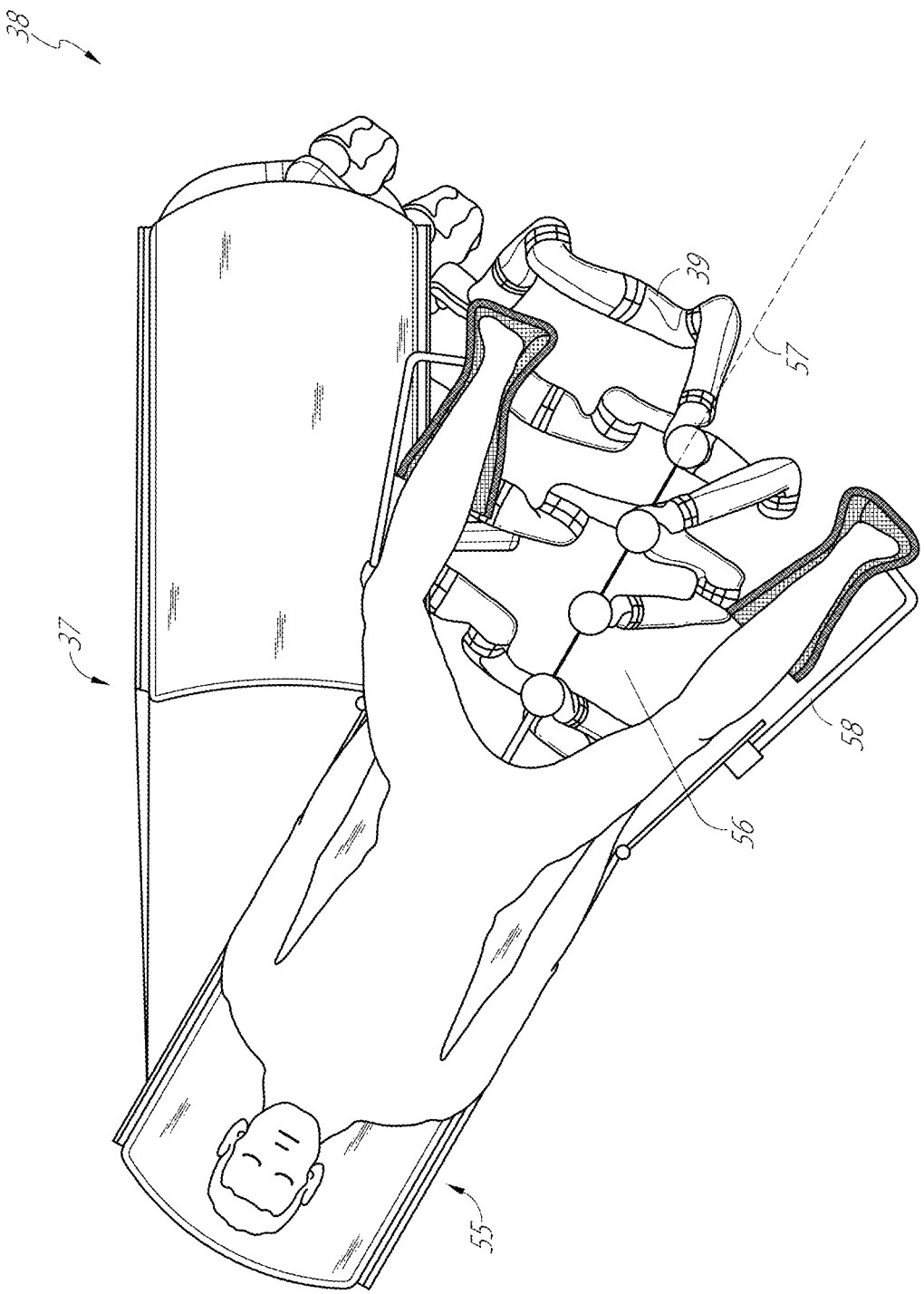
FIG. 8 illustrates an embodiment of a table-based robotic system configured for a ureteroscopic procedure.

FIG. 8 illustrates an embodiment of a robotically-enabled table-based system configured for a ureteroscopic procedure. In a ureteroscopy, the table 38 may include a swivel portion 55 for positioning a patient off-angle from the column 37 and table base 46. The swivel portion 55 may rotate or pivot around a pivot point (e.g., located below the patient's head) in order to position the bottom portion of the swivel portion 55 away from the column 37. For example, the pivoting of the swivel portion 55 allows a C-arm (not shown) to be positioned over the patient's lower abdomen without competing for space with the column (not shown) below table 38. By rotating the carriage 35 (not shown) around the column 37, the robotic arms 39 may directly insert a ureteroscope 56 along a virtual rail 57 into the patient's groin area to reach the urethra. In a ureteroscopy, stirrups 58 may also be fixed to the swivel portion 55 of the table 38 to support the position of the patient's legs during the procedure and allow clear access to the patient's groin area.

In a laparoscopic procedure, through small incision(s) in the patient's abdominal wall, minimally invasive instruments may be inserted into the patient's anatomy. In some embodiments, the minimally invasive instruments comprise an elongated rigid member, such as a shaft, which is used to access anatomy within the patient. After inflation of the patient's abdominal cavity, the instruments may be directed to perform surgical or medical tasks, such as grasping, cutting, ablating, suturing, etc. In some embodiments, the instruments can comprise a scope, such as a laparoscope. FIG. 9 illustrates an embodiment of a robotically-enabled table-based system configured for a laparoscopic procedure. As shown in FIG. 9, the carriages 43 of the system 36 may be rotated and vertically adjusted to position pairs of the robotic arms 39 on opposite sides of the table 38, such that instrument 59 may be positioned using the arm mounts 45 to be passed through minimal incisions on both sides of the patient to reach his/her abdominal cavity.

Figure 10:
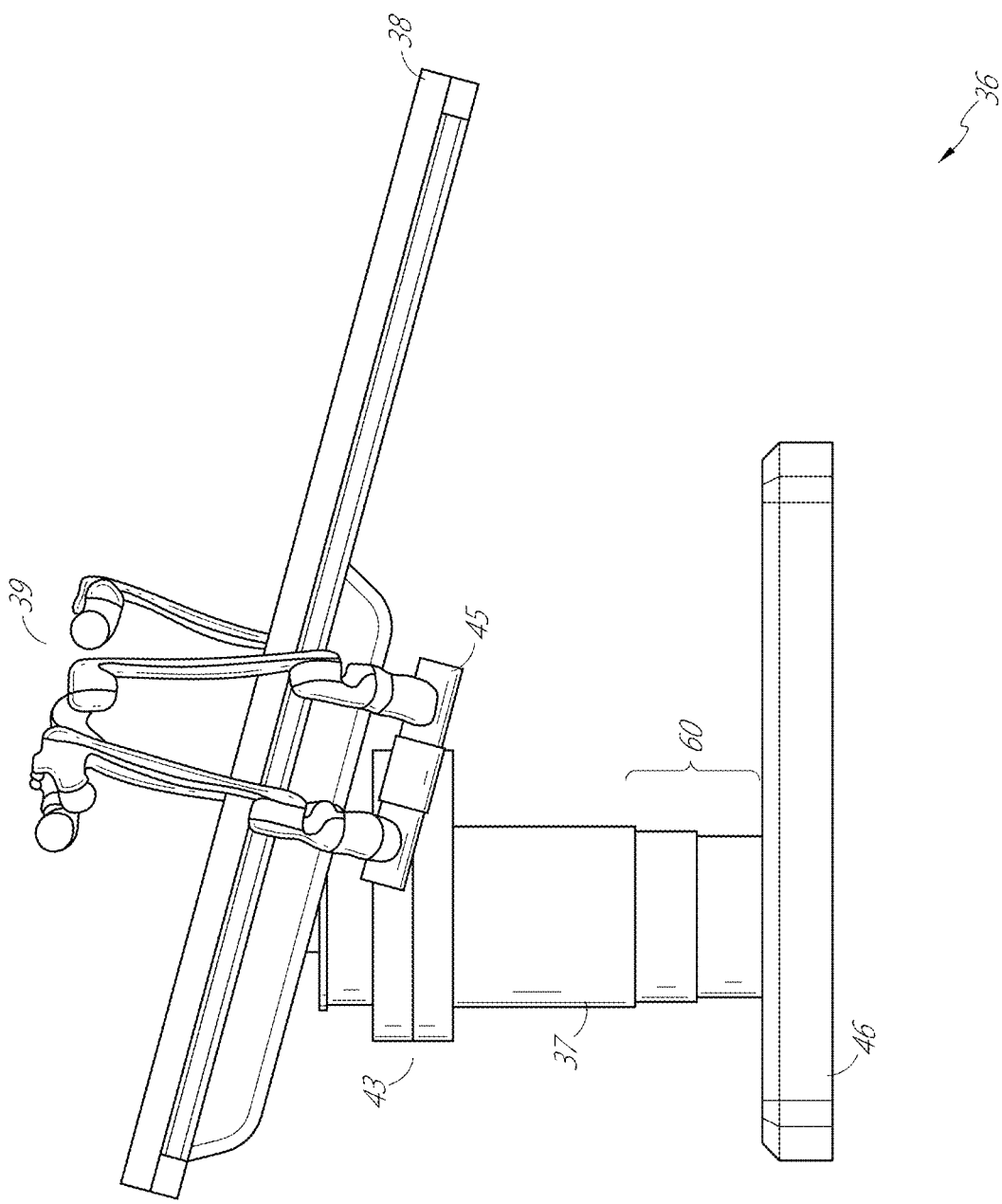
FIG. 10 illustrates an embodiment of the table-based robotic system of FIGS. 5-9 with pitch or tilt adjustment.

To accommodate laparoscopic procedures, the robotically-enabled table system may also tilt the platform to a desired angle. FIG. 10 illustrates an embodiment of the robotically-enabled medical system with pitch or tilt adjustment. As shown in FIG. 10, the system 36 may accommodate tilt of the table 38 to position one portion of the table at a greater distance from the floor than the other. Additionally, the arm mounts 45 may rotate to match the tilt such that the robotic arms 39 maintain the same planar relationship with the table 38. To accommodate steeper angles, the column 37 may also include telescoping portions 60 that allow vertical extension of the column 37 to keep the table 38 from touching the floor or colliding with the table base 46.

Figure 11:
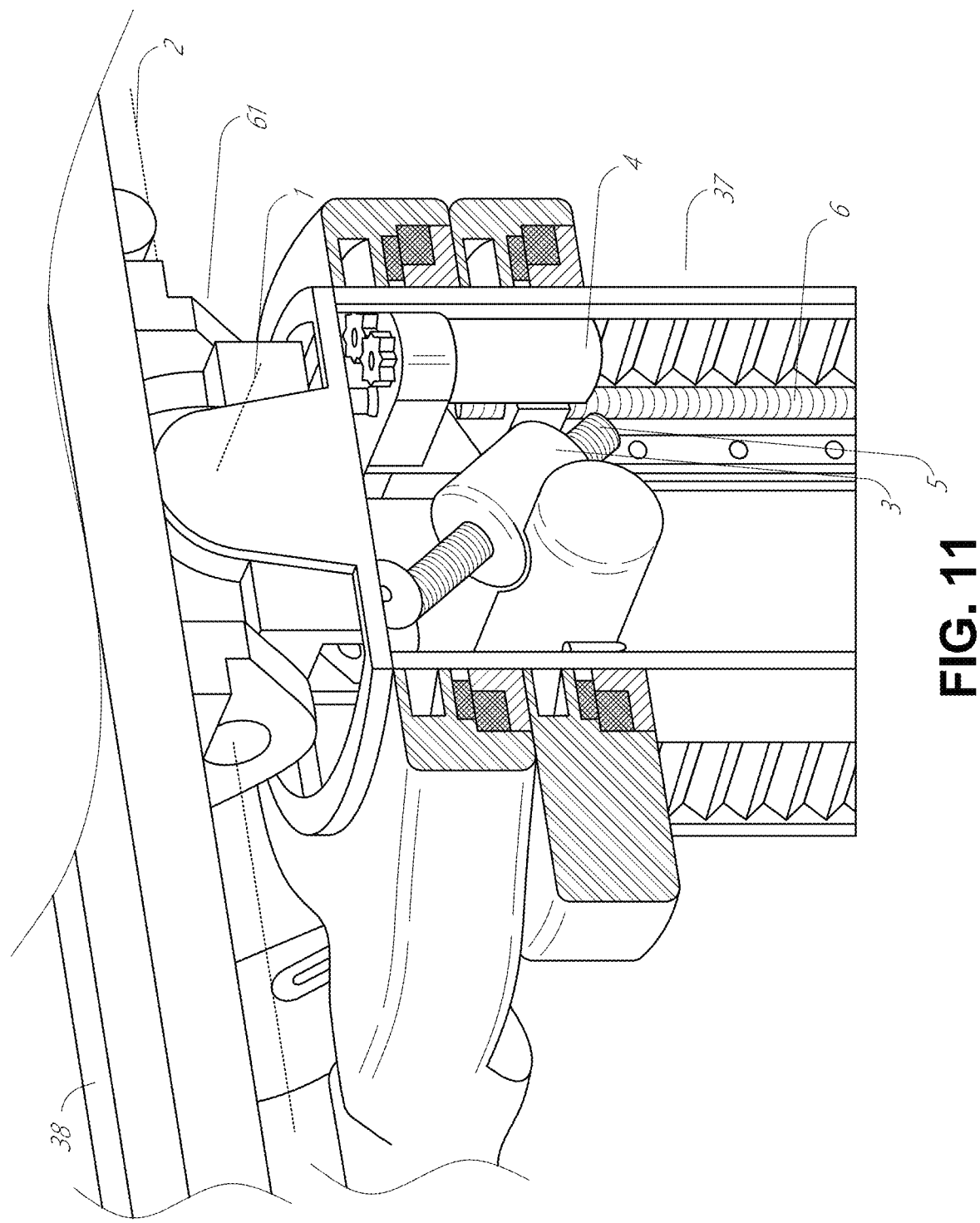
FIG. 11 provides a detailed illustration of the interface between the table and the column of the table-based robotic system of FIGS. 5-10.

FIG. 11 provides a detailed illustration of the interface between the table 38 and the column 37. Pitch rotation mechanism 61 may be configured to alter the pitch angle of the table 38 relative to the column 37 in multiple degrees of freedom. The pitch rotation mechanism 61 may be enabled by the positioning of orthogonal axes 1, 2 at the column-table interface, each axis actuated by a separate motor 3, 4 responsive to an electrical pitch angle command. Rotation along one screw 5 would enable tilt adjustments in one axis 1, while rotation along the other screw 6 would enable tilt adjustments along the other axis 2. In some embodiments, a ball joint can be used to alter the pitch angle of the table 38 relative to the column 37 in multiple degrees of freedom.

For example, pitch adjustments are particularly useful when trying to position the table in a Trendelenburg position, i.e., position the patient's lower abdomen at a higher position from the floor than the patient's upper abdomen, for lower abdominal surgery. The Trendelenburg position causes the patient's internal organs to slide towards his/her upper abdomen through the force of gravity, clearing out the abdominal cavity for minimally invasive tools to enter and perform lower abdominal surgical or medical procedures, such as laparoscopic prostatectomy.

Figure 12:
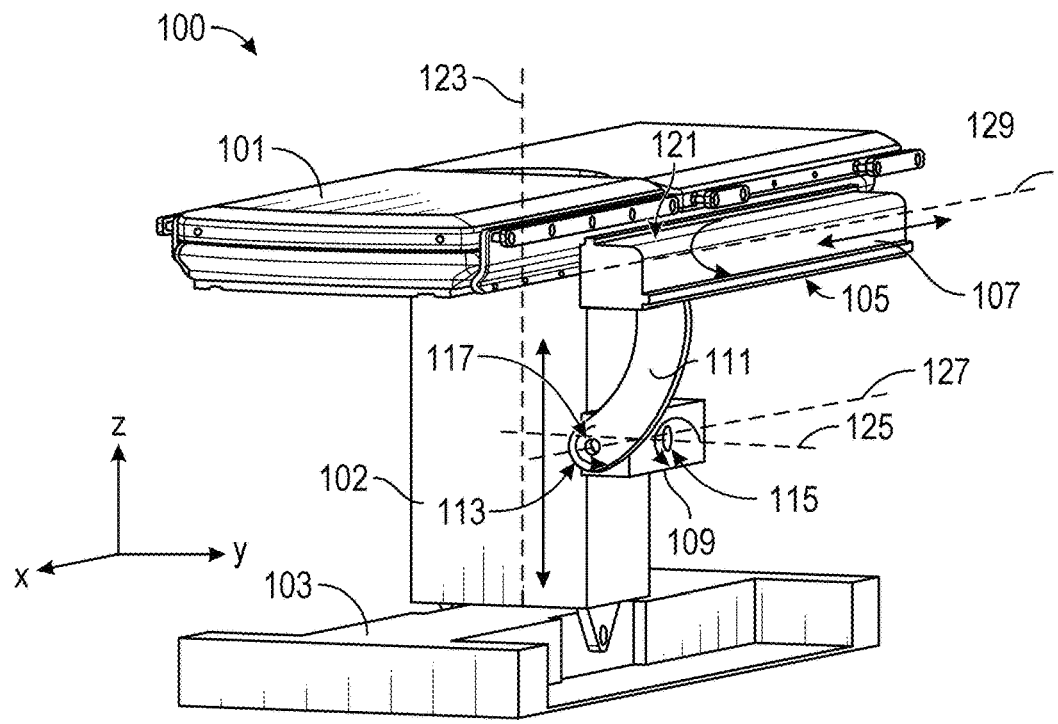
FIG. 12 illustrates an alternative embodiment of a table-based robotic system.
Figure 13:
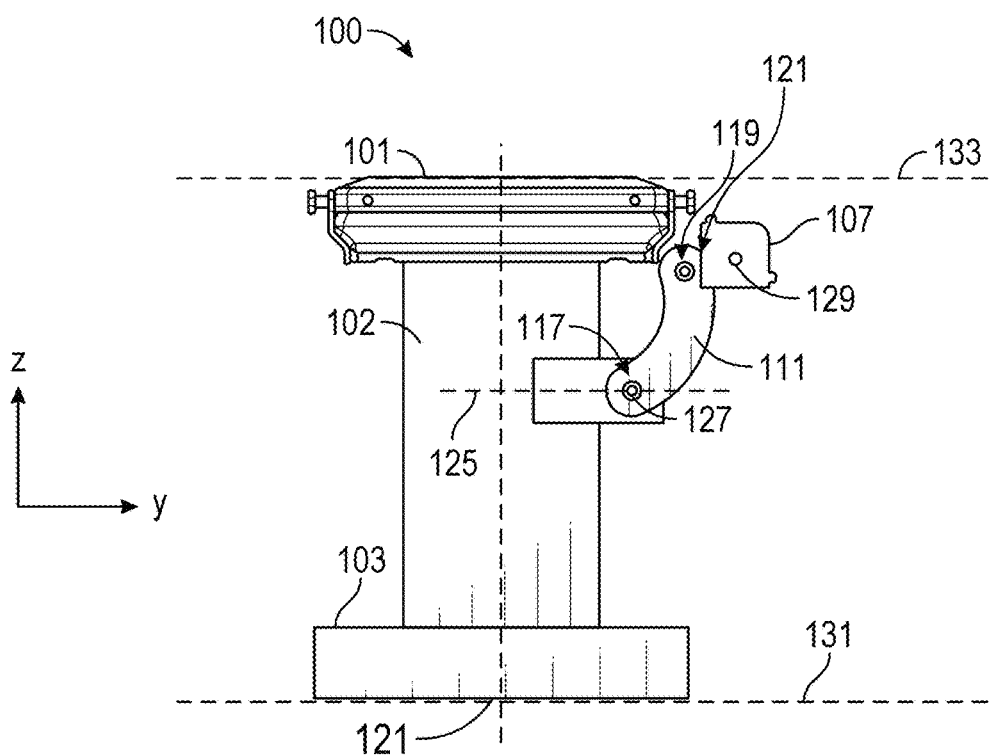
FIG. 13 illustrates an end view of the table-based robotic system of FIG. 12.

FIGS. 12 and 13 illustrate isometric and end views of an alternative embodiment of a table-based surgical robotics system 100. The surgical robotics system 100 includes one or more adjustable arm supports 105 that can be configured to support one or more robotic arms (see, for example, FIG. 14) relative to a table 101. In the illustrated embodiment, a single adjustable arm support 105 is shown, though an additional arm support can be provided on an opposite side of the table 101. The adjustable arm support 105 can be configured so that it can move relative to the table 101 to adjust and/or vary the position of the adjustable arm support 105 and/or any robotic arms mounted thereto relative to the table 101. For example, the adjustable arm support 105 may be adjusted one or more degrees of freedom relative to the table 101. The adjustable arm support 105 provides high versatility to the system 100, including the ability to easily stow the one or more adjustable arm supports 105 and any robotics arms attached thereto beneath the table 101. The adjustable arm support 105 can be elevated from the stowed position to a position below an upper surface of the table 101. In other embodiments, the adjustable arm support 105 can be elevated from the stowed position to a position above an upper surface of the table 101.

The adjustable arm support 105 can provide several degrees of freedom, including lift, lateral translation, tilt, etc. In the illustrated embodiment of FIGS. 12 and 13, the arm support 105 is configured with four degrees of freedom, which are illustrated with arrows in FIG. 12. A first degree of freedom allows for adjustment of the adjustable arm support 105 in the z-direction ("Z-lift"). For example, the adjustable arm support 105 can include a carriage 109 configured to move up or down along or relative to a column 102 supporting the table 101. A second degree of freedom can allow the adjustable arm support 105 to tilt. For example, the adjustable arm support 105 can include a rotary joint, which can allow the adjustable arm support 105 to be aligned with the bed in a Trendelenburg position. A third degree of freedom can allow the adjustable arm support 105 to "pivot up," which can be used to adjust a distance between a side of the table 101 and the adjustable arm support 105. A fourth degree of freedom can permit translation of the adjustable arm support 105 along a longitudinal length of the table.

The surgical robotics system 100 in FIGS. 12 and 13 can comprise a table supported by a column 102 that is mounted to a base 103. The base 103 and the column 102 support the table 101 relative to a support surface. A floor axis 131 and a support axis 133 are shown in FIG. 13.

The adjustable arm support 105 can be mounted to the column 102. In other embodiments, the arm support 105 can be mounted to the table 101 or base 103. The adjustable arm support 105 can include a carriage 109, a bar or rail connector 111 and a bar or rail 107. In some embodiments, one or more robotic arms mounted to the rail 107 can translate and move relative to one another.

The carriage 109 can be attached to the column 102 by a first joint 113, which allows the carriage 109 to move relative to the column 102 (e.g., such as up and down a first or vertical axis 123). The first joint 113 can provide the first degree of freedom ("Z-lift") to the adjustable arm support 105. The adjustable arm support 105 can include a second joint 115, which provides the second degree of freedom (tilt) for the adjustable arm support 105. The adjustable arm support 105 can include a third joint 117, which can provide the third degree of freedom ("pivot up") for the adjustable arm support 105. An additional joint 119 (shown in FIG. 13) can be provided that mechanically constrains the third joint 117 to maintain an orientation of the rail 107 as the rail connector 111 is rotated about a third axis 127. The adjustable arm support 105 can include a fourth joint 121, which can provide a fourth degree of freedom (translation) for the adjustable arm support 105 along a fourth axis 129.

Figure 14:
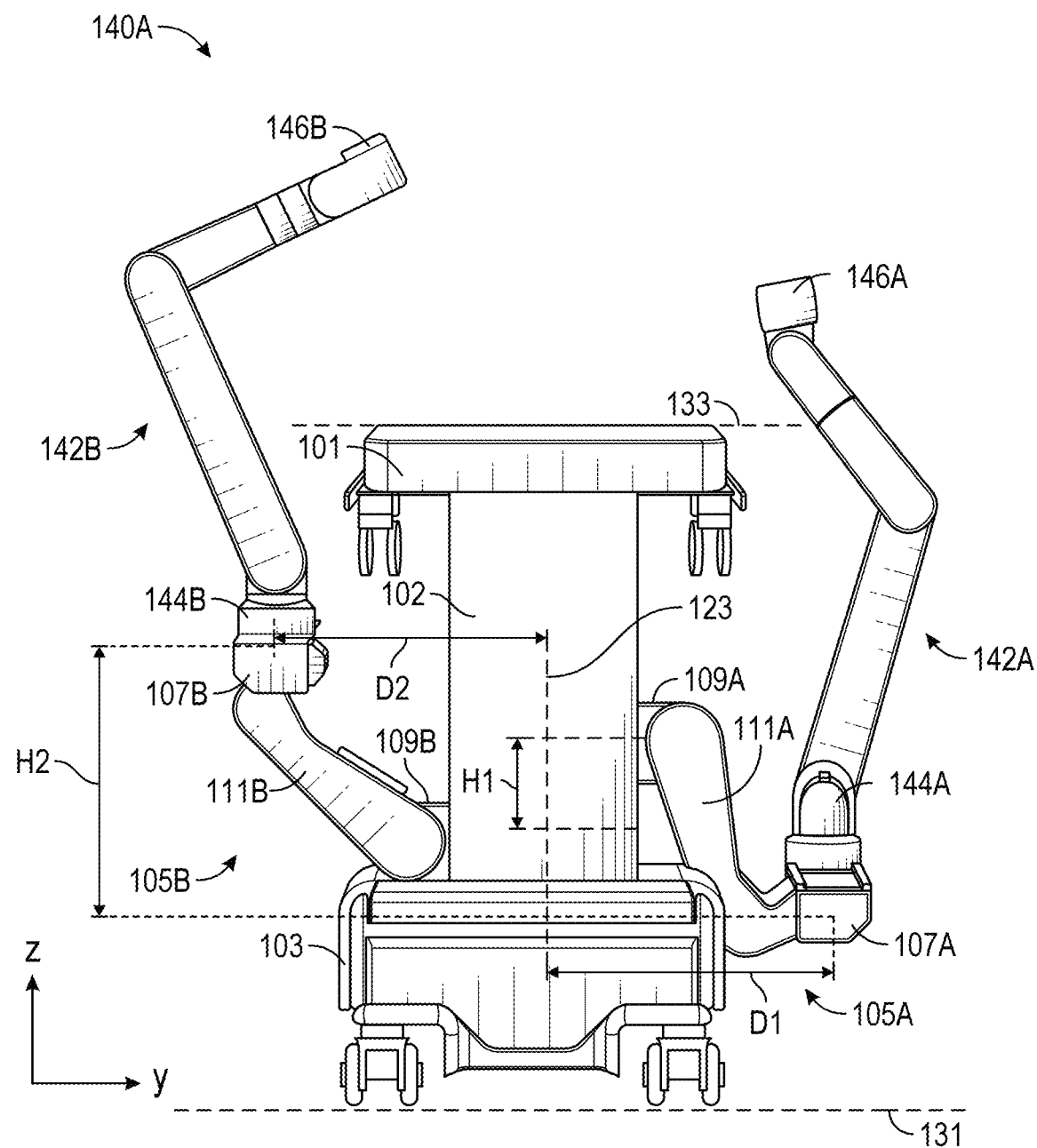
FIG. 14 illustrates an end view of a table-based robotic system with robotic arms attached thereto.

FIG. 14 illustrates an end view of the surgical robotics system 140A with two adjustable arm supports 105A, 105B mounted on opposite sides of a table 101. A first robotic arm 142A is attached to the bar or rail 107A of the first adjustable arm support 105B. The first robotic arm 142A includes a base 144A attached to the rail 107A. The distal end of the first robotic arm 142A includes an instrument drive mechanism 146A that can attach to one or more robotic medical instruments or tools. Similarly, the second robotic arm 142B includes a base 144B attached to the rail 107B. The distal end of the second robotic arm 142B includes an instrument drive mechanism 146B. The instrument drive mechanism 146B can be configured to attach to one or more robotic medical instruments or tools.

In some embodiments, one or more of the robotic arms 142A, 142B comprises an arm with seven or more degrees of freedom. In some embodiments, one or more of the robotic arms 142A, 142B can include eight degrees of freedom, including an insertion axis (1-degree of freedom including insertion), a wrist (3-degrees of freedom including wrist pitch, yaw and roll), an elbow (1-degree of freedom including elbow pitch), a shoulder (2-degrees of freedom including shoulder pitch and yaw), and base 144A, 144B (1-degree of freedom including translation). In some embodiments, the insertion degree of freedom can be provided by the robotic arm 142A, 142B, while in other embodiments, the instrument itself provides insertion via an instrument-based insertion architecture.

C. Instrument Driver & Interface.

The end effectors of the system's robotic arms may comprise (i) an instrument driver (alternatively referred to as "instrument drive mechanism" or "instrument device manipulator") that incorporates electro-mechanical means for actuating the medical instrument and (ii) a removable or detachable medical instrument, which may be devoid of any electro-mechanical components, such as motors. This dichotomy may be driven by the need to sterilize medical instruments used in medical procedures, and the inability to adequately sterilize expensive capital equipment due to their intricate mechanical assemblies and sensitive electronics. Accordingly, the medical instruments may be designed to be detached, removed, and interchanged from the instrument driver (and thus the system) for individual sterilization or disposal by the physician or the physician's staff. In contrast, the instrument drivers need not be changed or sterilized, and may be draped for protection.

Figure 15:
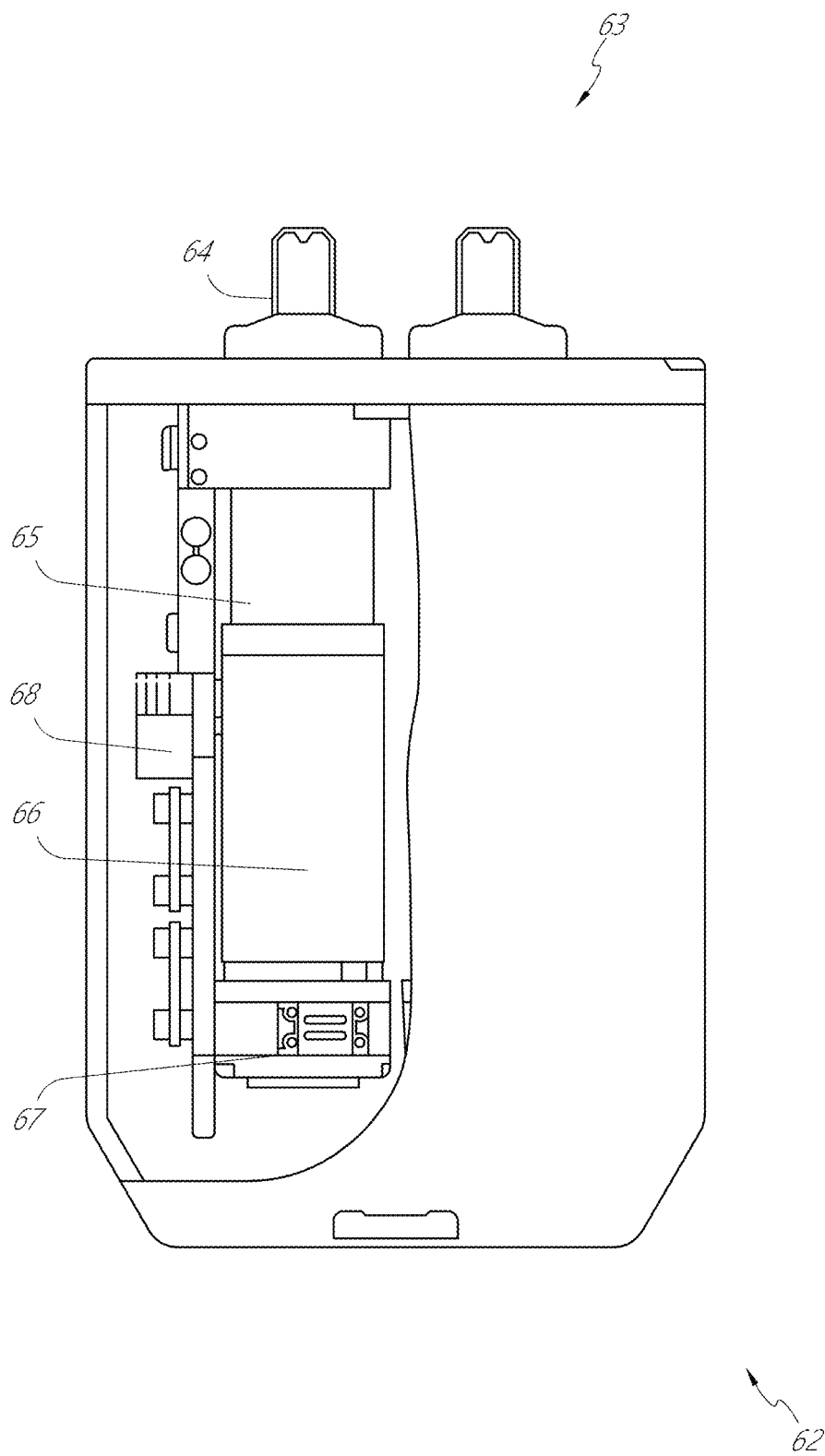
FIG. 15 illustrates an exemplary instrument driver.

FIG. 15 illustrates an example instrument driver. Positioned at the distal end of a robotic arm, instrument driver 62 comprises one or more drive units 63 arranged with parallel axes to provide controlled torque to a medical instrument via drive shafts 64. Each drive unit 63 comprises an individual drive shaft 64 for interacting with the instrument, a gear head 65 for converting the motor shaft rotation to a desired torque, a motor 66 for generating the drive torque, an encoder 67 to measure the speed of the motor shaft and provide feedback to the control circuitry, and control circuitry 68 for receiving control signals and actuating the drive unit. Each drive unit 63 being independently controlled and motorized, the instrument driver 62 may provide multiple (e.g., four as shown in FIG. 15) independent drive outputs to the medical instrument. In operation, the control circuitry 68 would receive a control signal, transmit a motor signal to the motor 66, compare the resulting motor speed as measured by the encoder 67 with the desired speed, and modulate the motor signal to generate the desired torque.

For procedures that require a sterile environment, the robotic system may incorporate a drive interface, such as a sterile adapter connected to a sterile drape, that sits between the instrument driver and the medical instrument. The chief purpose of the sterile adapter is to transfer angular motion from the drive shafts of the instrument driver to the drive inputs of the instrument while maintaining physical separation, and thus sterility, between the drive shafts and drive inputs. Accordingly, an example sterile adapter may comprise a series of rotational inputs and outputs intended to be mated with the drive shafts of the instrument driver and drive inputs on the instrument. Connected to the sterile adapter, the sterile drape, comprised of a thin, flexible material such as transparent or translucent plastic, is designed to cover the capital equipment, such as the instrument driver, robotic arm, and cart (in a cart-based system) or table (in a table-based system). Use of the drape would allow the capital equipment to be positioned proximate to the patient while still being located in an area not requiring sterilization (i.e., non-sterile field). On the other side of the sterile drape, the medical instrument may interface with the patient in an area requiring sterilization (i.e., sterile field).

D. Medical Instrument.

Figure 16:
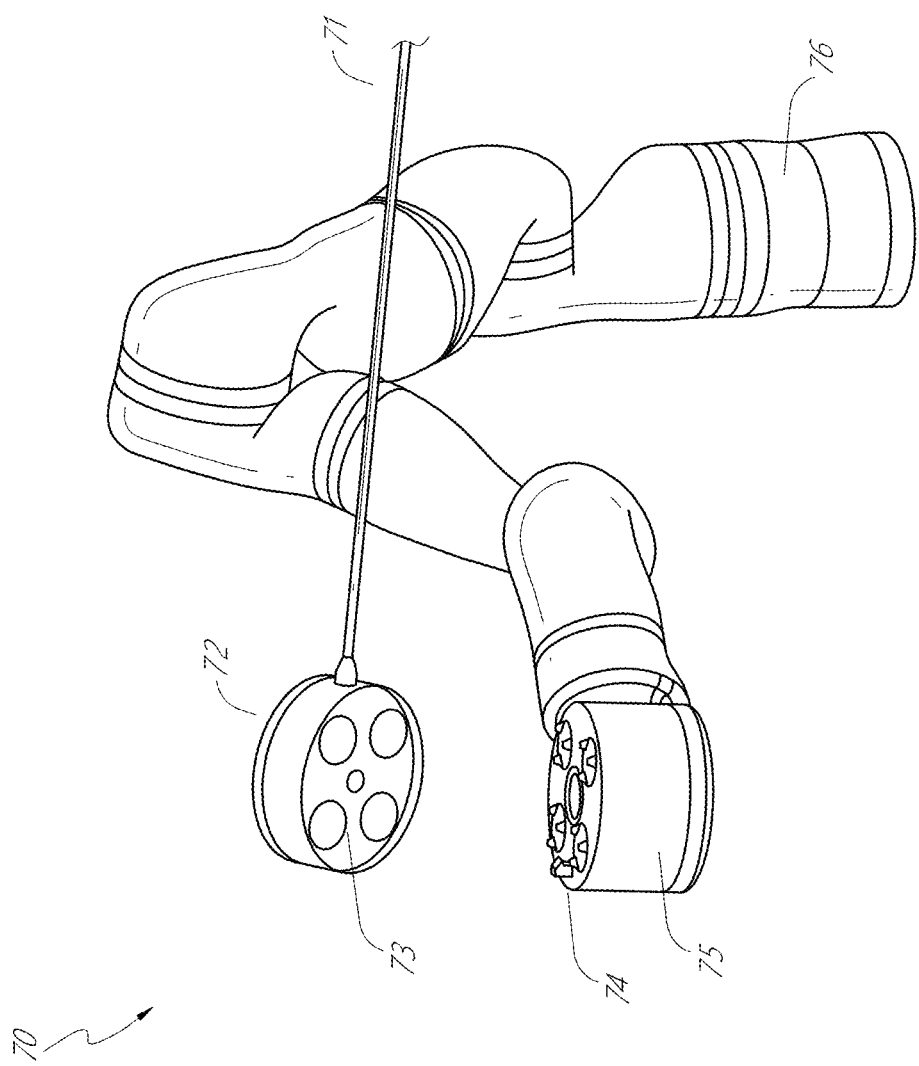
FIG. 16 illustrates an exemplary medical instrument with a paired instrument driver.

FIG. 16 illustrates an example medical instrument with a paired instrument driver. Like other instruments designed for use with a robotic system, medical instrument 70 comprises an elongated shaft 71 (or elongate body) and an instrument base 72. The instrument base 72, also referred to as an "instrument handle" due to its intended design for manual interaction by the physician, may generally comprise rotatable drive inputs 73, e.g., receptacles, pulleys or spools, that are designed to be mated with drive outputs 74 that extend through a drive interface on instrument driver 75 at the distal end of robotic arm 76. When physically connected, latched, and/or coupled, the mated drive inputs 73 of the instrument base 72 may share axes of rotation with the drive outputs 74 in the instrument driver 75 to allow the transfer of torque from the drive outputs 74 to the drive inputs 73. In some embodiments, the drive outputs 74 may comprise splines that are designed to mate with receptacles on the drive inputs 73.

The elongated shaft 71 is designed to be delivered through either an anatomical opening or lumen, e.g., as in endoscopy, or a minimally invasive incision, e.g., as in laparoscopy. The elongated shaft 71 may be either flexible (e.g., having properties similar to an endoscope) or rigid (e.g., having properties similar to a laparoscope) or contain a customized combination of both flexible and rigid portions. When designed for laparoscopy, the distal end of a rigid elongated shaft may be connected to an end effector extending from a jointed wrist formed from a clevis with at least one degree of freedom and a surgical tool or medical instrument, such as, for example, a grasper or scissors, that may be actuated based on force from the tendons as the drive inputs rotate in response to torque received from the drive outputs 74 of the instrument driver 75. When designed for endoscopy, the distal end of a flexible elongated shaft may include a steerable or controllable bending section that may be articulated and bent based on torque received from the drive outputs 74 of the instrument driver 75.

Torque from the instrument driver 75 is transmitted down the elongated shaft 71 using tendons along the elongated shaft 71. These individual tendons, such as pull wires, may be individually anchored to individual drive inputs 73 within the instrument handle 72. From the handle 72, the tendons are directed down one or more pull lumens along the elongated shaft 71 and anchored at the distal portion of the elongated shaft 71, or in the wrist at the distal portion of the elongated shaft. During a surgical procedure, such as a laparoscopic, endoscopic or hybrid procedure, these tendons may be coupled to a distally mounted end effector, such as a wrist, grasper, or scissor. Under such an arrangement, torque exerted on drive inputs 73 would transfer tension to the tendon, thereby causing the end effector to actuate in some way. In some embodiments, during a surgical procedure, the tendon may cause a joint to rotate about an axis, thereby causing the end effector to move in one direction or another. Alternatively, the tendon may be connected to one or more jaws of a grasper at the distal end of the elongated shaft 71, where tension from the tendon causes the grasper to close.

In endoscopy, the tendons may be coupled to a bending or articulating section positioned along the elongated shaft 71 (e.g., at the distal end) via adhesive, control ring, or other mechanical fixation. When fixedly attached to the distal end of a bending section, torque exerted on the drive inputs 73 would be transmitted down the tendons, causing the softer, bending section (sometimes referred to as the articulable section or region) to bend or articulate. Along the non-bending sections, it may be advantageous to spiral or helix the individual pull lumens that direct the individual tendons along (or inside) the walls of the endoscope shaft to balance the radial forces that result from tension in the pull wires. The angle of the spiraling and/or spacing therebetween may be altered or engineered for specific purposes, wherein tighter spiraling exhibits lesser shaft compression under load forces, while lower amounts of spiraling results in greater shaft compression under load forces, but limits bending. On the other end of the spectrum, the pull lumens may be directed parallel to the longitudinal axis of the elongated shaft 71 to allow for controlled articulation in the desired bending or articulable sections.

In endoscopy, the elongated shaft 71 houses a number of components to assist with the robotic procedure. The shaft 71 may comprise a working channel for deploying surgical tools (or medical instruments), irrigation, and/or aspiration to the operative region at the distal end of the shaft 71. The shaft 71 may also accommodate wires and/or optical fibers to transfer signals to/from an optical assembly at the distal tip, which may include an optical camera. The shaft 71 may also accommodate optical fibers to carry light from proximally-located light sources, such as light emitting diodes, to the distal end of the shaft 71.

At the distal end of the instrument 70, the distal tip may also comprise the opening of a working channel for delivering tools for diagnostic and/or therapy, irrigation, and aspiration to an operative site. The distal tip may also include a port for a camera, such as a fiberscope or a digital camera, to capture images of an internal anatomical space. Relatedly, the distal tip may also include ports for light sources for illuminating the anatomical space when using the camera.

In the example of FIG. 16, the drive shaft axes, and thus the drive input axes, are orthogonal to the axis of the elongated shaft 71. This arrangement, however, complicates roll capabilities for the elongated shaft 71. Rolling the elongated shaft 71 along its axis while keeping the drive inputs 73 static results in undesirable tangling of the tendons as they extend off the drive inputs 73 and enter pull lumens within the elongated shaft 71. The resulting entanglement of such tendons may disrupt any control algorithms intended to predict movement of the flexible elongated shaft 71 during an endoscopic procedure.

Figure 17:
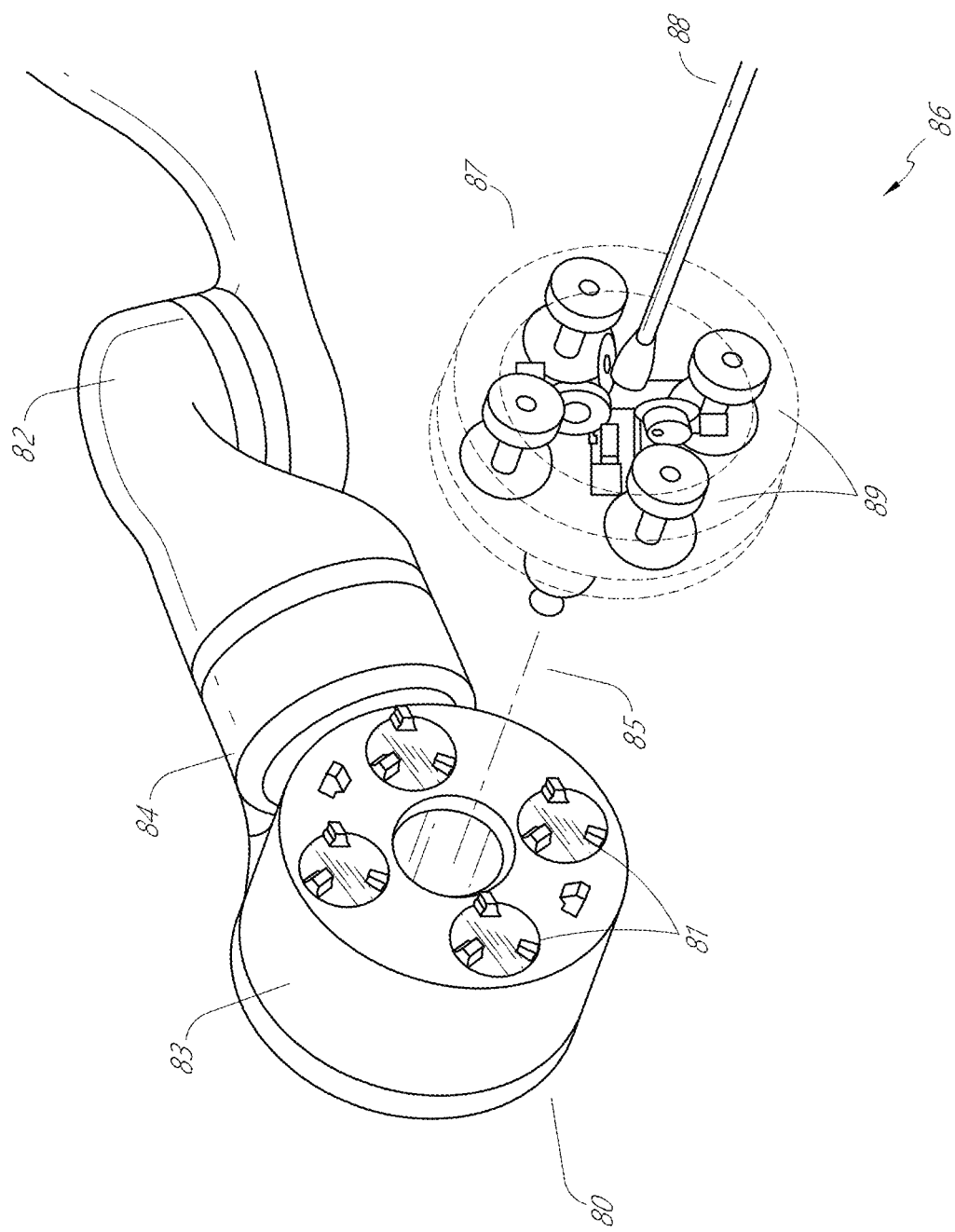
FIG. 17 illustrates an alternative design for an instrument driver and instrument where the axes of the drive units are parallel to the axis of the elongated shaft of the instrument.

FIG. 17 illustrates an alternative design for an instrument driver and instrument where the axes of the drive units are parallel to the axis of the elongated shaft of the instrument. As shown, a circular instrument driver 80 comprises four drive units with their drive outputs 81 aligned in parallel at the end of a robotic arm 82. The drive units, and their respective drive outputs 81, are housed in a rotational assembly 83 of the instrument driver 80 that is driven by one of the drive units within the assembly 83. In response to torque provided by the rotational drive unit, the rotational assembly 83 rotates along a circular bearing that connects the rotational assembly 83 to the non-rotational portion 84 of the instrument driver 80. Power and controls signals may be communicated from the non-rotational portion 84 of the instrument driver 80 to the rotational assembly 83 through electrical contacts that may be maintained through rotation by a brushed slip ring connection (not shown). In other embodiments, the rotational assembly 83 may be responsive to a separate drive unit that is integrated into the non-rotatable portion 84, and thus not in parallel to the other drive units. The rotational mechanism 83 allows the instrument driver 80 to rotate the drive units, and their respective drive outputs 81, as a single unit around an instrument driver axis 85.

Like earlier disclosed embodiments, an instrument 86 may comprise an elongated shaft portion 88 and an instrument base 87 (shown with a transparent external skin for discussion purposes) comprising a plurality of drive inputs 89 (such as receptacles, pulleys, and spools) that are configured to receive the drive outputs 81 in the instrument driver 80. Unlike prior disclosed embodiments, the instrument shaft 88 extends from the center of the instrument base 87 with an axis substantially parallel to the axes of the drive inputs 89, rather than orthogonal as in the design of FIG. 16.

When coupled to the rotational assembly 83 of the instrument driver 80, the medical instrument 86, comprising instrument base 87 and instrument shaft 88, rotates in combination with the rotational assembly 83 about the instrument driver axis 85. Since the instrument shaft 88 is positioned at the center of instrument base 87, the instrument shaft 88 is coaxial with instrument driver axis 85 when attached. Thus, rotation of the rotational assembly 83 causes the instrument shaft 88 to rotate about its own longitudinal axis. Moreover, as the instrument base 87 rotates with the instrument shaft 88, any tendons connected to the drive inputs 89 in the instrument base 87 are not tangled during rotation. Accordingly, the parallelism of the axes of the drive outputs 81, drive inputs 89, and instrument shaft 88 allows for the shaft rotation without tangling any control tendons.

Figure 18:
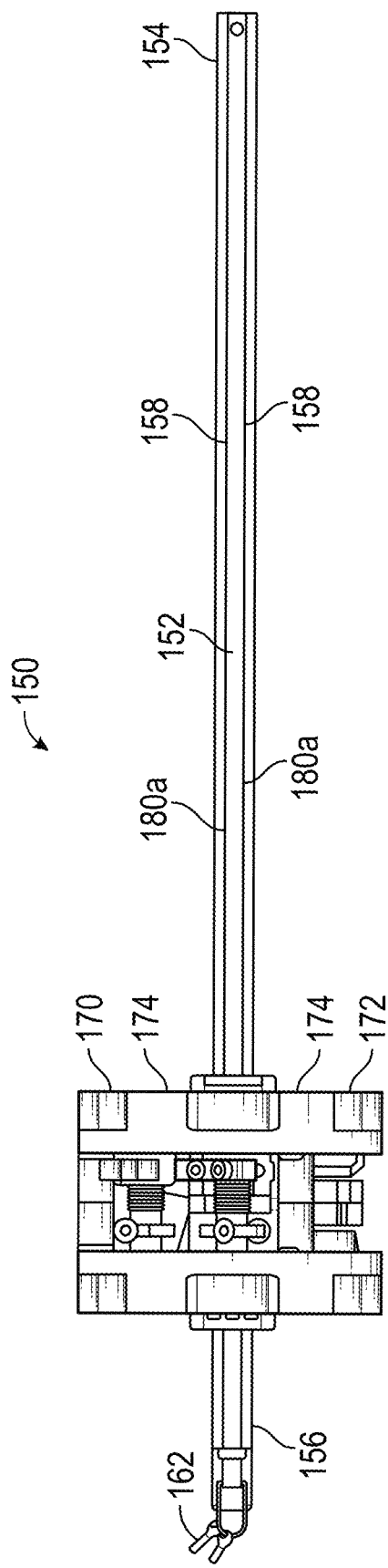
FIG. 18 illustrates an instrument having an instrument-based insertion architecture.

FIG. 18 illustrates an instrument having an instrument based insertion architecture in accordance with some embodiments. The instrument 150 can be coupled to any of the instrument drivers discussed above. The instrument 150 comprises an elongated shaft 152, an end effector 162 connected to the shaft 152, and a handle 170 coupled to the shaft 152. The elongated shaft 152 comprises a tubular member having a proximal portion 154 and a distal portion 156. The elongated shaft 152 comprises one or more channels or grooves 158 along its outer surface. The grooves 158 are configured to receive one or more wires or cables 180 therethrough. One or more cables 180 thus run along an outer surface of the elongated shaft 152. In other embodiments, cables 180 can also run through the elongated shaft 152. Manipulation of the one or more cables 180 (e.g., via an instrument driver) results in actuation of the end effector 162.

The instrument handle 170, which may also be referred to as an instrument base, may generally comprise an attachment interface 172 having one or more mechanical inputs 174, e.g., receptacles, pulleys or spools, that are designed to be reciprocally mated with one or more torque couplers on an attachment surface of an instrument driver.

In some embodiments, the instrument 150 comprises a series of pulleys or cables that enable the elongated shaft 152 to translate relative to the handle 170. In other words, the instrument 150 itself comprises an instrument-based insertion architecture that accommodates insertion of the instrument, thereby minimizing the reliance on a robot arm to provide insertion of the instrument 150. In other embodiments, a robotic arm can be largely responsible for instrument insertion.

E. Controller.

Any of the robotic systems described herein can include an input device or controller for manipulating an instrument attached to a robotic arm. In some embodiments, the controller can be coupled (e.g., communicatively, electronically, electrically, wirelessly and/or mechanically) with an instrument such that manipulation of the controller causes a corresponding manipulation of the instrument e.g., via master slave control.

Figure 19:
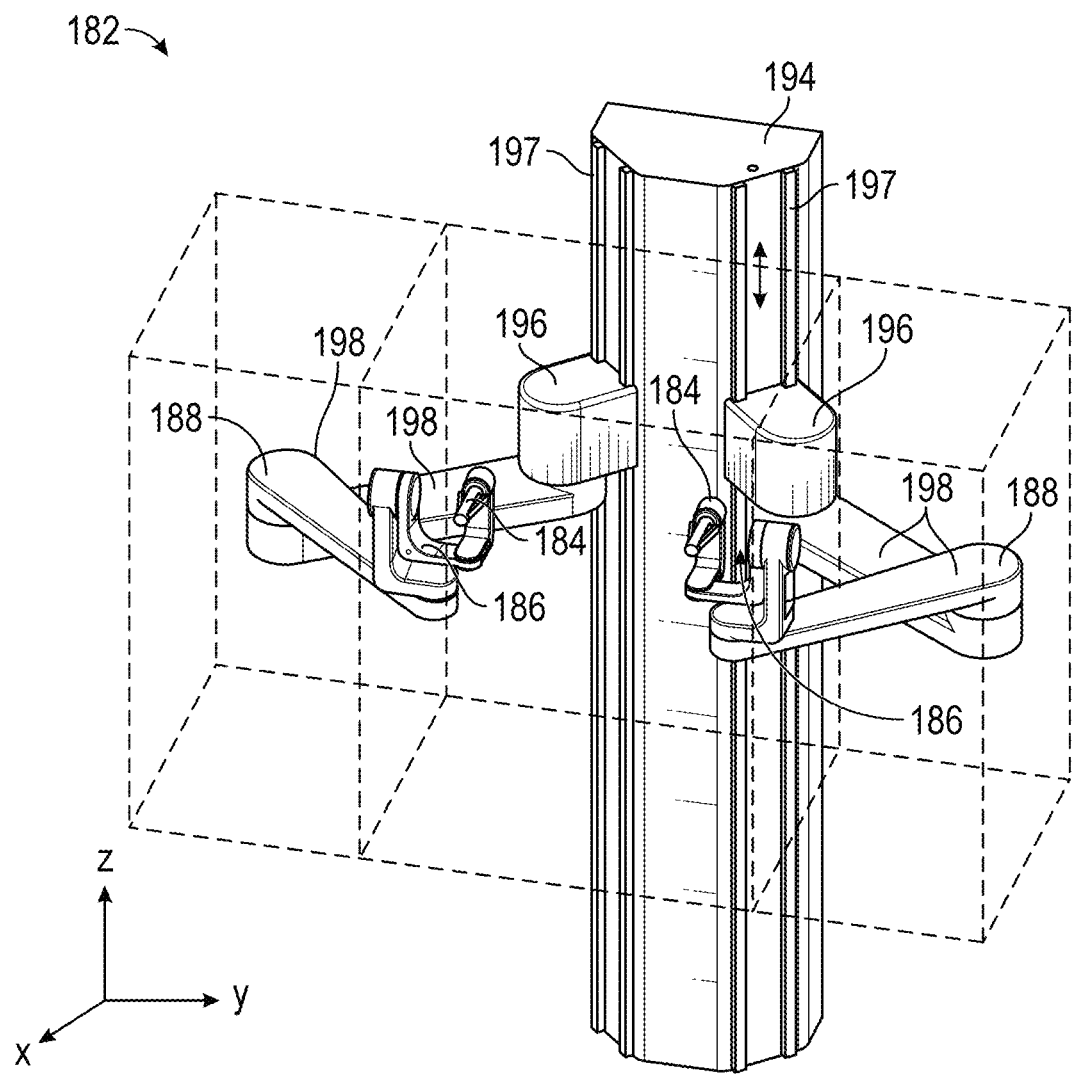
FIG. 19 illustrates an exemplary controller.

FIG. 19 is a perspective view of an embodiment of a controller 182. In the present embodiment, the controller 182 comprises a hybrid controller that can have both impedance and admittance control. In other embodiments, the controller 182 can utilize just impedance or passive control. In other embodiments, the controller 182 can utilize just admittance control. By being a hybrid controller, the controller 182 advantageously can have a lower perceived inertia while in use.

In the illustrated embodiment, the controller 182 is configured to allow manipulation of two medical instruments, and includes two handles 184. Each of the handles 184 is connected to a gimbal 186. Each gimbal 186 is connected to a positioning platform 188.

As shown in FIG. 19, each positioning platform 188 includes a SCARA arm (selective compliance assembly robot arm) 198 coupled to a column 194 by a prismatic joint 196. The prismatic joints 196 are configured to translate along the column 194 (e.g., along rails 197) to allow each of the handles 184 to be translated in the z-direction, providing a first degree of freedom. The SCARA arm 198 is configured to allow motion of the handle 184 in an x-y plane, providing two additional degrees of freedom.

In some embodiments, one or more load cells are positioned in the controller. For example, in some embodiments, a load cell (not shown) is positioned in the body of each of the gimbals 186. By providing a load cell, portions of the controller 182 are capable of operating under admittance control, thereby advantageously reducing the perceived inertia of the controller while in use. In some embodiments, the positioning platform 188 is configured for admittance control, while the gimbal 186 is configured for impedance control. In other embodiments, the gimbal 186 is configured for admittance control, while the positioning platform 188 is configured for impedance control. Accordingly, for some embodiments, the translational or positional degrees of freedom of the positioning platform 188 can rely on admittance control, while the rotational degrees of freedom of the gimbal 186 rely on impedance control.

F. Navigation and Control.

Traditional endoscopy may involve the use of fluoroscopy (e.g., as may be delivered through a C-arm) and other forms of radiation-based imaging modalities to provide endoluminal guidance to an operator physician. In contrast, the robotic systems contemplated by this disclosure can provide for non-radiation-based navigational and localization means to reduce physician exposure to radiation and reduce the amount of equipment within the operating room. As used herein, the term "localization" may refer to determining and/or monitoring the position of objects in a reference coordinate system. Technologies such as preoperative mapping, computer vision, real-time EM tracking, and robot command data may be used individually or in combination to achieve a radiation-free operating environment. In other cases, where radiation-based imaging modalities are still used, the preoperative mapping, computer vision, real-time EM tracking, and robot command data may be used individually or in combination to improve upon the information obtained solely through radiation-based imaging modalities.

Figure 20:
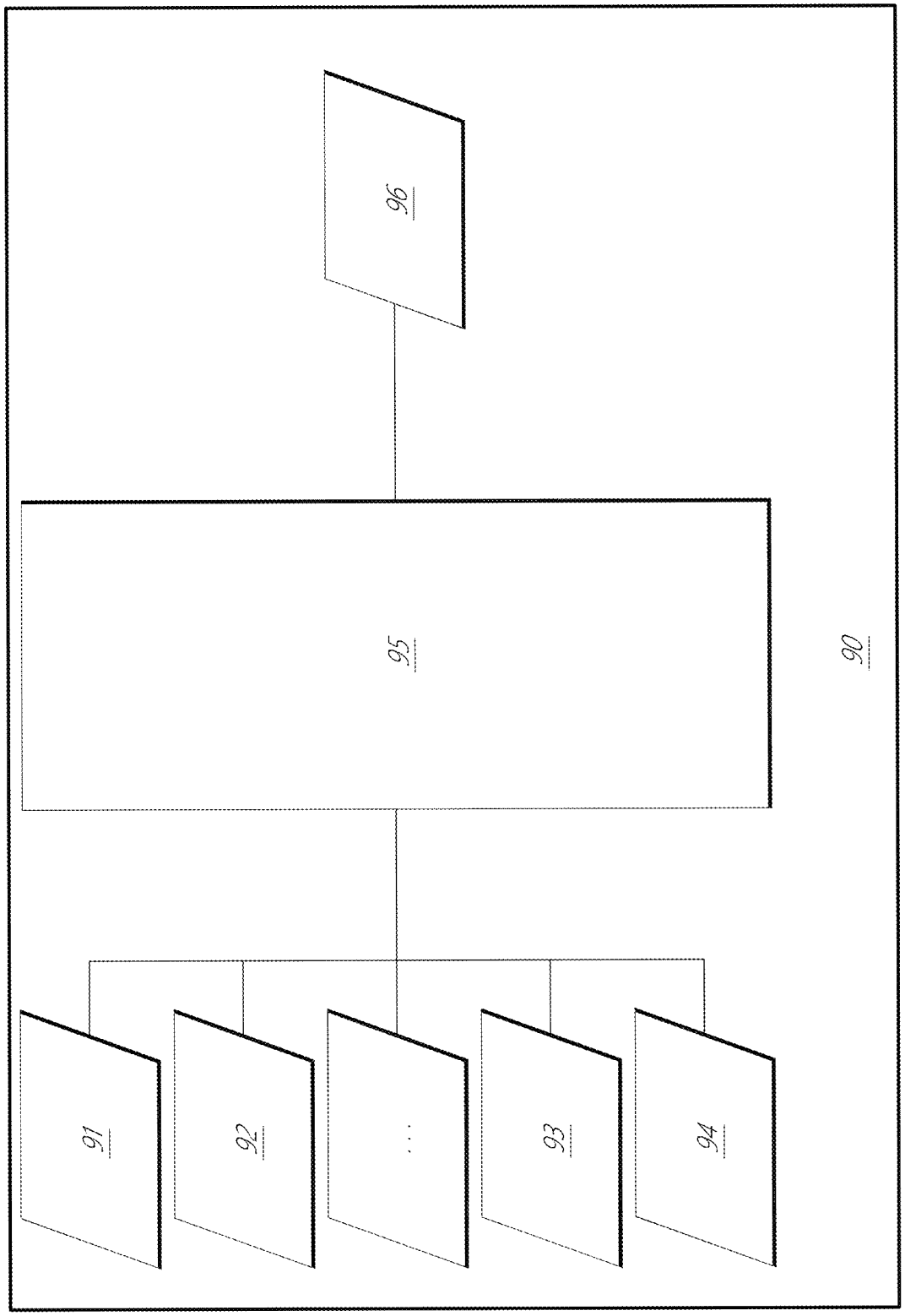
FIG. 20 depicts a block diagram illustrating a localization system that estimates a location of one or more elements of the robotic systems of FIGS. 1-10, such as the location of the instrument of FIGS. 16-18, in accordance with an example embodiment.

FIG. 20 is a block diagram illustrating a localization system 90 that estimates a location of one or more elements of the robotic system, such as the location of the instrument, in accordance to an example embodiment. The localization system 90 may be a set of one or more computer devices configured to execute one or more instructions. The computer devices may be embodied by a processor (or processors) and computer-readable memory in one or more components discussed above. By way of example and not limitation, the computer devices may be in the tower 30 shown in FIG. 1, the cart 11 shown in FIGS. 1-4, the beds shown in FIGS. 5-14, etc.

As shown in FIG. 20, the localization system 90 may include a localization module 95 that processes input data 91-94 to generate location data 96 for the distal tip of a medical instrument. The location data 96 may be data or logic that represents a location and/or orientation of the distal end of the instrument relative to a frame of reference. The frame of reference can be a frame of reference relative to the anatomy of the patient or to a known object, such as an EM field generator (see discussion below for the EM field generator).

The various input data 91-94 are now described in greater detail. Preoperative mapping may be accomplished through the use of the collection of low dose CT scans. Preoperative CT scans are reconstructed into three-dimensional images, which are visualized, e.g. as "slices" of a cutaway view of the patient's internal anatomy. When analyzed in the aggregate, image-based models for anatomical cavities, spaces and structures of the patient's anatomy, such as a patient lung network, may be generated. Techniques such as center-line geometry may be determined and approximated from the CT images to develop a three-dimensional volume of the patient's anatomy, referred to as model data 91 (also referred to as "preoperative model data" when generated using only preoperative CT scans). The use of center-line geometry is discussed in U.S. patent application Ser. No. 14/523,760, the contents of which are herein incorporated in its entirety. Network topological models may also be derived from the CT-images, and are particularly appropriate for bronchoscopy.

In some embodiments, the instrument may be equipped with a camera to provide vision data (or image data) 92. The localization module 95 may process the vision data 92 to enable one or more vision-based (or image-based) location tracking modules or features. For example, the preoperative model data 91 may be used in conjunction with the vision data 92 to enable computer vision-based tracking of the medical instrument (e.g., an endoscope or an instrument advance through a working channel of the endoscope). For example, using the preoperative model data 91, the robotic system may generate a library of expected endoscopic images from the model based on the expected path of travel of the endoscope, each image linked to a location within the model. Intraoperatively, this library may be referenced by the robotic system in order to compare real-time images captured at the camera (e.g., a camera at a distal end of the endoscope) to those in the image library to assist localization.

Other computer vision-based tracking techniques use feature tracking to determine motion of the camera, and thus the endoscope. Some features of the localization module 95 may identify circular geometries in the preoperative model data 91 that correspond to anatomical lumens and track the change of those geometries to determine which anatomical lumen was selected, as well as the relative rotational and/or translational motion of the camera. Use of a topological map may further enhance vision-based algorithms or techniques.

Optical flow, another computer vision-based technique, may analyze the displacement and translation of image pixels in a video sequence in the vision data 92 to infer camera movement. Examples of optical flow techniques may include motion detection, object segmentation calculations, luminance, motion compensated encoding, stereo disparity measurement, etc. Through the comparison of multiple frames over multiple iterations, movement and location of the camera (and thus the endoscope) may be determined.

The localization module 95 may use real-time EM tracking to generate a real-time location of the endoscope in a global coordinate system that may be registered to the patient's anatomy, represented by the preoperative model. In EM tracking, an EM sensor (or tracker) comprising one or more sensor coils embedded in one or more locations and orientations in a medical instrument (e.g., an endoscopic tool) measures the variation in the EM field created by one or more static EM field generators positioned at a known location. The location information detected by the EM sensors is stored as EM data 93. The EM field generator (or transmitter), may be placed close to the patient to create a low intensity magnetic field that the embedded sensor may detect. The magnetic field induces small currents in the sensor coils of the EM sensor, which may be analyzed to determine the distance and angle between the EM sensor and the EM field generator. These distances and orientations may be intraoperatively "registered" to the patient anatomy (e.g., the preoperative model) in order to determine the geometric transformation that aligns a single location in the coordinate system with a position in the preoperative model of the patient's anatomy. Once registered, an embedded EM tracker in one or more positions of the medical instrument (e.g., the distal tip of an endoscope) may provide real-time indications of the progression of the medical instrument through the patient's anatomy.

Robotic command and kinematics data 94 may also be used by the localization module 95 to provide localization data 96 for the robotic system. Device pitch and yaw resulting from articulation commands may be determined during preoperative calibration. Intraoperatively, these calibration measurements may be used in combination with known insertion depth information to estimate the position of the instrument. Alternatively, these calculations may be analyzed in combination with EM, vision, and/or topological modeling to estimate the position of the medical instrument within the network.

As FIG. 20 shows, a number of other input data can be used by the localization module 95. For example, although not shown in FIG. 20, an instrument utilizing shape-sensing fiber can provide shape data that the localization module 95 can use to determine the location and shape of the instrument.

The localization module 95 may use the input data 91-94 in combination(s). In some cases, such a combination may use a probabilistic approach where the localization module 95 assigns a confidence weight to the location determined from each of the input data 91-94. Thus, where the EM data may not be reliable (as may be the case where there is EM interference) the confidence of the location determined by the EM data 93 can be decrease and the localization module 95 may rely more heavily on the vision data 92 and/or the robotic command and kinematics data 94.

As discussed above, the robotic systems discussed herein may be designed to incorporate a combination of one or more of the technologies above. The robotic system's computer-based control system, based in the tower, bed and/or cart, may store computer program instructions, for example, within a non-transitory computer-readable storage medium such as a persistent magnetic storage drive, solid state drive, or the like, that, upon execution, cause the system to receive and analyze sensor data and user commands, generate control signals throughout the system, and display the navigational and localization data, such as the position of the instrument within the global coordinate system, anatomical map, etc.

2. Percutaneous Sheaths for Robotic Medical Systems and Related Methods.

The robotic medical systems described above can be configured to perform percutaneous assisted medical procedures, such as percutaneous assisted ureteroscopy (PAU), percutaneous nephrolithotomy (PCNL), and others. In general, PAU and PCNL are procedures that are performed to remove objects, such as kidney stones, from a patient's urinary tract. During PAU and PCNL, a physician establishes percutaneous access to a treatment site, such as the kidney, using a percutaneous access sheath. During the procedures, various medical instruments and tools can be passed through the percutaneous access sheath and into the treatment site. Such medical instruments and tools can include, for example, scopes (e.g., for allowing a physician to visualize the treatment site), lithotripters (e.g., for breaking stones to be removed into smaller fragments), basketing devices (for capturing and removing stones or fragments), and others. In a PAU procedure, an additional medical instrument, such as a ureteroscope, can be inserted into the treatment site through an orifice of the patient, such as the urethra. The additional medical instrument may be used together with the medical instruments and tools inserted percutaneously (e.g., through the percutaneous access sheath) to perform the procedures. In some embodiments, the additional medical instrument and/or the medical instruments and tools inserted percutaneously can be robotically controlled medical instruments as described above.

During PAU and PCNL, irrigation of fluid into and aspiration of fluid from the treatment site can be used to stabilize the treatment site and remove stones and fragments. During some procedures, a catheter (such as a percutaneous aspiration catheter (PAC)) is inserted through the percutaneous sheath and used to aspirate fluid and/or other objects (e.g., kidney stone fragments) from the treatment site. In some embodiments, to maintain fluid balance, as fluid is aspirated from the treatment site, irrigation should be provided to replace the fluid that is removed. In some instances, if the fluid is not replaced, the treatment site may collapse, making it difficult for the physician to visualize the treatment site and control the various medical instruments used during the procedures. However, providing irrigation into the kidney can pose a safety concern. One must be careful to avoid over pressurizing the treatment site, which could cause the treatment site to rupture.

This section describes percutaneous sheaths that can be used in percutaneous assisted procedures, such as PAU and PCNL (e.g., mini-PCNL), and others. The percutaneous sheaths can be configured to perform several functions. For example, the percutaneous sheaths can be configured to establish and maintain a path from outside the patient's body into the treatment site. This path can allow for various tools and medical instruments to be inserted into the treatment site through the percutaneous sheath. Additionally, and as will be described in greater detail below, the percutaneous sheaths can be configured to provide conduits or channels through which irrigation and/or aspiration of fluid can be provided. Thus, the percutaneous sheaths described in this section may facilitate administration of fluidics during the procedures for which they are used.

As noted briefly above, the percutaneous sheaths described in this section can be configured for use with robotic medical systems, such as the robotic medical systems described above with reference to FIGS. 1-20 and others. For example, in some embodiments, a robotic medical system may be used to insert and/or position the percutaneous sheath and/or to control one or more robotic medical instruments that may be inserted through the percutaneous sheath into the treatment site. Additionally or alternatively, a fluidics system and/or a robotic medical system can be connected to the percutaneous sheath to provide irrigation and/or aspiration through the conduits or channels of the percutaneous sheath.

In some embodiments, the percutaneous sheaths described in this section can be used during manually performed medical procedures. Thus, in some embodiments, the percutaneous sheaths can be used without a robotic medical system.

A. Example Percutaneous Sheaths.

Figure 21A:
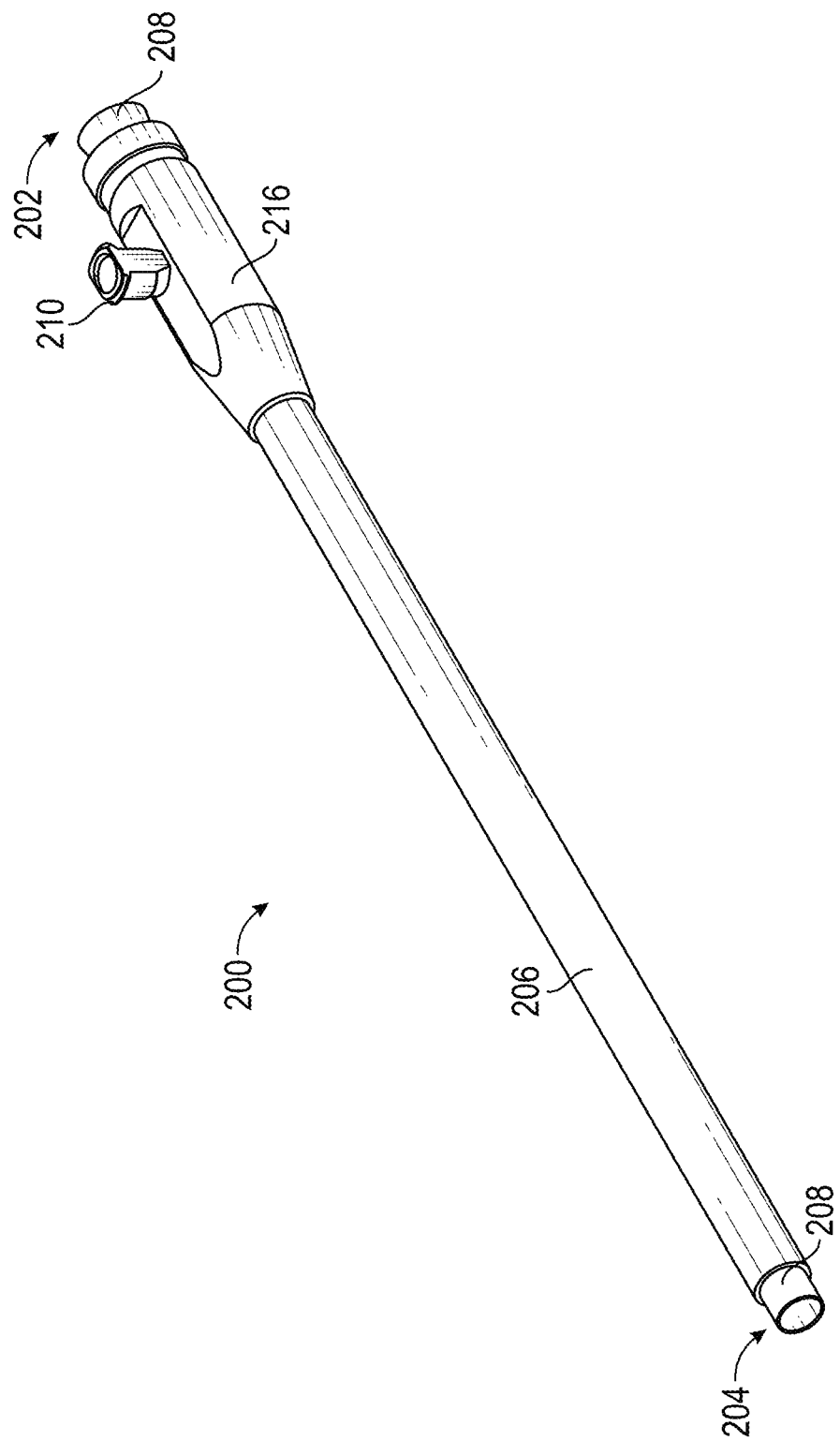
FIG. 21A is an isometric view of an embodiment of a percutaneous sheath.

FIG. 21A is an isometric view of another embodiment of a percutaneous sheath 200. In the illustrated embodiment, the percutaneous sheath 200 extends between a proximal end 202 and a distal end 204. The distal end 204 can be configured to be inserted into a treatment site of a patient. In some embodiments, the distal end 204 is sharpened, tapered, angled, or otherwise configured so that the distal end 204 can create a percutaneous cut in the patient through which the percutaneous sheath 200 can be inserted. In some embodiments, the distal end 204 is inserted through a previously formed percutaneous cut, opening, or port.

In general, during use of the percutaneous sheath 200, the distal end 204 is positioned within the treatment site and the proximal end 202 is positioned outside of the patient's body. As will be described below, the percutaneous sheath 200 can provide one or more paths, channels, or conduits from the proximal end 202 to the distal end 204 through which medical instruments can be inserted to reach the treatment site. The paths, channels, and conduits can also be used to provide irrigation and aspiration of fluid through the percutaneous access sheath 200.

The illustrated embodiment of the percutaneous sheath 200 comprises an outer conduit 206 and an inner conduit 208. In the illustrated embodiment, each of the outer conduit 206 and the inner conduit 208 extend generally from the proximal end 202 to the distal end 204. As shown in FIG. 21A (and also the cross-sectional view of FIG. 21C), the inner conduit 208 can be positioned within the outer conduit 206. As illustrated, the inner conduit 208 is concentrically arranged within the outer conduit 206; however, this need not be the case in all embodiments. Further, in some embodiments, the inner conduit 208 need not be positioned within the outer conduit 206. For example, the inner conduit 208 and the outer conduit 206 can be positioned side by side or in a stacked configuration.

In the illustrated embodiment, at the proximal end 202, the inner conduit 208 extends slightly beyond the proximal end of the outer conduit 206. This arrangement can allow a user to grip the proximal end 202 of the inner conduit 208 such that the user can lock the inner conduit 208 into place within the outer conduit 206 and/or remove the inner conduit 208 from the outer conduit 206. This, however, need not be the case in all embodiments. For example, at the proximal end 202, the outer conduit 206 can extend slightly beyond the proximal end of the inner conduit 208 or the proximal ends of the outer conduit 206 and the inner conduit 208 can be flush. Similarly, in the illustrated embodiment, at the distal end 204, the inner conduit 208 extends slightly beyond the distal end of the outer conduit 206. Again, this need not be the case in all embodiments. For example, at the distal end 204, the outer conduit 206 can extend slightly beyond the distal end of the inner conduit 208 or the distal ends of the outer conduit 206 and the inner conduit 208 can be flush. An example wherein the distal end 204 of the outer conduit 206 extends beyond the inner conduit 204 is shown in FIGS. 21A-21F described above. In some embodiments, the outer and inner conduits 206, 208 of the percutaneous sheath 200 are configured such that the distal end 204 of the inner conduit 208 is flush with or positioned proximally of the distal end 204 of the outer conduit 206.

Figure 21B:
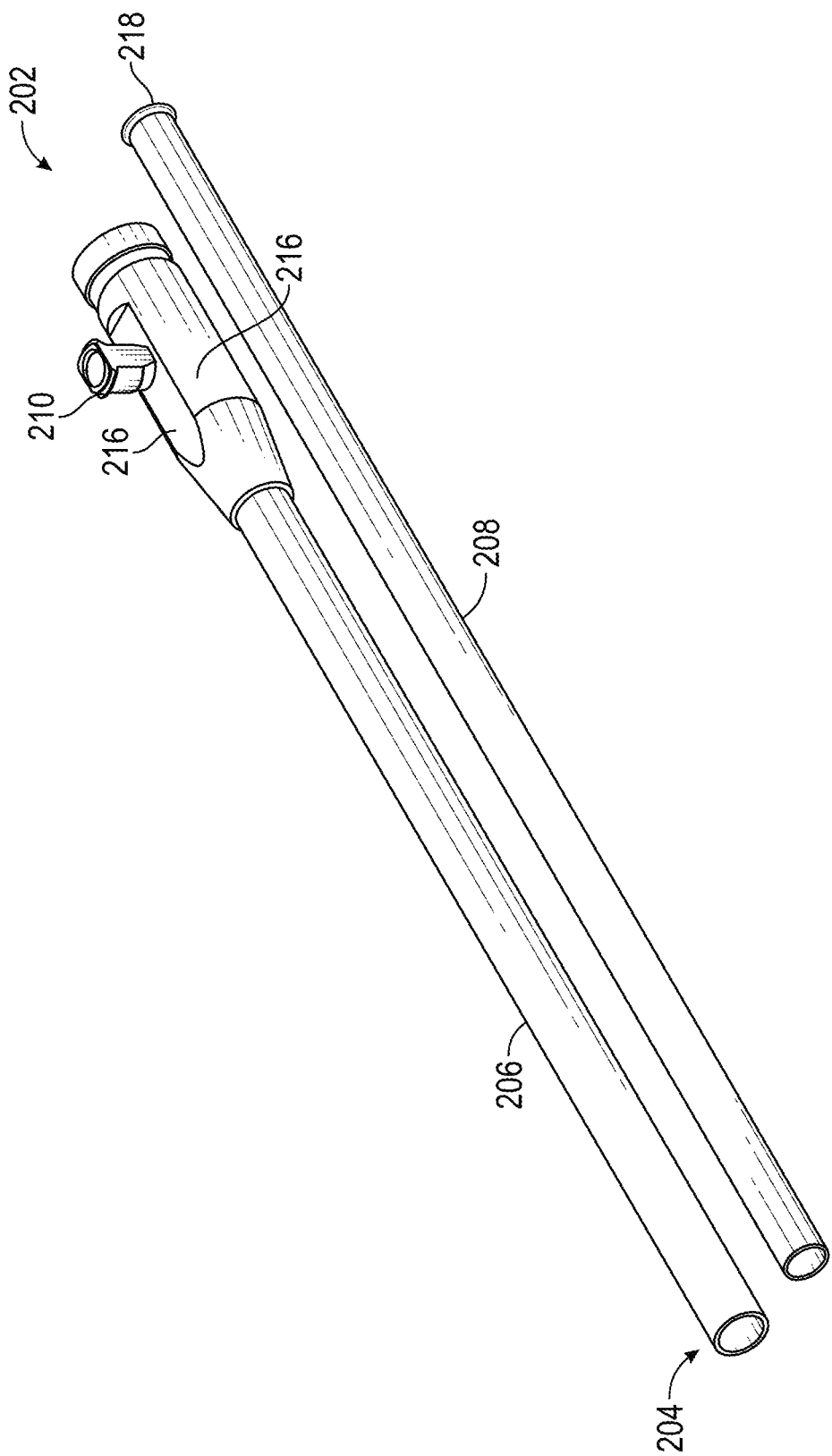
FIG. 21B illustrates the percutaneous sheath of FIG. 21A with an inner conduit removed.

FIG. 21B illustrates the percutaneous sheath 200 with the inner conduit 208 removed from the outer conduit 206. In some embodiments, the inner conduit 208 can be removable. For example, the inner conduit 208 can be configured to slide out of the outer conduit 206. In the some embodiments, when the inner conduit 208 is positioned within the outer conduit 206, it can be secured by a valve (e.g., a rubber valve or O-ring) to provide a seal between the proximal ends 202 of the outer conduit 206 and the inner conduit 208. In some embodiments, the inner conduit 208 can be removable from the outer conduit 206 to allow a dilator to fit through the outer conduit 206. In some embodiments, the inner conduit 208 is fixed (e.g., permanently fixed) within the outer conduit 206 and cannot be removed.

As shown in FIG. 21B (and also in the cross-sectional view of FIG. 21C), the outer conduit 206 can comprise a tube or pipe. In some embodiments, the outer conduit 206 is rigid. For example, the outer conduit 206 can be sufficiently rigid such that it can be percutaneously inserted into the patient. In some embodiments, the outer conduit 206 comprises a hypotube. A hypotube can allow for thin sidewalls so that the overall the dimensions of the percutaneous sheath 200 can be minimized, while maintaining sufficient strength and rigidity. This can reduce the tract size of the percutaneous sheath 200, which can reduce potential patient complications. In some embodiments, the outer conduit 206 comprises stainless steel, although other suitable materials can also be used. In the illustrated embodiment, the outer conduit 206 comprises a substantially circular cross-section, although this need not be the case in all embodiments. The cross-section of the outer conduit 206 can comprise other shapes. In some embodiments, the outer conduit 206 can comprise an outer diameter of 23 Fr. (0.302 inches) and an inner diameter of 21.4 Fr. (0.281 inches). These dimensions are provided by way of example, and other dimensions for the outer conduit 206 are possible. For example, the outer diameter of the outer conduit 206 can be about 21 Fr., about 22 Fr., about 23 Fr., about 24 Fr., or about 25 Fr., as well as other sizes both larger and smaller. Additionally, the inner diameter of the outer conduit 206 can be about 18 Fr. About 19 Fr., about 20 Fr., about 21 Fr., about 22 Fr., or about 23 Fr., as well as other sizes both larger and smaller.

Figure 21C:
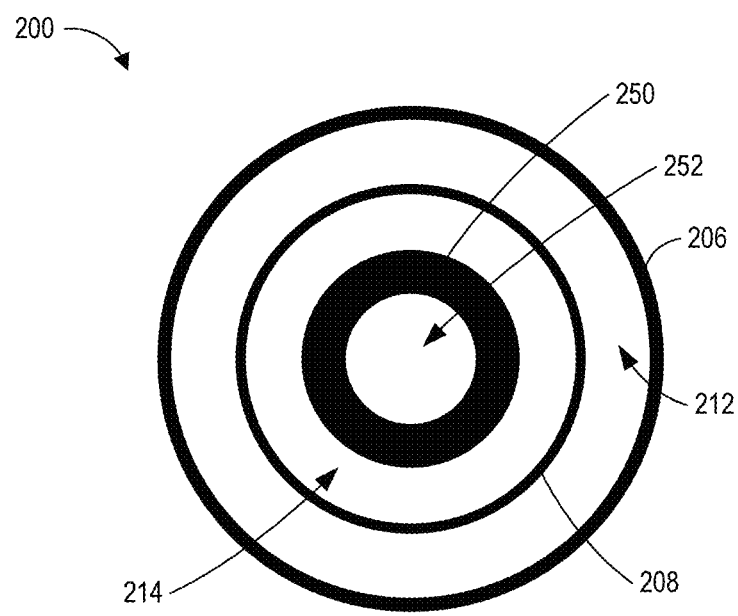
FIG. 21C is a cross-sectional view of the percutaneous sheath of FIG. 21A, illustrated with an aspiration catheter positioned within an inner conduit of the percutaneous sheath.

As illustrated in FIGS. 21A and 21C, a hub 216 can be positioned at the proximal end 202 of the outer conduit 206. In some embodiments, the outer conduit 206 is welded to the hub 216, although other methods for joining the outer conduit 206 and the hub 216 are possible. A fluid inlet 210 can be positioned on the hub 216. As will be described in more detail below, the fluid inlet 210 can be configured to connect to an irrigation source such that irrigation can be provided through the percutaneous sheath 200 and into the treatment site. In the illustrated embodiment, the fluid inlet 210 is configured as a side port. For example, a longitudinal axis of the fluid inlet is transverse (e.g., angled or perpendicular) to a longitudinal axis of the outer conduit 206. In the illustrated embodiment, the fluid inlet 210 is configured as a Luer connector. Other types of connectors can be used in other embodiments. Further, in some embodiments, the fluid inlet 210 can be positioned in other locations on the hub 216 and/or other portions of the outer conduit 206.

In some embodiments, the hub 216 is made from extruded plastic, although other methods of manufacture and types of materials are also possible. In some embodiments, the hub 216 comprises plastic (such as ABS plastic, polycarbonate, or other suitable plastics) overmolded onto the outer conduit 206. In some embodiments, for example, as shown in the embodiment illustrated in FIGS. 22A-22D, described below) the percutaneous sheath 200 can also include a hub 217 on the inner conduit 208. The hub 217 of the inner conduit can facilitate engagement and sealing between the outer conduit 206 and the inner conduit 208. In some embodiments, the hub 217 of the inner conduit 208 comprises plastic (such as ABS plastic, polycarbonate, or other suitable plastics) overmolded onto the inner conduit 208.

The hub 216 may also include a valve positioned therein. When the inner conduit 208 is positioned within the outer conduit 206, the inner conduit 208 may extend through the valve of the hub 216. The valve of the hub 216 may seal the proximal end 202 of the outer conduit 206.

With reference to FIG. 21B (see also the cross-sectional view of FIG. 22C), the inner conduit 208 can comprise a tube or pipe. In some embodiments, the inner conduit 208 is rigid. For example, the inner conduit 208 can be sufficiently rigid such that it can be percutaneously inserted into the patient. In some embodiments, the inner conduit 208 comprises a hypotube. In some embodiments, the inner conduit 208 comprises stainless steel, although other materials can also be used. In the illustrated embodiment, the inner conduit 208 comprises a substantially circular cross-section, although this need not be the case in all embodiments. The cross-section of the inner conduit 208 can comprise other shapes. In some embodiments, the inner conduit 208 can comprise an outer diameter of 19.1 Fr. (0.251 inches) and an inner diameter of 18.1 Fr. (0.238 inches). Again, these dimensions are provided by way of example, and other dimensions for the inner conduit 208 are possible. For example, the outer diameter of the inner conduit 208 can be about 16 Fr., about 17 Fr., about 18 Fr., about 19 Fr., about 20 Fr., about 21 Fr., or about 22 Fr., as well as other sizes both larger and smaller. Additionally, the inner diameter of the inner conduit 208 can be about 14 Fr., about 15 Fr., about 16 Fr., about 17 Fr., about 18 Fr., about 19 Fr., or about 20 Fr., as well as other sizes both larger and smaller. As shown in FIG. 21B, the proximal end 202 of the inner conduit 208 can include a flare or rib 218. The rib 218 can serve as a hard stop that can limit insertion of the inner conduit 208 relative to the outer conduit 206. For example, in some embodiments, the rib 218 is sufficiently large such that it cannot pass through the hub 216. As noted previously and as will be described in more detail below, in some embodiments, the inner conduit 206 can include a hub 217, which can be included in addition to or in place of the rib 218.

FIG. 21C is a cross-sectional view of the percutaneous sheath 200. In this view, one can see that, in the illustrated embodiment, the inner conduit 208 is positioned within the outer conduit 206 such that a first channel 212 is formed between an inner wall of the outer conduit 206 and an outer wall of the inner conduit 208. The first channel 212 can be connected to the fluid inlet 210. In some embodiments, the first channel 212 is configured to provide irrigation through the percutaneous sheath 200. For example, an irrigant (fluid) can enter the first channel 212 at the fluid inlet 210, flow through the first channel 212, and exit at the distal end 204.

The valve of the hub 216 (or another method or structure) can seal the first channel 212 at the proximal end 202 such that fluid does not exit the first channel 212 at the proximal end 202. In some embodiments, the valve of the hub 216 can include a pressure relief valve configured to allow fluid to exit at the proximal end 202 of the first channel 212 if the pressure exceeds a threshold. For example, the proximal end 202 of the percutaneous sheath 200 could include a rubber diaphragm valve or similar structure that is configured to rupture or otherwise open if subject to a certain pressure. This may reduce the likelihood that the treatment site will be over pressurized and burst.

As shown in FIG. 21C, a second channel 214 is formed by the inner conduit 208. In some embodiments, the second channel 214 is defined by the inner wall of the inner conduit 208. The second fluid channel 214 can provide an open passage through the percutaneous sheath 200 from the proximal end 202 to the distal end 204. In some embodiments, the second channel 214 provides a working channel through the percutaneous sheath 200 through which other medical instruments or tools can be inserted into the treatment site. In some embodiments, the second channel 214 is open from the proximal end 202 to the distal end 204 of the percutaneous sheath 200.

As illustrated in the cross-sectional view of FIG. 21C, a catheter 250 (e.g., an aspiration catheter or other medical instrument) can be inserted through the second channel 214.

The catheter 250 can include an aspiration channel 252 through which fluid from the treatment site can be aspirated. In some embodiments, the catheter 250 is robotically controlled although the percutaneous sheath 200 can also be used with manual catheters 250. In some embodiments, the catheter 250 can be steerable or articulable As shown in FIG. 21C, in some embodiments, even when the catheter 250 is inserted through the second channel 214, space remains between the outer wall of the catheter 250 and the inner wall of the inner conduit 208. In some embodiments, this space can be used to provide passive outflow of fluid from the treatment site. That is, in some embodiments, fluid can outflow from the treatment site through the second channel 214 in the space between the catheter 250 and the inner conduit 208. This can prevent or reduce the likelihood that the treatment site will be over pressurized and burst. Passive outflow through the second channel 214 is shown, for example, in FIG. 24, which is described below.

Figure 22A:
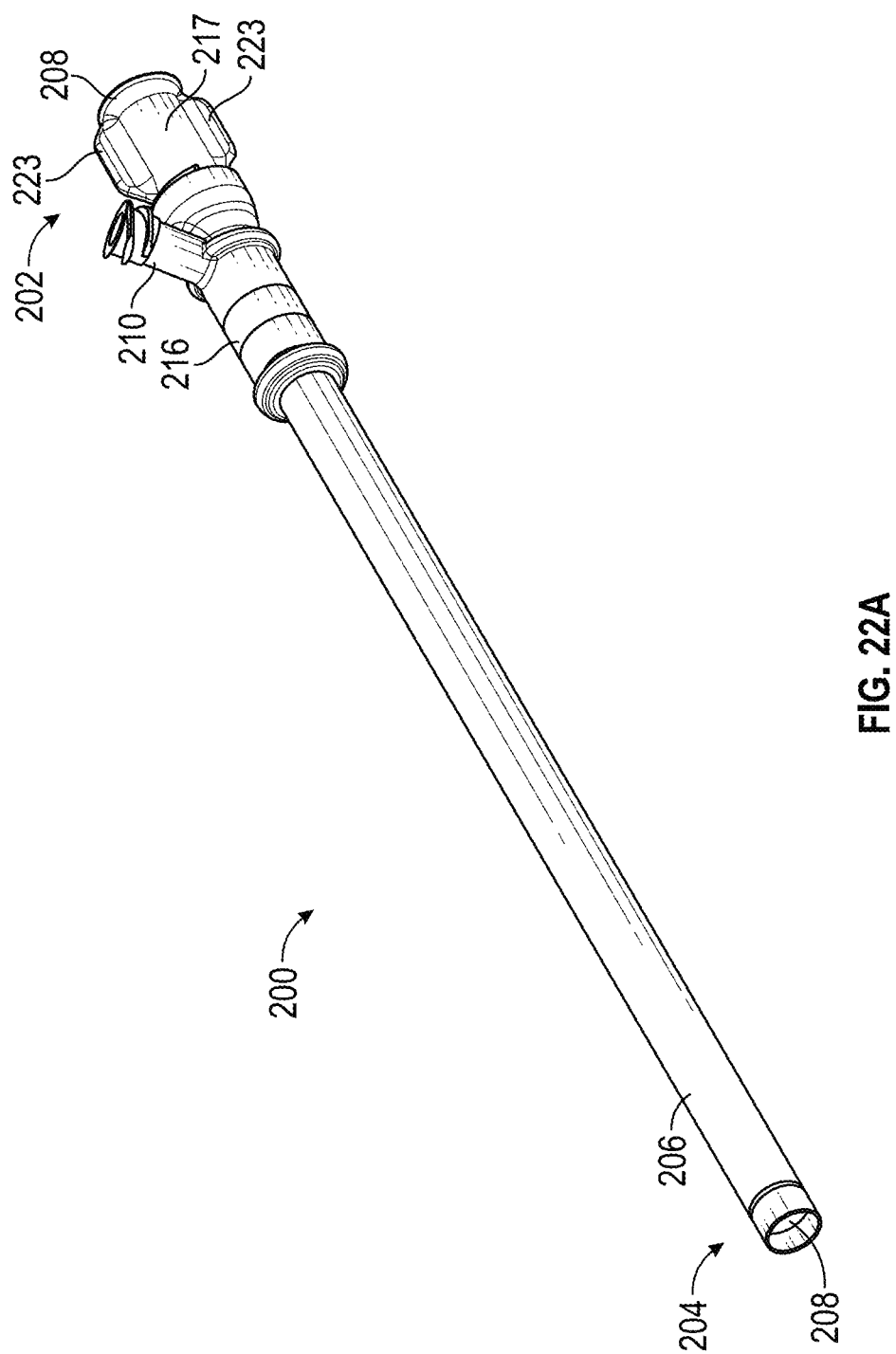
FIG. 22A is an isometric view of another embodiment of a percutaneous sheath that includes an outer conduit and an inner conduit.
Figure 22B:
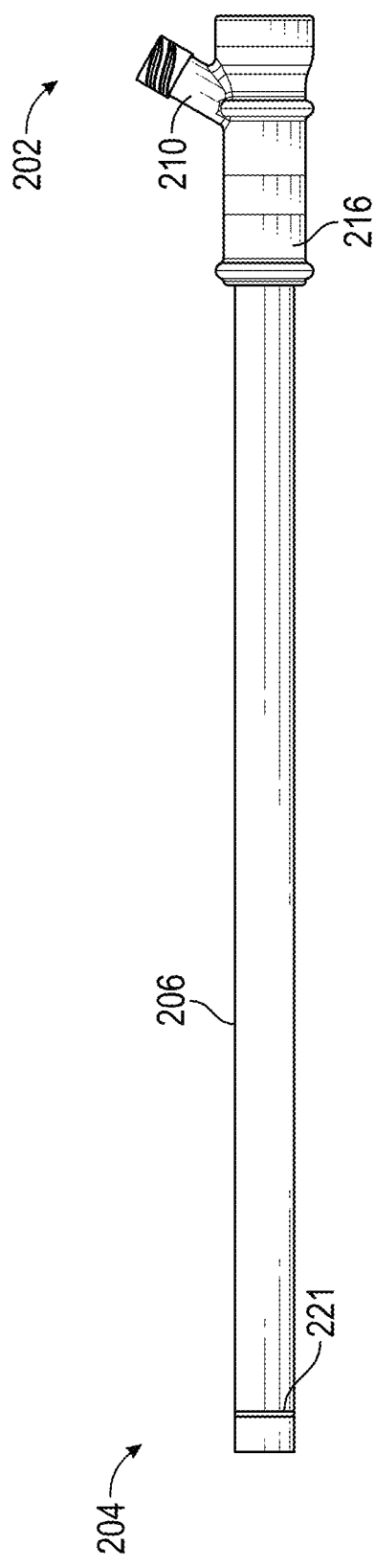
FIG. 22B is a side view of an embodiment of the outer conduit of the percutaneous sheath of FIG. 22A.
Figure 22C:
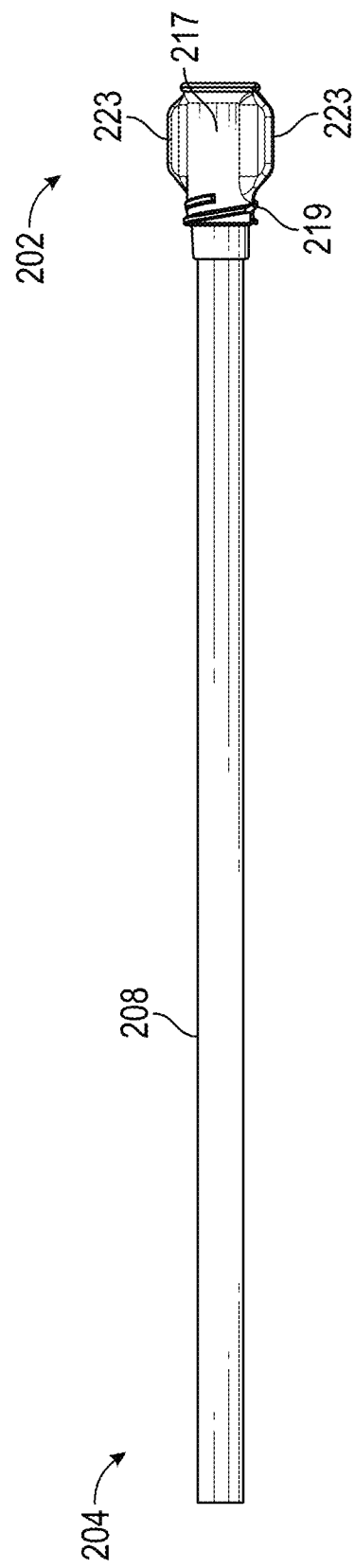
FIG. 22C is a side view of an embodiment of the inner conduit of the percutaneous sheath of FIG. 22A.

FIG. 22A is an isometric view of another embodiment of a percutaneous sheath 200. In the illustrated embodiment, the percutaneous sheath 200 includes an outer conduit 206 and an inner conduit 208. The inner conduit 208 can be insertable into the outer conduit 206 to provide the percutaneous sheath 200 with multiple channels therethrough as described above with respect to FIG. 21C. In FIG. 22A, the percutaneous sheath 200 is shown with the inner conduit 208 inserted into the outer conduit 206. FIG. 22B is a side view of an embodiment of the outer conduit 206 of the percutaneous sheath 200, and FIG. 22C is a side view of an embodiment of the inner conduit of the percutaneous sheath 200.

As shown for the illustrated embodiment of FIG. 22A, the percutaneous sheath 200 extends between a proximal end 202 and a distal end 204. In general, during use, the distal end 204 is configured to be inserted into the patient, while the proximal end 202 remains outside of the patient. FIG. 22A also illustrates that the percutaneous sheath 200 can include a first hub 216 and a second hub 217 at the proximal end 204. The first hub 216 can be connected to the outer conduit 206. The second hub 217 can be connected to the inner conduit 208. As will be described in more detail below, the first conduit 216 and the second conduit 217 can be configured to engage with each other to connect the outer conduit 206 to the inner conduit 208 and to provide a seal at the proximal end 202 for one or more of the channels that extend through the percutaneous sheath.

FIG. 22B is a side view of the outer conduit 206. The outer conduit 206 can comprise a tube or pipe extending between the proximal end 202 and the distal end 204. In some embodiments, the outer conduit 206 is rigid such that it can be percutaneously inserted into the patient as described above. In some embodiments, the outer conduit 206 comprises a hypotube. As mentioned previously, configuring the outer conduit 206 as a hypotube can allow for thin sidewalls so that the overall the dimensions of the percutaneous sheath 200 can be minimized, while maintaining sufficient strength and rigidity. The outer conduit 206 can comprise stainless steel, although other suitable materials can also be used. In the illustrated embodiment, the outer conduit 206 comprises a substantially circular cross-section, although this need not be the case in all embodiments. The cross-section of the outer conduit 206 can comprise other shapes. In some embodiments, the outer conduit 206 can comprise an outer diameter of 23 Fr. (0.302 inches) and an inner diameter of 21.4 Fr. (0.281 inches). These dimensions are provided by way of example, and other dimensions for the outer conduit 206 are possible. In the illustrated embodiment, a circumferential groove 221 is provided at the distal end 204.

As illustrated in FIG. 22B, the first hub 216 can be positioned at the proximal end 202 of the outer conduit 206. In some embodiments, the first hub 216 is made from extruded plastic, although other methods of manufacture and types of materials are also possible. In some embodiments, the hub 216 comprises plastic (such as ABS plastic, polycarbonate, or other suitable plastics) overmolded onto the proximal end 202 of the outer conduit 206. A fluid inlet 210 can be positioned on the hub 216 as described above. The fluid inlet 210 can be configured to connect to an irrigation source such that irrigation can be provided through the percutaneous sheath 200 and into the treatment site. In the illustrated embodiment, the fluid inlet 210 is configured as a Luer connector.

FIG. 22C is a side view of the inner conduit 208. The inner conduit 208 can comprise a tube or pipe extending between the proximal end 202 and the distal end 204. In some embodiments, the inner conduit 208 is rigid. In some embodiments, the inner conduit 208 comprises a hypotube. As mentioned previously, configuring the inner conduit 208 as a hypotube can allow for thin sidewalls so that the overall the dimensions of the percutaneous sheath 200 can be minimized. The inner conduit 208 can comprise stainless steel, although other suitable materials can also be used. In the illustrated embodiment, the inner conduit 208 comprises a substantially circular cross-section, although this need not be the case in all embodiments. In some embodiments, the inner conduit 208 can comprise an outer diameter of 19.1 Fr. (0.251 inches) and an inner diameter of 18.1 Fr. (0.238 inches), for example.

Figure 22D:
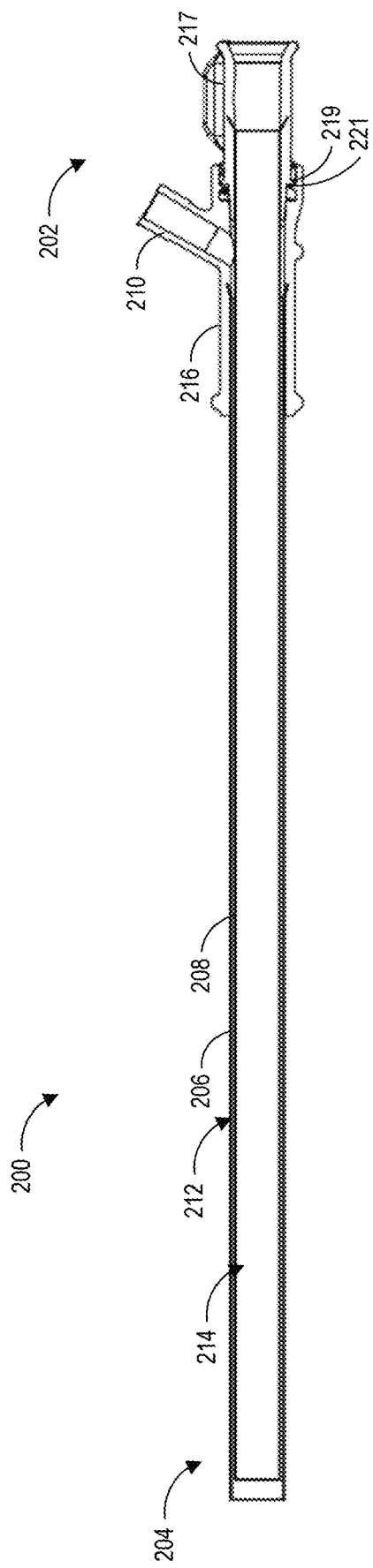
FIG. 22D is a longitudinal cross-sectional view of the percutaneous sheath of FIG. 22A illustrating the inner conduit positioned within the outer conduit.

As illustrated in FIG. 22C, the second hub 217 can be positioned at the proximal end 202 of the inner conduit 208. In some embodiments, the second hub 217 is made from extruded plastic, although other methods of manufacture and types of materials are also possible. In some embodiments, the second hub 217 comprises plastic (such as ABS plastic, polycarbonate, or other suitable plastics) overmolded onto the proximal end 202 of the inner conduit 208. As shown in FIG. 22C, the second hub 217 can include a threaded portion 219 configured to engage with a corresponding threaded portion 212 (as shown in FIG. 22D) on the interior of the first hub 216. This engagement can secure the inner conduit 208 to the outer conduit 206. Further, in some embodiments, the engagement between the first hub 216 and the second hub 217 can seal a first channel 212 though the percutaneous sheath 200 at the proximal end as will be shown in more detail in the cross-sectional view of FIG. 22D. Although illustrated with threaded portion 219, 221, the first and second hubs 216, 217 can be configured to engage in other ways. For example, the first and second hubs 216, 217 can be configured in size and shape to provide a friction fit therebetween. FIG. 22C also illustrates that the second hub 217 can include one more flanges 223. The flanges 223 can be provided to facilitate screwing the second hub 217 into and out of the first hub 216.

FIG. 22D is a longitudinal cross-sectional view of the percutaneous sheath of FIG. 22A illustrating the inner conduit 208 positioned within the outer conduit 206. As shown, the first hub 216 is engaged with the second hub 217. In the illustrated embodiment, the threaded portion 219 of the second hub 217 is threaded into the threaded portion 221 of the first hub 216. As shown in FIG. 22D, when the inner conduit 208 is inserted into the outer conduit 206, the percutaneous sheath 200 can provide a first channel 212 and a second channel 214 therethrough in an arrangement similar to that described above with reference to FIG. 21C. For example, the first channel 212 can be provided between an inner wall of the outer conduit 206 and an outer wall of the inner conduit 208. The first channel 212 can be connected to the fluid inlet 210 at the proximal end 202. The first channel 212 can be otherwise sealed at the proximal end 202 by the engagement between the first and second hubs 216, 217. A second channel 214 can be provided through the inner conduit 208, which can be open at the proximal and distal ends 202, 204.

The percutaneous sheath 200 can be configured for use during percutaneous assisted medical procedures such as PAU, PCNL, or others. In some embodiments, irrigation is provided into the treatment site (e.g., a kidney) through the first channel 212, and aspiration can be provided through the aspiration channel 252 of the catheter 250 that is inserted through the inner conduit 208. In some embodiments, the percutaneous sheath 200 allows for passive outflow of the fluid from the treatment site through the second channel 214 in the space between the catheter 250 and the inner conduit 208.

In some embodiments, the percutaneous sheath 200 can provide one or more of the following features or functions. Not every feature need be provided in all embodiments and other functions and features than those listed can also be provided by the percutaneous sheath 200. First, the percutaneous sheath 200 can maintain an antegrade percutaneous tract allowing antegrade devices to be inserted and retracted there through. For example, the inner conduit 208 can provide a tract, channel, or other passageway through the percutaneous sheath 200. Second, the percutaneous sheath 200 can be configured to provide irrigation (e.g., to provide a pathway for irrigation into the treatment site), which can be used to distend the treatment site during the procedure. For example, irrigation can be provided through the first channel 212. Third, the percutaneous sheath 200 can provide an open channel for fluid to passively outflow from the treatment site. For example, passive outflow can pass through the through the second channel 214 in the space between the catheter 250 and the inner conduit 208.

Figure 24:
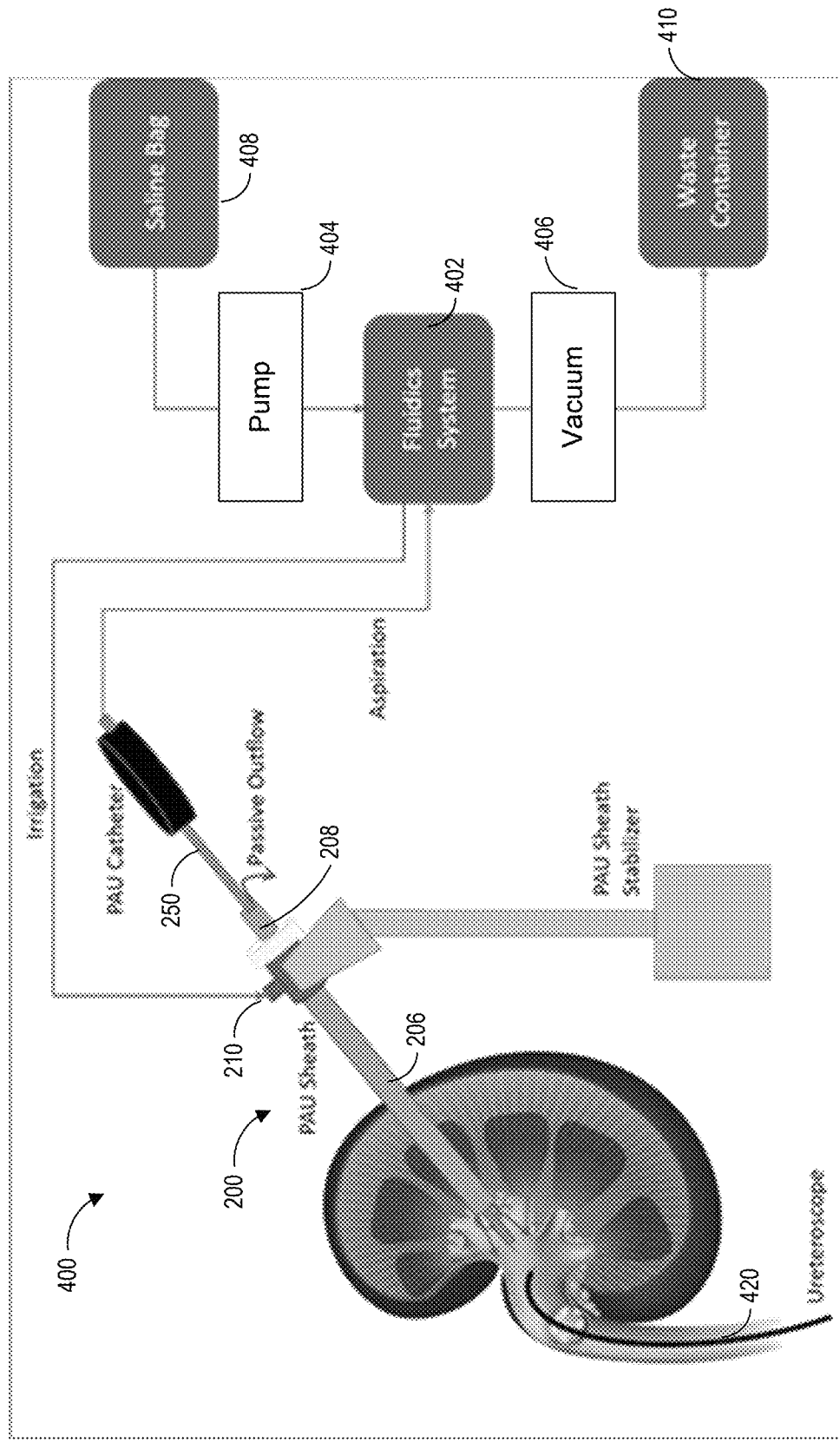
FIG. 24 schematically illustrates an embodiment of a system that includes a percutaneous sheath, an aspiration catheter, and a fluidics system.

As will be discussed below with reference to FIG. 24, the percutaneous sheath 200 (and catheter 250) can be connected to a fluidics system, which can manage irrigation and aspiration during the procedure. Irrigation can be used to distend the treatment site, while aspiration can be used to extract stone fragments and remove excess fluid. In some embodiments, the catheter 250 can provide the conduit through which stone fragments are passed from inside the treatment site to the outside of the patient. The fluidics system (e.g., as shown in FIG. 24) can maintain the balance of irrigation and aspiration for providing adequate distension and optimal stone removal performance. In some embodiments, optimal stone removal performance can be achieved by providing good stone holding through high aspiration pressure balanced with irrigation that can refill the kidney and collecting system to maintain distension and visualization In some embodiments, the dimensions of the outer conduit 206, inner conduit 208, and catheter 250 can be configured to provide balanced flow (irrigation and aspiration) through the percutaneous sheath 200, while working within generally accepted size constraints for PAU and PCNL procedures. For example, in some embodiments, the percutaneous sheath 200 can be configured such that it can be considered to have "Mini-PCNL" sizing. For example, in some embodiments the outer diameter of the working length of the outer conduit 206 (e.g., the portion that is inserted into the patient) does not exceed 22.3 Fr. Further, in some embodiments, the percutaneous sheath 200 is configured to use standard PCNL irrigation settings (e.g., maximum and minimum inflow rates, outflow rates, pressures, etc.), such that the percutaneous sheath 200 can be used with existing fluidics systems. When configured for standard PCNL, the percutaneous sheath 200 can have an outer dimeter of up to 30 Fr, for example. When configured for min-PCNL, the percutaneous sheath 200 can have an inner diameter of between 13 Fr and 18 Fr, for example. Other sizes are also possible. Finally, in some embodiments, the size of the inner conduit 208 can be configured relative to the outer dimension of the catheter 250 such that the second channel 214 provides a sufficient volume between the catheter 250 and the inner conduit 208 to allow for sufficient passive outflow through the percutaneous sheath 200. For example, in some embodiments, the inner conduit 208 comprises an inner dimeter of about 0.238 inches and an outer diameter of 0.251 inches. Other sizes are also possible.

In some embodiments, the percutaneous sheath 200 can be advantageous because it can be configured to prevent or reduce over pressurization of the treatment site. Further, the percutaneous sheath 200 can be advantageous because it is able to allow irrigation into the treatment site independent of other percutaneous devices (e.g., lithotripters, nephroscopes).

In some embodiments, the percutaneous sheath 200 can include one or more sensors positioned thereon for measuring various parameters. For example, the percutaneous sheath 200 can include a pressure sensor for measuring a pressure within the kidney, a flow sensor for measuring a flow rate into the kidney, and/or a flow sensor for measuring a flow rate out of the kidney. These sensors can be positioned on or within the outer conduit 206, the inner conduit 208, the hub 216, or elsewhere on the percutaneous sheath 200.

Figure 23:
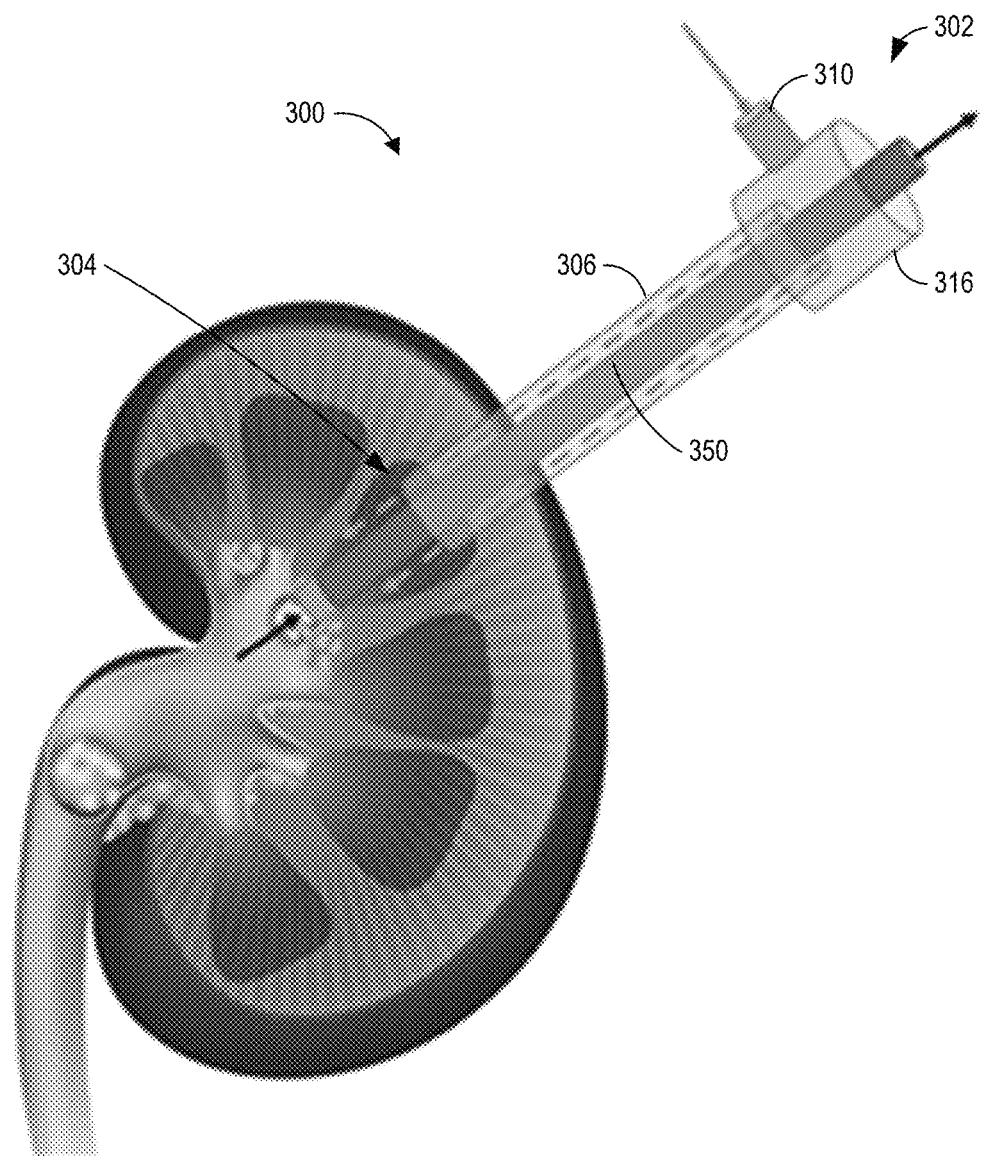
FIG. 23 illustrates another embodiment of a percutaneous sheath inserted into a kidney.

FIG. 23 illustrates another embodiment of a percutaneous sheath 300. In the illustrated embodiment, the percutaneous sheath 300 is shown inserted into a kidney. As illustrated, the percutaneous sheath 300 extends between a proximal end 302 and a distal end 304. The distal end 304 can be configured to be inserted into a treatment site (e.g., the kidney) of a patient. In some embodiments, the distal end 304 is sharpened, tapered, angled, or otherwise configured so that the distal end 304 can create a percutaneous cut in the patient through which the percutaneous sheath 300 can be inserted as described above.

The illustrated embodiment of the percutaneous sheath 300 comprises a conduit 306. The conduit 306 can comprise a tube or pipe. In some embodiments, the conduit 306 is rigid. For example, the conduit 306 can be sufficiently rigid such that it can be percutaneously inserted into the patient. In some embodiments, the conduit 306 comprises a hypotube. In some embodiments, the conduit 306 comprises stainless steel. In the illustrated embodiment, the conduit 306 comprises a substantially circular cross-section, although this need not be the case in all embodiments. The cross-section of the conduit 306 can comprise other shapes. In contrast with the percutaneous sheaths 200 described above with reference to FIGS. 21A-22C, the percutaneous sheath 200 includes a single conduit 306 rather than outer and inner conduits 206, 208 as described previously.

With reference to FIG. 23, a hub 316 can be positioned at the proximal end 302 of the conduit 306. In some embodiments, the conduit 306 is welded to the hub 316, although other methods for joining the conduit 306 and the hub 316 are possible. A fluid inlet 310 can be positioned on the hub 316. The fluid inlet 310 can be configured to connect to an irrigation source such that irrigation can be provided through the percutaneous sheath 300 and into the treatment site. In the illustrated embodiment, the fluid inlet 310 is configured as a side port. Other port positions can be used in other embodiments. The fluid inlet 310 can comprise a Luer connector. Other types of connectors can be used in other embodiments.

For the percutaneous sheath 300, the hub 316 includes a valve or other sealing structure positioned therein. The valve of the hub 316 can be configured to allow an catheter 350 to be inserted there through as shown in FIG. 23. The valve can seal around the catheter 350, sealing the proximal end 302 of the conduit 306. In some embodiments, the valve may be configured with a pressure-relief function. If the pressure within the percutaneous sheath 300 or treatment site exceeds a certain pressure, the valve can allow fluid to flow out the proximal end 302, thereby relieving the pressure. Alternatively, the fluid inlet 310 can have a pressure relief valve so that incoming irrigant can be expelled if the pressure becomes too high. This can prevent or reduce the likelihood that the treatment site will be over pressurized and burst.

An catheter 350 can be inserted through the conduit 306 in a manner similar to that previously described with respect to FIG. 21C. As described above, the catheter 350 can include an aspiration channel through which fluid from the treatment site can be aspirated. In some embodiments, the catheter 350 is robotically controlled. In some embodiments, the catheter 350 is steerable or articulable.

The percutaneous sheath 300 can be configured for use during percutaneous assisted medical procedures such as PAU and PCNL or others. In some embodiments, irrigation is provided into the treatment site (e.g., the kidney) through the conduit 306, and aspiration can be provided through the aspiration channel of the catheter 350 that is inserted through the conduit 306.

As will be discussed below with reference to FIG. 24, the percutaneous sheath 300 (and catheter 350) can be connected to a fluidics system, which can manage irrigation and aspiration during the procedure.

In some embodiments, the dimensions of the conduit 306 and catheter 350 can be configured to provide balanced flow (irrigation and aspiration) through the percutaneous sheath 300 and catheter 350, while working within generally accepted size constraints for PAU and PCNL procedures. For example, in some embodiments, the percutaneous sheath 300 can be configured such that it can be considered to have "Mini-PCNL" sizing. For example, in some embodiments, the outer diameter of the working length of the outer conduit 306 does not exceed 22.3 Fr. As another example, the inner diameter of the conduit 306 can be 18 Fr., which can be considered a mini-PCNL size. Further, in some embodiments, the percutaneous sheath 300 is configured to use the mini and/or standard PCNL irrigation sizings and settings as described above.

In some embodiments, the size of the conduit 306 can be configured relative to the outer dimension of the catheter 350 to allow irrigant to flow in the space between the inner diameter of the conduit 306 and the outer diameter of the catheter 350 as described previously.

In some embodiments, the percutaneous sheath 300 can beneficially be configured to prevent or reduce over pressurization of the treatment site via the pressure relief valve. Further, the percutaneous sheath 300 can beneficially be configured to allow irrigation into the treatment site independent of other percutaneous devices (e.g., lithotripters, nephroscopes).

Like the percutaneous sheath 200 described above, in some embodiments, the percutaneous sheath 300 can include one or more sensors positioned thereon for measuring various parameters. For example, the percutaneous sheath 300 can include a pressure sensor for measuring a pressure within the kidney, a flow sensor for measuring a flow rate into the kidney, and/or a flow sensor for measuring a flow rate out of the kidney. These sensors can be positioned on or within the conduit 306, the hub 316, or elsewhere on the percutaneous sheath 300.

The percutaneous sheaths 200, 300 described in this section can advantageously provide a conduit for irrigation. Other sheaths do not provide conduits for irrigation. While some other sheaths may include side ports, these function to flush the devices or to provide intermittent injection of solution. They are not intended to provide a constant supply of irrigation like the fluid inlets 210, 310 of the percutaneous sheaths 200, 300.

B. Example Systems.

FIG. 24 schematically illustrates an embodiment of a system 400 that includes a percutaneous sheath 200, an catheter 250, and a fluidics system 402. Although the system 400 is illustrated with the percutaneous sheath 200, in some embodiments, the system 400 may use the percutaneous sheath 300.

In the illustrated embodiment, the percutaneous sheath 200 is inserted into a treatment site (e.g., a kidney). The catheter 250 is inserted through the inner conduit 208 of the percutaneous sheath 200 and into the treatment site. The fluid inlet 210 of the percutaneous sheath 200 is connected to the fluidics system 402. The catheter 250 is also connected to the fluidics system 402. The fluidics system 402 can be configured to manage irrigation and aspiration.

For example, the fluidics system 402 can include a pump 404 connected to an irrigation source 408 (e.g., a saline bag or tank). The pump 404 can pump irrigant from the irrigation source to the fluid inlet 210. The irrigant can flow through the first channel 212 (see FIG. 21C) and into the treatment site. The fluidics system 402 can also include a vacuum 406 (or pump) connected to a waste container 410. The vacuum 406 can provide suction to the catheter 250 to aspirate fluid from the treatment site. The aspirated fluid can be pumped to the waste container 410.

The fluidics system 402 can be configured to balance or otherwise manage irrigation and aspiration. In some embodiments, the fluidics system 402 can comprise a processor configured to implement one or more computer-implemented methods for managing inflow and outflow from the treatment site. In some embodiments, the processor receives inputs from one or more sensors on the percutaneous sheath 200, catheter 250, or elsewhere regarding the fluid flow rates and/or pressures of the system 400.

As illustrated in FIG. 24, in some embodiments, the percutaneous sheath 200 provides for passive outflow from the treatment site. For example, such passive outflow can flow through the second channel 214 as described above with reference to FIG. 21C.

In some embodiments, the system 400 also includes a medical instrument 420, such as an endoscope or ureteroscope inserted through another orifice into the treatment site. The medical instrument 420 can be robotically controlled. In some embodiments, irrigation or aspiration is provided may also be provided through the medical instrument 420 or through an access sheath associated with the medical instrument 420.

In some embodiments, the system 400 can include one or more additional percutaneous sheaths and/or percutaneously inserted medical instruments. Additional irrigation and/or aspiration can be provided through these devices.

In some embodiments, the aspirations catheter 250 can also provide irrigation. For example, there can be an aspiration channel and an irrigation channel within the catheter 250.

C. Example Methods.

Figure 25:
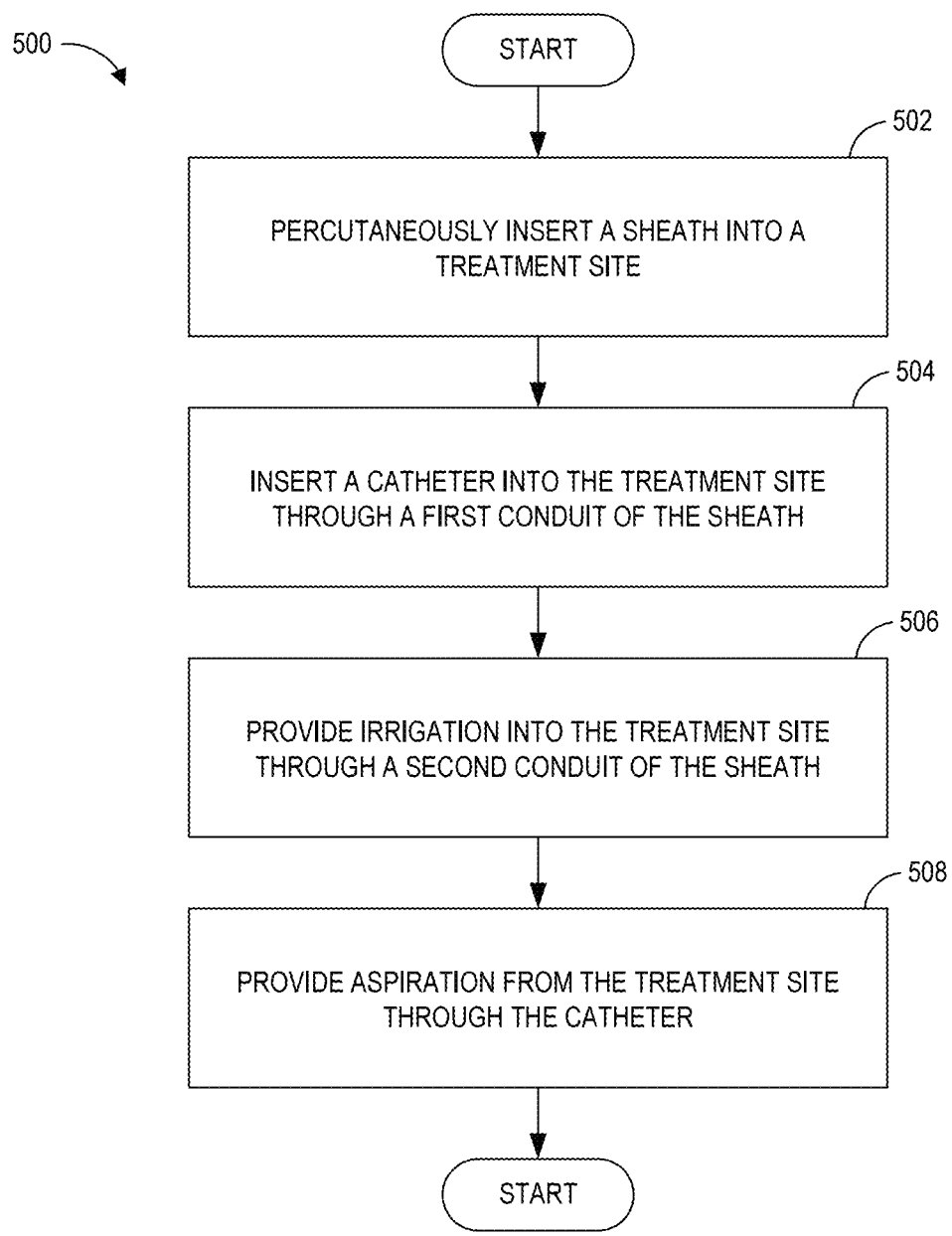
FIG. 25 is a flow chart illustrating an example method for performing a percutaneously assisted medical procedure using a percutaneous sheath as described herein.

FIG. 25 is a flow chart illustrating an example method 500 for performing a percutaneously assisted medical procedure using a percutaneous sheath as described herein. In the illustrated embodiment, the method 500 begins at block 502, at which a sheath (e.g., any of the percutaneous sheaths 200, 300 described above) is percutaneously inserted into a treatment site. In some embodiments, percutaneously inserting the renal sheath into the kidney comprises percutaneously inserting a dilator into the kidney, inserting the renal sheath over the dilator, and removing the dilator. In some embodiments, the outer conduit 206 of the percutaneous sheath 200 is inserted over the dilator, and, when the dilator is removed, the inner conduit 208 can be inserted into the outer conduit.

Next, at block 504, a catheter is inserted into the treatment site through a first conduit of the sheath. In some embodiments, this may comprise inserting the catheter into the treatment site through the first conduit of the sheath by inserting the catheter through the hub or valve of the sheath. In some embodiments, the catheter is robotically controlled. For example, the catheter can be robotically inserted through the sheath.

The method 500 then moves to block 506, at which irrigation is provided into the treatment site through a second conduit of the sheath. In some embodiments, this may comprise connecting a fluid inlet of the sheath to an irrigation source of a fluidics system. The fluid inlet can be connected to the second conduit of the sheath. The fluid inlet can comprise a side port. The side port can be positioned on a hub of the sheath.

Finally, at block 508, aspiration is provided from the treatment site through the catheter. In some embodiments, this may comprise connecting the catheter to an aspiration source of a fluidics system.

In some embodiments, the method 500 may also include providing passive outflow from the treatment site through the sheath as described above (e.g., as shown in FIG. 24). For example, passive outflow can occur through the first conduit of the sheath. In some embodiments, the passive outflow flows through a channel formed between the first conduit of the sheath and the catheter (e.g., the second channel 214).

In some embodiments, the method 500 may further comprise inserting an endoscope into the kidney through a natural patient orifice, performing lithotomy with the endoscope to break a kidney stone into fragments, and aspirating the fragments through the catheter. In some embodiments, the endoscope is robotically controlled.

In some embodiments, the percutaneous access sheath can be configured to facilitate, maintain, or regulate a desirable pressure within the treatment site (e.g., in the case of the kidney, an intrarenal pressure). This can be accomplished, for example, by designing, varying, or controlling parameters of the percutaneous access sheath such that a resistance ration of the percutaneous access sheath can be reduced. As used herein, the resistance ratio of the percutaneous access sheath can be a ration of the outflow resistance of the sheath to the inflow resistance of the sheath. Decreasing the resistance ratio can advantageously be useful in limiting or preventing over pressurization or distention of the treatment site. This can be because as the resistance ration decreases, outflow through the sheath (which can include both active and passive outflow as described above) is increased compared to inflow through the sheath. Various parameters of the sheath can be adjusted or controlled to vary the resistance ratio, including the outer and inner diameters of the outer conduit, the outer and inner diameters of the inner conduit, wall thicknesses of the outer and inner conduits, lengths of the outer and inner conduits, and the diameter of a tool (e.g., a catheter) inserted through the working channel of the access sheath.

For example, an example method for decreasing the resistance ratio of the percutaneous access sheath can include increasing the inflow resistance of the sheath. In some embodiments, increasing the inflow resistance of the sheath can include, for example, increasing the outer diameter of the inner conduit and/or decreasing the outer diameter of the outer conduit. As another example, a method for decreasing the resistance ratio of the sheath can include decreasing the outflow resistance of the sheath. In some embodiments, decreasing the outflow resistance of the sheath in include, for example, decreasing the length of the inner conduit the sheath, decreasing the inner diameter of a catheter inserted through the working channel of the sheath (in order to decrease an aspiration cross-section of the sheath (e.g., active outflow), and/or decreasing an outer diameter of catheter inserted through the working channel and/or increasing the inner diameter of the inner conduit of the sheath (to increase an outflow cross-section of the sheath (e.g., passive outflow).

As another example, in some embodiments, the percutaneous access sheath is configured such that a length of the inner conduit can be adjusted. Increasing the length can increase the outflow resistance, increasing the resistance ratio. Decreasing the length can decrease the outflow resistance, decreasing the resistance ratio. Alternatively or additionally, the percutaneous access sheath can be configured such that a length of the outer conduit can be adjusted. Increasing the length of the outer conduit can increase inflow resistance, decreasing the resistance ratio. Decreasing the length of the outer conduit can decrease inflow resistance, increasing the resistance ratio.

3. Implementing Systems and Terminology.

Implementations disclosed herein provide systems, methods and apparatus that include percutaneous sheaths.

It should be noted that the terms "couple," "coupling," "coupled" or other variations of the word couple as used herein may indicate either an indirect connection or a direct connection. For example, if a first component is "coupled" to a second component, the first component may be either indirectly connected to the second component via another component or directly connected to the second component.

The phrases referencing specific computer-implemented processes and functions described herein may be stored as one or more instructions on a processor-readable or computer-readable medium. The term "computer-readable medium" refers to any available medium that can be accessed by a computer or processor. By way of example, and not limitation, such a medium may comprise random access memory (RAM), read-only memory (ROM), electrically erasable programmable read-only memory (EEPROM), flash memory, compact disc read-only memory (CD-ROM) or other optical disk storage, magnetic disk storage or other magnetic storage devices, or any other medium that can be used to store desired program code in the form of instructions or data structures and that can be accessed by a computer. It should be noted that a computer-readable medium may be tangible and non-transitory. As used herein, the term "code" may refer to software, instructions, code or data that is/are executable by a computing device or processor.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

As used herein, the term "plurality" denotes two or more. For example, a plurality of components indicates two or more components. The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

The previous description of the disclosed implementations is provided to enable any person skilled in the art to make or use the present invention. Various modifications to these implementations will be readily apparent to those skilled in the art, and the generic principles defined herein may be applied to other implementations without departing from the scope of the invention. For example, it will be appreciated that one of ordinary skill in the art will be able to employ a number corresponding alternative and equivalent structural details, such as equivalent ways of fastening, mounting, coupling, or engaging tool components, equivalent mechanisms for producing particular actuation motions, and equivalent mechanisms for delivering electrical energy. Thus, the present invention is not intended to be limited to the implementations shown herein but is to be accorded the widest scope consistent with the principles and novel features disclosed herein.

What is claimed is:

1. A percutaneous sheath comprising:
   an outer conduit extending between a proximal end and a distal end, the outer conduit including a first distal axial opening;
   an inner conduit arranged within and coupled to the outer conduit such that the outer conduit extends axially beyond a distal end of the inner conduit, the inner conduit including a proximal opening and a second distal axial opening that is concentric with the first distal axial opening;
   a plurality of radially-projecting wings projecting from a proximal end portion of the inner conduit;
   an irrigant fluid inlet connected to an irrigation source;
   a first channel defined between an inner wall of the outer conduit and an outer wall of the inner conduit, the first channel being connected to the irrigant fluid inlet and configured to provide irrigation of a fluid into a kidney;
   a pressure relief valve associated with the irrigant fluid inlet, the pressure relief valve being configured to expel irrigant fluid when fluid pressure within at least a portion of the irrigant fluid inlet exceeds a threshold; and
   a second channel formed by an inner wall of the inner conduit, the second channel configured to allow a catheter to:
     be inserted through the second channel and out of the first and second distal axial openings into the kidney; and
     provide for passive outflow of the fluid from the kidney through the inner conduit in a space between the catheter and the inner wall of the inner conduit;
   wherein the space between the catheter and the inner wall of the inner conduit extends from the second distal axial opening of the inner conduit to the proximal opening of the inner conduit, such that the passive outflow of the fluid can pass through the second channel from the second distal axial opening to the proximal opening of the inner conduit.

2. The percutaneous sheath of claim 1, wherein the irrigant fluid inlet comprises a side port positioned on a first hub attached to a proximal end portion of the outer conduit.

3. The percutaneous sheath of claim 1, further comprising a second hub disposed at the proximal end portion of the inner conduit, wherein the second hub engages the first hub to seal a proximal end of the first channel.

4. The percutaneous sheath of claim 1, wherein the outer conduit and the inner conduit are concentrically arranged.

5. The percutaneous sheath of claim 1, wherein the inner conduit provides an open passage through the percutaneous sheath.

6. The percutaneous sheath of claim 1, wherein:
   the outer conduit comprises a stainless steel hypotube; and
   the inner conduit comprises a stainless steel hypotube.

7. The percutaneous sheath of claim 1, wherein:
   an outer diameter of the outer conduit is about 23 Fr.;
   an inner diameter of the outer conduit is about 21.4 Fr.;
   an outer diameter of the inner conduit is about 19.1 Fr.; and
   an inner diameter of the inner conduit is about 18.1 Fr.

8. The percutaneous sheath of claim 1, further comprising a pressure sensor for measuring a pressure within the kidney.

9. The percutaneous sheath of claim 1, further comprising a flow sensor for measuring a flow rate into the kidney.

10. The percutaneous sheath of claim 1, further comprising a flow sensor for measuring a flow rate out of the kidney.

11. The percutaneous sheath of claim 1, wherein the first channel is distally open at a distal end of the outer conduit and a distal end of the inner conduit.

12. The percutaneous sheath of claim 1, wherein the first channel circumferentially surrounds an entire circumference of the inner conduit.

13. The percutaneous sheath of claim 1, wherein the inner conduit is proximally removable from the percutaneous sheath by manually manipulating the plurality of radially-projecting wings.

14. A sheath comprising:
   an outer tube configured to be percutaneously inserted into anatomy of a patient, the outer tube including a first distal axial opening;
   a first hub coupled to a proximal end of the outer tube, the first hub comprising:
     an irrigant fluid port; and
     a pressure relief valve associated with the irrigant fluid port;
   an inner tube configured to be disposed within the outer tube, an inner wall of the inner tube defining an inner channel, the inner tube including a proximal opening and a second distal axial opening that is concentric with the first distal axial opening; and a second hub coupled to a proximal end of the inner tube and configured to be coupled to the first hub and provide a fluid seal between the first hub and the second hub, the second hub comprising a plurality of radially-projecting fins;

wherein, when the first hub is coupled to the second hub:
- the outer tube extends beyond a distal end of the inner tube;
- an outer irrigant fluid channel is defined between an inner wall of the outer tube and an outer wall of the inner tube;
- the outer irrigant fluid channel is in fluid communication with the irrigant fluid port; and
- fluid outflow is permitted in a space between a working instrument disposed within the inner tube and the inner wall of the inner tube, the working instrument being passed through the first and second distal axial openings;

wherein:
- the space between the working instrument and the inner wall of the inner tube extends from the second distal axial opening of the inner tube to the proximal opening of the inner tube, such that the fluid outflow can pass through the inner tube from the second distal axial opening to the proximal opening of the inner tube;

the pressure relief valve is configured to expel irrigant fluid from the outer irrigant fluid channel when fluid pressure within at least one of the outer irrigant fluid channel or the irrigant fluid port exceeds a threshold level.

15. The sheath of claim 14, wherein the second hub includes an outer threaded portion configured to engage with a corresponding inner threaded portion of the first hub.

16. The sheath of claim 14, wherein, when the first hub is coupled to the second hub, the inner tube extends through a second pressure relief valve associated with the inner channel.

17. The sheath of claim 14, wherein the inner channel is axially open at proximal and distal ends thereof.

18. The sheath of claim 14, wherein the outer irrigant fluid channel is axially open at a distal end of the inner tube.

19. The sheath of claim 14, wherein the fluid seal proximally seals the outer irrigant fluid channel.

20. The sheath of claim 19, wherein the irrigant fluid port is positioned distal of the fluid seal.

21. The sheath of claim 14, wherein the pressure relief valve comprises a rubber diaphragm valve configured to rupture when subject to pressure greater than the threshold level.

* * * * *